(12) United States Patent
Cacatian et al.

(10) Patent No.: US 9,079,861 B2
(45) Date of Patent: Jul. 14, 2015

(54) CYCLIC UREA INHIBITORS OF 11β-HYDROXYSTEROID DEHYDROGENASE 1

(75) Inventors: Salvacion Cacatian, Conshohocken, PA (US); David A. Claremon, Maple Glenn, PA (US); Wei He, Audubon, PA (US); Suresh B. Singh, Kendall Park, NJ (US); Colin M. Tice, Maple Glen, PA (US); Zhenrong Xu, Chalfont, PA (US); Yuanjie Ye, Ambler, PA (US); Wei Zhao, Eagleville, PA (US); Linghang Zhuang, Chalfont, PA (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 927 days.

(21) Appl. No.: 12/745,663

(22) PCT Filed: Nov. 7, 2008

(86) PCT No.: PCT/US2008/012618
§ 371 (c)(1),
(2), (4) Date: Aug. 31, 2010

(87) PCT Pub. No.: WO2009/061498
PCT Pub. Date: May 14, 2009

(65) Prior Publication Data
US 2010/0324045 A1   Dec. 23, 2010

Related U.S. Application Data

(60) Provisional application No. 61/002,157, filed on Nov. 7, 2007.

(51) Int. Cl.
| | | |
|---|---|---|
| *A61K 31/535* | (2006.01) | |
| *A61K 31/505* | (2006.01) | |
| *C07D 239/10* | (2006.01) | |
| *C07D 401/04* | (2006.01) | |
| *C07D 401/10* | (2006.01) | |
| *C07D 403/06* | (2006.01) | |
| *C07D 409/04* | (2006.01) | |
| *C07D 409/10* | (2006.01) | |
| *C07D 417/10* | (2006.01) | |

(52) U.S. Cl.
CPC ............ *C07D 239/10* (2013.01); *C07D 401/04* (2013.01); *C07D 401/10* (2013.01); *C07D 403/06* (2013.01); *C07D 409/04* (2013.01); *C07D 409/10* (2013.01); *C07D 417/10* (2013.01)

(58) Field of Classification Search
None
See application file for complete search history.

(56) References Cited

U.S. PATENT DOCUMENTS

| | | |
|---|---|---|
| 3,341,538 A | 9/1967 | Block et al. |
| 3,378,587 A | 4/1968 | Reinhardt |
| 3,681,349 A | 8/1972 | Schwan et al. |
| 3,703,529 A | 11/1972 | Frederick et al. |
| 3,919,047 A | 11/1975 | Vidic et al. |
| 4,009,171 A | 2/1977 | Albertson |
| 4,043,927 A | 8/1977 | Duling et al. |
| 4,108,857 A | 8/1978 | Albertson |
| 4,136,145 A | 1/1979 | Fuchs et al. |
| 4,136,162 A | 1/1979 | Fuchs et al. |
| 4,268,673 A | 5/1981 | Akkerman et al. |
| 5,089,506 A | 2/1992 | Gray et al. |
| 5,098,916 A | 3/1992 | Gray et al. |
| 5,215,992 A | 6/1993 | Gray et al. |
| 5,393,735 A | 2/1995 | Lange et al. |
| 5,410,081 A | 4/1995 | Kunde et al. |

(Continued)

FOREIGN PATENT DOCUMENTS

| | | |
|---|---|---|
| EP | 0415642 A1 | 3/1991 |
| EP | 0454444 A1 | 10/1991 |

(Continued)

OTHER PUBLICATIONS

Kashima et al (J Heterocyclic Chem 18:1595-1596, 1981).*
Anderson (Chem and Biol 10:787-797, 2003).*
Thiel (Nature Biotechnol 2:513-519, 2004).*
MS Bitar, "Glucocorticoid Dynamics and Impaired Wound Healing in Diabetes Mellitus", Am J Pathol., 1998, vol. 152, pp. 547-554.
MS Bitar, et al., "Heat-Shock Protein 72/73 and Impaired Wound Healing in Diabetic and Hypercortisolemic States", Sugery, 1999, vol. 125, pp. 594-601.

(Continued)

*Primary Examiner* — Craig Ricci
(74) *Attorney, Agent, or Firm* — McCarter & English LLP; Steven G. Davis; Michael J. DeGrazia

(57) ABSTRACT

This invention relates to novel compounds of the Formula (I), (Ia), (Ib), (Ic), (Id), (Ie), (If), (Ig), (Ih)1 (Ij), (Ik), (Il$^{1-3}$). (Im$^{1-3}$), (In$^{1-3}$), (Io$^{1-2}$), (Ip$^{1-6}$), (Iq$^{1-6}$), (Ir$^{1-6}$) and (Is$^{1-2}$), pharmaceutically acceptable salts thereof, and pharmaceutical compositions thereof, which are useful for the therapeutic treatment of diseases associated with the modulation or inhibition of 11β-HSD1 in mammals. The invention further relates to pharmaceutical compositions of the novel compounds and methods for their use in the reduction or control of the production of Cortisol in a cell or the inhibition of the conversion of cortisone to Cortisol in a cell.

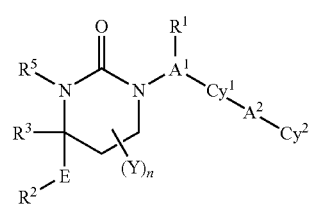

16 Claims, No Drawings

(56) References Cited

U.S. PATENT DOCUMENTS

| | | |
|---|---|---|
| 5,432,175 A | 7/1995 | Piwinski et al. |
| 5,480,899 A | 1/1996 | Yano et al. |
| 5,502,027 A | 3/1996 | Lange et al. |
| 5,631,209 A | 5/1997 | Lange et al. |
| 5,776,959 A | 7/1998 | Covey et al. |
| 5,780,466 A | 7/1998 | Emonds-Alt et al. |
| 5,811,422 A | 9/1998 | Lam et al. |
| 5,856,273 A | 1/1999 | Kay et al. |
| 5,866,702 A | 2/1999 | Mackman et al. |
| 5,936,124 A | 8/1999 | Hilborn et al. |
| 5,981,436 A | 11/1999 | Drewes et al. |
| 6,066,666 A | 5/2000 | Covey et al. |
| 6,159,990 A | 12/2000 | Lagu et al. |
| 6,242,637 B1 | 6/2001 | Emonds-Alt et al. |
| 6,251,897 B1 | 6/2001 | Ina et al. |
| 6,368,816 B2 | 4/2002 | Walker et al. |
| 6,559,163 B2 | 5/2003 | Cai et al. |
| 6,620,815 B1 | 9/2003 | Lagu et al. |
| 6,635,630 B2 | 10/2003 | Shih et al. |
| 6,638,935 B2 | 10/2003 | Emig et al. |
| 6,653,315 B2 | 11/2003 | Tulshian et al. |
| 6,706,722 B2 | 3/2004 | Emig et al. |
| 6,794,390 B2 | 9/2004 | Lum et al. |
| 6,838,253 B2 | 1/2005 | Walker et al. |
| 6,841,671 B2 | 1/2005 | Noe et al. |
| 6,890,926 B2 | 5/2005 | Emig et al. |
| 6,900,201 B2 | 5/2005 | Noe et al. |
| 6,916,807 B2 | 7/2005 | Freeman-Cook et al. |
| 6,936,615 B2 | 8/2005 | Emig et al. |
| 6,946,487 B2 | 9/2005 | Walker et al. |
| 7,026,310 B2 | 4/2006 | Emig et al. |
| 7,056,912 B2 | 6/2006 | Emig et al. |
| 7,087,400 B2 | 8/2006 | Walker et al. |
| 7,122,531 B2 | 10/2006 | Walker et al. |
| 7,122,532 B2 | 10/2006 | Walker et al. |
| 7,129,231 B2 | 10/2006 | Walker et al. |
| 7,132,551 B2 | 11/2006 | Aquila et al. |
| 7,186,844 B2 | 3/2007 | Ikemoto |
| 7,208,487 B2 | 4/2007 | Bergnes et al. |
| 7,253,198 B2 | 8/2007 | Demont et al. |
| 7,256,005 B2 | 8/2007 | Zitzmann et al. |
| 7,262,212 B2 | 8/2007 | Tsubouchi et al. |
| 7,294,637 B2 | 11/2007 | Aquila et al. |
| 7,417,045 B2 | 8/2008 | Anilkumar et al. |
| 7,566,718 B2 | 7/2009 | Wong et al. |
| 7,652,049 B2 | 1/2010 | Ali et al. |
| 7,897,773 B2 | 3/2011 | Aletru et al. |
| 8,114,868 B2 | 2/2012 | Himmelsbach |
| 8,138,178 B2 | 3/2012 | Claremon et al. |
| 8,202,857 B2 | 6/2012 | Claremon et al. |
| 8,242,111 B2 | 8/2012 | Claremon et al. |
| 8,329,897 B2 | 12/2012 | Xu |
| 8,440,658 B2 | 5/2013 | Claremon et al. |
| 2001/0039286 A1 | 11/2001 | Dinnell et al. |
| 2006/0063819 A1 | 3/2006 | Lanter et al. |
| 2006/0089349 A1 | 4/2006 | Gundertofte et al. |
| 2006/0116382 A1 | 6/2006 | Yao et al. |
| 2006/0194780 A1 | 8/2006 | Nargund et al. |
| 2006/0276457 A1 | 12/2006 | Yu et al. |
| 2006/0276479 A1 | 12/2006 | Kim et al. |
| 2006/0276480 A1 | 12/2006 | Wong et al. |
| 2007/0021611 A1 | 1/2007 | McGuinness et al. |
| 2007/0054919 A1 | 3/2007 | Rosenblum et al. |
| 2007/0082913 A1 | 4/2007 | Kim et al. |
| 2007/0129345 A1 | 6/2007 | Zhuo et al. |
| 2007/0208001 A1 | 9/2007 | Zhuo et al. |
| 2007/0219182 A1 | 9/2007 | Lubisch et al. |
| 2007/0254875 A1 | 11/2007 | Zhi et al. |
| 2007/0254901 A1 | 11/2007 | Bilodeau et al. |
| 2007/0259891 A1 | 11/2007 | Strobel et al. |
| 2008/0004300 A1 | 1/2008 | Strobel et al. |
| 2008/0021029 A1 | 1/2008 | Strobel et al. |
| 2008/0045518 A1 | 2/2008 | Commons et al. |
| 2008/0045578 A1 | 2/2008 | Commons et al. |
| 2008/0045579 A1 | 2/2008 | Commons et al. |
| 2008/0124384 A1 | 5/2008 | Blum |
| 2008/0188482 A1 | 8/2008 | Rice et al. |
| 2008/0249087 A1 | 10/2008 | Rotstein et al. |
| 2008/0269295 A1 | 10/2008 | Haurand et al. |
| 2008/0280933 A1 | 11/2008 | Efremov et al. |
| 2008/0312271 A1 | 12/2008 | Efremov et al. |
| 2009/0018054 A1 | 1/2009 | Ali et al. |
| 2009/0170894 A1 | 7/2009 | Aletru et al. |
| 2009/0264650 A1 | 10/2009 | Cho et al. |
| 2010/0016164 A1 | 1/2010 | Hino et al. |
| 2010/0025636 A1 | 2/2010 | Gelbin et al. |
| 2010/0041637 A1 | 2/2010 | Claremon et al. |
| 2010/0197675 A1 | 8/2010 | Claremon et al. |
| 2010/0256363 A1 | 10/2010 | Xu |
| 2010/0331320 A1 | 12/2010 | Renz et al. |
| 2011/0009402 A1 | 1/2011 | Himmelsbach |
| 2011/0015157 A1 | 1/2011 | Claremon et al. |
| 2011/0019643 A1 | 1/2011 | Kim et al. |
| 2011/0021512 A1 | 1/2011 | Claremon et al. |
| 2011/0028445 A1 | 2/2011 | Eckhardt et al. |
| 2011/0034455 A1 | 2/2011 | Claremon et al. |
| 2011/0039286 A1 | 2/2011 | Wu et al. |
| 2011/0053943 A1 | 3/2011 | Claremon et al. |
| 2011/0071139 A1 | 3/2011 | Claremon et al. |
| 2011/0098320 A1 | 4/2011 | Claremon et al. |
| 2011/0105504 A1 | 5/2011 | Claremon et al. |
| 2011/0112062 A1 | 5/2011 | Claremon et al. |
| 2011/0112082 A1 | 5/2011 | Claremon et al. |
| 2011/0124635 A1 | 5/2011 | Claremon et al. |
| 2011/0136800 A1 | 6/2011 | Eckhardt et al. |
| 2011/0136821 A1 | 6/2011 | Claremon et al. |
| 2011/0190262 A1 | 8/2011 | Himmelsbach et al. |
| 2011/0224242 A1 | 9/2011 | Giethlen et al. |
| 2011/0263582 A1 | 10/2011 | Claremon et al. |
| 2011/0263583 A1 | 10/2011 | Claremon et al. |
| 2011/0263584 A1 | 10/2011 | Claremon et al. |
| 2011/0269736 A1 | 11/2011 | Eckhardt et al. |
| 2011/0269791 A1 | 11/2011 | Peters et al. |
| 2011/0269957 A1 | 11/2011 | Fandrick et al. |
| 2011/0275595 A1 | 11/2011 | Eckhardt et al. |
| 2011/0312950 A1 | 12/2011 | Eckhardt et al. |
| 2012/0040973 A1 | 2/2012 | Claremon et al. |
| 2012/0108578 A1 | 5/2012 | Himmelsbach et al. |
| 2012/0108579 A1 | 5/2012 | Renz et al. |
| 2012/0115853 A1 | 5/2012 | Eckhardt et al. |
| 2012/0172357 A1 | 7/2012 | Himmelsbach |
| 2012/0178746 A1 | 7/2012 | Claremon et al. |
| 2012/0184549 A1 | 7/2012 | Himmelsbach |
| 2012/0190675 A1 | 7/2012 | Himmelsbach |
| 2012/0208804 A1 | 8/2012 | Claremon et al. |
| 2012/0232050 A1 | 9/2012 | Claremon et al. |
| 2012/0277149 A1 | 11/2012 | Hamilton et al. |
| 2012/0277455 A1 | 11/2012 | Qu et al. |

FOREIGN PATENT DOCUMENTS

| | | |
|---|---|---|
| EP | 0640594 A1 | 3/1995 |
| EP | 0645387 A | 3/1995 |
| EP | 0471591 B1 | 5/1995 |
| EP | 0847275 A1 | 6/1998 |
| EP | 0928789 A1 | 7/1999 |
| EP | 1156049 A | 11/2001 |
| EP | 1270724 A2 | 1/2003 |
| EP | 1801098 A1 | 6/2007 |
| EP | 1852425 A | 11/2007 |
| EP | 1864971 A | 12/2007 |
| EP | 1935420 | 6/2008 |
| GB | 1077711 | 8/1967 |
| WO | WO 92/07838 | 5/1992 |
| WO | WO 93/07128 | 4/1993 |
| WO | WO 93/13103 | 7/1993 |
| WO | 96/37494 A1 | 11/1996 |
| WO | 97/07789 A1 | 3/1997 |
| WO | WO 97/36605 | 10/1997 |
| WO | 98/22462 A1 | 5/1998 |
| WO | WO 98/57940 | 12/1998 |
| WO | WO 99/06395 | 2/1999 |
| WO | 0009107 A2 | 2/2000 |
| WO | 0113917 A1 | 3/2001 |

(56) References Cited

FOREIGN PATENT DOCUMENTS

| | | |
|---|---|---|
| WO | WO 01/44200 A2 | 6/2001 |
| WO | WO 01/55063 | 8/2001 |
| WO | WO 02/22572 A2 | 3/2002 |
| WO | WO 03/057673 A | 7/2003 |
| WO | 03/097608 A2 | 11/2003 |
| WO | WO 03/093261 A1 | 11/2003 |
| WO | WO 2004/004722 A1 | 1/2004 |
| WO | WO 2004/009559 A2 | 1/2004 |
| WO | WO 2004/014859 A2 | 2/2004 |
| WO | 2004/046137 A1 | 6/2004 |
| WO | 2004056745 A2 | 7/2004 |
| WO | 2004/089896 A1 | 10/2004 |
| WO | WO 2004/094375 A | 11/2004 |
| WO | WO 2005/000845 | 1/2005 |
| WO | WO 2005/086700 A2 | 9/2005 |
| WO | 2005108360 A1 | 11/2005 |
| WO | WO 2005/108361 | 11/2005 |
| WO | WO 2005/108361 A | 11/2005 |
| WO | 2005116002 A2 | 12/2005 |
| WO | WO 2005/113525 A1 | 12/2005 |
| WO | 2006002349 A1 | 1/2006 |
| WO | WO 2006/003494 A2 | 1/2006 |
| WO | 2006017443 | 2/2006 |
| WO | WO 2006/014357 A | 2/2006 |
| WO | WO 2006/024627 A2 | 3/2006 |
| WO | WO 2006/024628 A | 3/2006 |
| WO | WO 2006/031715 A | 3/2006 |
| WO | WO 2006/040329 | 4/2006 |
| WO | WO 2006/044174 | 4/2006 |
| WO | WO 2006/049952 A | 5/2006 |
| WO | WO 2006/066924 A2 | 6/2006 |
| WO | WO 2006/066948 A1 | 6/2006 |
| WO | 2006/109056 A1 | 10/2006 |
| WO | WO 2007/008529 A2 | 1/2007 |
| WO | 2007/022371 A2 | 2/2007 |
| WO | 2007/048595 A1 | 5/2007 |
| WO | WO 2007/051810 | 5/2007 |
| WO | WO 2007/061661 A2 | 5/2007 |
| WO | WO 2007/068330 A1 | 6/2007 |
| WO | 2007/076055 A2 | 7/2007 |
| WO | WO 2007/079186 A2 | 7/2007 |
| WO | WO 2007/081569 A2 | 7/2007 |
| WO | WO 2007/081570 A | 7/2007 |
| WO | WO 2007/081571 A2 | 7/2007 |
| WO | WO 2007/084314 A2 | 7/2007 |
| WO | 2007101270 A1 | 9/2007 |
| WO | 2007103719 A2 | 9/2007 |
| WO | WO 2007/109456 A2 | 9/2007 |
| WO | WO 2007/118185 A2 | 10/2007 |
| WO | 2007/123853 A2 | 11/2007 |
| WO | 2007/127763 A2 | 11/2007 |
| WO | WO 2007/124254 | 11/2007 |
| WO | WO 2007/124329 A | 11/2007 |
| WO | WO 2007/124337 | 11/2007 |
| WO | WO 2007/127693 A | 11/2007 |
| WO | WO 2008/000951 | 1/2008 |
| WO | 2008024497 A2 | 2/2008 |
| WO | WO 2008/031227 A1 | 3/2008 |
| WO | WO 2008/036715 A1 | 3/2008 |
| WO | WO 2008/046758 A | 4/2008 |
| WO | WO 2008/106128 | 9/2008 |
| WO | WO 2008/106128 A | 9/2008 |
| WO | WO 2008/118332 A2 | 10/2008 |
| WO | WO 2009/017664 | 2/2009 |
| WO | WO 2009/017664 A1 | 2/2009 |
| WO | WO 2009/017671 | 2/2009 |
| WO | WO 2009/061498 | 5/2009 |
| WO | WO 2009/063061 | 5/2009 |
| WO | WO 2009/075835 | 6/2009 |
| WO | WO 2009/088997 | 7/2009 |
| WO | WO 2009/094169 A | 7/2009 |
| WO | WO 2009/100872 | 8/2009 |
| WO | WO 2009/102428 | 8/2009 |
| WO | WO 2009/102460 | 8/2009 |
| WO | 2009108332 A1 | 9/2009 |
| WO | WO 2009/117109 | 9/2009 |
| WO | 2009131669 A2 | 10/2009 |
| WO | WO 2009/134384 | 11/2009 |
| WO | WO 2009/134387 | 11/2009 |
| WO | WO 2009/134392 | 11/2009 |
| WO | WO 2009/134400 | 11/2009 |
| WO | WO 2009/138386 | 11/2009 |
| WO | 2010/010150 A1 | 1/2010 |
| WO | WO 2010/010149 | 1/2010 |
| WO | WO 2010/010157 | 1/2010 |
| WO | WO 2010/010174 | 1/2010 |
| WO | WO 2010/011314 | 1/2010 |
| WO | WO 2010/023161 | 3/2010 |
| WO | WO 2010/046445 | 4/2010 |
| WO | 2010089303 A1 | 8/2010 |
| WO | WO 2010/091067 | 8/2010 |
| WO | 2010104830 A1 | 9/2010 |
| WO | WO 2010/127237 | 11/2010 |
| WO | 2010/139673 A1 | 12/2010 |
| WO | 2010141424 A1 | 12/2010 |
| WO | 2011002910 A1 | 1/2011 |
| WO | 2011011123 A1 | 1/2011 |
| WO | 2011031979 A1 | 3/2011 |
| WO | 2011/057054 A1 | 5/2011 |
| WO | 2011056737 A1 | 5/2011 |
| WO | 2011159760 A1 | 12/2011 |
| WO | 2011161128 A1 | 12/2011 |
| WO | 2012059416 A1 | 5/2012 |

OTHER PUBLICATIONS

MS Bitar, et al., "Glucocorticoid-Dependent Impairment of Wound Healing in Experimental Diabetes: Amelioration by Adrenalectomy and RU 486", J Surg Res., 1999, vol. 82, pp. 234-243.

MS Bitar, "Insulin and Glucocorticoid-Dependent Suppression of the IGF-I System in Diabetic Wounds", Sugery, 2000, vol. 127, pp. 687-695.

Database Caplus [Online] Chemical Abstracts Service, Maillard et al., "Spiroheterocyclic Cycloalkane Compounds. II. Synthesis of 6-Substituted-Tetrahydro-2H-1,3-Oxazine-2-Ones", XP002516521, retrieved from STN Database accession No. 1969:68280 CAS RN: 20057-45-8 abstract.

Chimica Therapeutica, 1968, vol. 3(5), pp. 321-324, 1968.

Database Caplus [Online] Chemical Abstracts Service, Slyusarenko et al., "Synthesis based on Thionylamides.IV. 2-Alkoxy-5,6-Dihydro-1,3-Oxazines", XP002516522, retrieved from STN Database accession No. 1978:563520 CAS RN: 67868-26-2 abstract.

Database CA [Online], Chemical Abstracts Service, Fukushima et al., "Preparation of Imidazolidinone Derivatives as 11.beta.-HSD1 Inhibitors", XP 002531878.

Chemical Abstracts, vol. 98, No. 11, 1983, Columbus, Ohio, US; abstract No. 89280k, Lapkin, et al., "Synthesis of 1,3-oxazin-2,4-diones", p. 552 col. 1, XP002504063 abstract.

Chemical Abstracts, vol. 99, No. 23, 1983, Columbus, Ohio, US; abstract No. 195067b, Saitkulova, et al., "Synthesis involving bromozinc alcoholates of carboxylic acid esters", p. 764 col. 1, XP002504064 abstract.

Goubet, et al., "Conversion of a Thiohydantoin to the Corresponding Hydantoin via a Ring-Opening/Ring Closure Mechanism", Tetrahedron Letters, Elsevier, Amsterdam, 1996, vol. 37, pp. 7727-7730.

Ho-Jane Shue et al., "Cyclic Urea Derivatives as Potent NK1 Selective Antagonists", Bioorganic & Medicinal Chemistry Letters, 2005, vol. 15, pp. 3896-3899.

Ho-Jane Shue et al., "Cyclic Urea Derivatives as Potent NK1 Selective Antagonists. Part II: Effects of Fluoro and Benzylic Methyl Substitutions", Bioorganic & Medicinal Chemistry Letters, 2006, vol. 16, pp. 1065-1069.

Kashima, et al., "Preparation of N-Aryl-2,4-diaminopentanes by the Ring Opening Reaction of 1-Aryl-3,4,5,6-tetrahydro-2-(1H)pyrimidinones", Journal of Heterocyclic Chemistry, vol. 18, 1981, pp. 1595-1596, XP002517485.

Lohray et al., "Enantiospecific Synthesis of 6-Substituted N-Aryl-1,3-Oxazin-2-Ones", Tetrahedron Letters, 1998, vol. 39, pp. 6555-6556.

Malgorzata Wamil and Jonathan R. Seckl, "Inhibition of 11β-hydroxysteroid Dehydrogenase Type 1 as a Promising Therapeutic Target", Drug Discovery Today, 2007, vol. 12, pp. 504-520.

(56) References Cited

OTHER PUBLICATIONS

Muehlstadt, et al., "Cyclisation reactions of beta, gamma-unsaturated derivatives of carbonic acid. IX.", Journal Fuer Praktische Chemie, vol. 328, 1986, pp. 163-172, XP002504062 p. 164, compound 4j.
Suga, Seiji et al., ""N-Acyliminium Ion Pool" as a Heterodiene in [4+2] Cycloaddition Reaction", Organic Letters, 2003, vol. 5, pp. 945-947.
Suga, Seiji et al., "Cycloaddition of "N-Acyliminium Ion Pools" with Carbon—Carbon Multiple Bonds", Bulletin of the Chemical Society of Japan, Chemical Society of Japan, 2005, vol. 78, pp. 1206-1217.
Tamaru et al., "Urea as the Most Reactive and Versatile Nitrogen Nucleophile for the Palladium(2+)-Catalyzed Cyclization of Unsaturated Amines", Journal of the American Chemical Society, 1988, vol. 110, pp. 3994-4002.
Yoshida, Masaaki et al., "Selective synthesis of five- and six-membered cyclic carbamates by the reaction of 2-(1-haloalkyl)oxiranes with carbon dioxide and aliphatic primary amines", Heterocycles, Elsevier Science Ltd., 1993, vol. 35 (2), pp. 623-626.
Yoshinao Tamaru, "Palladium(2+)-Catalyzed Intramolecular Aminocarbonylation of 3-Hydroxy-4-pentenylamines and 4-Hydroxy-5-hexenylamines", J. Org. Chem., 1988, pp. 5731-5741.
International Search Report & Written Opinion—(PCT/US2008/009017) Date of Mailing Apr. 12, 2008.
International Search Report & Written Opinion—(PCT/US2008/002517) Date of Mailing Dec. 29, 2008.
International Search Report—(PCT/US2009/002653) Date of Mailing Jul. 3, 2009.
International Search Report—(PCT/US2009/002641) Date of Mailing Jul. 3, 2009.
International Search Report—(PCT/US2009/002629) Date of Mailing Jul. 3, 2009.
International Search Report—(PCT/US2009/002633) Date of Mailing Jul. 3, 2009.
International Search Report—(PCT/US2008/012618) Date of Mailing Dec. 3, 2009.
International Search Report—(PCT/US2009/000057) Date of Mailing Mar. 25, 2009.
International Search Report—(PCT/US2008/013539) Date of Mailing Mar. 19, 2009.
International Search Report—(PCT/US2009/000853) Date of Mailing Sep. 2, 2009.
International Search Report—(PCT/US2009/000421) Date of Mailing Apr. 15, 2009.
International Search Report—(PCT/US2009/000908) Date of Mailing Sep. 17, 2009.
International Search Report—(PCT/US2009/001712) Date of Mailing Jul. 14, 2009.
Database File Registry [Online], Chemical Abstracts Service, Columbus, Ohio, US, 2007, Database accession No. 958700-63-5, Abstract, XP002556893.
Database File Registry [Online], Chemical Abstracts Service, Columbus, Ohio, US, 2007, Database accession No. 958696-39-4, Abstract, XP002556894.
Database File Registry [Online], Chemical Abstracts Service, Columbus, Ohio, US, 2007, Database accession No. 958696-32-7, Abstract, XP002556895.
Database File Registry [Online], Chemical Abstracts Service, Columbus, Ohio, US, 2007, Database accession No. 958629-39-5, Abstract, XP002556896.
Database File Registry [Online], Chemical Abstracts Service, Columbus, Ohio, US, 2007, Database accession No. 958629-22-6, Abstract, XP002556897.
Database File Registry [Online], Chemical Abstracts Service, Columbus, Ohio, US, 2007, Database accession No. 958629-14-6, Abstract, XP002556898.
Database File Registry [Online], Chemical Abstracts Service, Columbus, Ohio, US, 2007, Database accession No. 958625-83-7, Abstract, XP002556899.
Database File Registry [Online], Chemical Abstracts Service, Columbus, Ohio, US, 2007, Database accession No. 958599-31-0, Abstract, XP002556900.
International Search Report—(PCT/US2010/023021) Date of Mailing Aug. 5, 2010.
U.S. Appl. No. 12/670,205, filed Jul. 25, 2008, Vitae Pharmaceuticals, Inc.
U.S. Appl. No. 12/670,209, filed Jul. 25, 2008, Vitae Pharmaceuticals, Inc.
U.S. Appl. No. 12/741,522, filed Apr. 30, 2009, Vitae Pharmaceuticals, Inc.
U.S. Appl. No. 12/990,309, filed Apr. 30, 2009, Vitae Pharmaceuticals, Inc.
U.S. Appl. No. 12/990,296, filed Apr. 30, 2009, Vitae Pharmaceuticals, Inc.
U.S. Appl. No. 12/811,577, filed Jan. 7, 2009, Vitae Pharmaceuticals, Inc.
U.S. Appl. No. 12/747,391, filed Dec. 10, 2008, Vitae Pharmaceuticals, Inc.
U.S. Appl. No. 12/863,634, filed Jan. 21, 2009, Vitae Pharmaceuticals, Inc.
U.S. Appl. No. 12/867,374, filed Feb. 13, 2009, Vitae Pharmaceuticals, Inc.
U.S. Appl. No. 12/933,027, filed Mar. 18, 2009, Vitae Pharmaceuticals, Inc.
U.S. Appl. No. 12/741,532, filed Sep. 27, 2010, Vitae Pharmaceuticals, Inc.
U.S. Appl. No. 12/771,499, filed Apr. 30, 2010, Vitae Pharmaceuticals, Inc.
International Search Report and Written Opinion—(PCT/US2008/009048) Date of Mailing Dec. 4, 2008.
International Search Report—(PCT/US2009/004261) Date of Mailing Oct. 21, 2009.
Shibata, et al., "Cycloaddition of Oxetanes with Heterocumulenes Catalysed by Organotin Iodine-Lewis Base Complex", Journal of Heterocyclic Chemistry, vol. 24, 1987, pp. 361-363.
Database CA [Online], Chemical Abstracts Service, Fukushima et al., "Preparation of Imidazolidinone Derivatives as 11.beta.-HSD1 Inhibitors", 2007, XP 002531878.
Gavezzotti, "Are Crystal Structures Predictable?", Accounts of Chemical Research, 1994, vol. 27, pp. 309-314.
Vippagunta, et al., "Crystalline Solids", Advanced Drug Deliver Reviews, 2001, vol. 48, pp. 3-26.
Tang, W. et al., "Novel, Tunable, and Efficient Chiral Bisdihydrobenzooxaphosphole Ligands for Asymmetric Hydrogenation". Organic Letters, 2010, vol. 12, No. 1., p. 176-179.
Taddayon et.al. Expert opinion on Investigational Drugs, Ashley Publication Ltd. 2003, vol. 12, No. 3, pp. 307-324.
Thornber et al.: Chem Soc Rev, 1979, vol. 8, p. 563-580.
Vidic et al.: Chem. Ber. 1976, 109, p. 2657-2669.
Worthy, AD. et al., "Regioselective Hydroformylation of Sulfonamides using a Scaffolding Ligand". Organic Letters, 2009, vol. 11, No. 13—p. 2764-2767.
Wolfling, Janos et al., "Neighboring Group Participation Part 15. Stereoselective Synthesis of Some Steroidal Tetrahydrooxaziin-2-ones, as Novel Presumed Inhibitors of Human 5?—Reductase," Steroids, 69: 451-460 (2004).
Yokoyama et al.: J. Med. Chem. 1979, 22, p. 537-553.
Aluri, B.R. et al., "Sterically and Polarity-Controlled Reactions of tBuLi with P=CH-NR Heterocycles: Novel Heterocyclic P-and P,O-Ligands and Preliminary Tests in Transition-Metal Catalysis", Chem. Eur. Journal, vol. 14, 2008, p. 4328-4335.
Aluri. B.R. et al., "Bulky n-Substituted 1,3-Benzazaphospholes: Access via Pd-Catalyzed C—N and C—P Cross Coupling, Lithiation, and Conversion to Novel P=C PtBu2 Hybrid Ligands". Inorganic Chemistry, 2008, 47, p. 6900-6912.
Bosch et al.: Heterocycles 1980, 14, p. 1983-1988.
CA 1267843-31-1, (Aug. 10, 2009). cited by other.
CA 154:284276, (Mar. 17, 2011). cited by other.
Caplus-133:4656—Anantanarayan, A. el. al., "Preparation of heteroarylpyrazoles as P38 kinase inhibitors". 2000.

(56) References Cited

OTHER PUBLICATIONS

Caplus-147:134403, Hembrough, TA, et al., Composition and methods comprising proteinase activated receptor 2 antagonists for treatment of angiogenesis and inflammatory disorders and cancer. 2007.
Caplus-77:5360, Helsley, G. C. "Antispasmodic 8-carbamoyl-3-phenylnortropanes". 1972.
Chalmers (TIPS vol. 17, pp. 166-172 Apr. 1996).
Chemical Abstracts, Registry No. 351443-37-3 (Available on Aug. 15, 2001.).
Chemical Abstracts, vol. 99, No. 23, 1983, Columbus, Ohio, US; abstract No. 195067b, Saitkulova, et al., "Synthesis involving bromozinc alcoholates of carboxylic acid esters", p. 764 col. 1, XP002504064 abstract. cited by other.
Claremon et al. CAS: 150:214405, 2009.
Donohoe, T.J. et al., "Stereoselectivity in the double reductive alkylation of pyrroles: synthesis of cis-3,4-disubstituted pyrrolidines". Chemical Communications, vol. 1999, No. 2, Feb. 1, 1999, p. 141-142.
DeMarinis R.M. et.al. Journal of Medicinal Chemistry 1981, vol. 24, No. 12, pp. 1432-1437.
Evans, B.E. et al., "Orally active, nonpeptide osytocin antagonists". Journal of Medicinal Chemistry, American Chem. Soc., Vo. 35, No. 21, Oct. 15, 1992, p. 3919-3927.
Examiner Interview Summary dated May 2, 2011, in U.S. Appl. No. 12/741,522 (U.S. Patent No. 8,138,178).
Fandrick, Dr. et al., "Copper Catalyzed Asymmetric Propargylation of Aldehydes". JACS Communications, Published on Web May 18, 2010, J. Am. Chem. Soc., vol. 132, No. 22, 2010, p. 7600,7601.
Harno et.al. Trends in Endocrinology and Metabolism, Elsevier Science Publishing, New York 2010, vol. 21, No. 10, pp. 619-627.
Hughes, K.A. et al., "11-beta-hydroxysteroid dehydrogenase type 1 (11b-HSD1) inhibitors in Type 2 diabetes mellitus and obesity". Expert Opinion, Investig. Drugs, 17(4), 2008, pp. 481-496.
International Search Report and Written Opinion for PCT/EP/2009/059496 mailed Nov. 17, 2009.
International Search Report and Written Opinion for PCT/EP2009/059509, mailed Feb. 9, 2009.
International Search Report and Written Opinion for PCT/EP2010/051262 mailed Aug. 7, 2011.
International Search Report and Written Opinion for PCT/EP2011/060386 mailed Sep. 16, 2011.
International Search Report and Written Opinion for PCT/US2010/054912 mailed Mar. 16, 2011.
International Search Report and Written Opinion for PCT/US2012/050679 mailed Oct. 31, 2012.
International Search Report for PCT/EP2009/063913 mailed May 6, 2010.
International Search Report for PCT/EP2011/068938 mailed Mar. 27, 2012.
Kametani et al. Chem Pharma Bull, 1965 vol. 13, No. 3, p. 295-299.
Lightburn, T.E. et al., "Catalytic Scaffolding Ligands: An Efficient Strategy for Direction Reactions". JACS Communications, Published on Web May 25, 2008, Journal American Chem. Soc., vol. 130, No. 29, 2008, p. 9210-9211.
Ma et al.: Synthesis 2007, p. 161-163.
Ma et al.: Tetrahedron 2007, 63, p. 7523-7531.
Morissette et al. Advanced Drug Deliery Reviews 2004, 56, 275-300.
Office Action dated Apr. 3, 2012 for corresponding U.S. Appl. No. 13/318,271.
Office Action dated Jun. 14, 2012 for corresponding U.S. Appl. No. 13/347,784.
Office Action dated May 3, 2012 for corresponding U.S. Appl. No. 13/347,799.
Office Action for U.S. Appl. No. 12/741,522 (U.S. Patent No. 8,138,178), date of mailing Dec. 15, 2010.
Office Action for U.S. Appl. No. 12/741,532 (US Patent No. 8,114,868), date of mailing Dec. 15, 2010.
Office Action for U.S. Appl. No. 12/771,499, date of mailing Dec. 21, 2010.
Olesen et al.: Current Opin Drug Dis Dev, 2001, vol. 4, No. 4, p. 471-478.
Patani et al. Chem Rev, 1996 p. 3147-3176.
Rosenstock et.al. Diabetes Care Jul. 2010, LNKDPUBMED: 20413513, vol. 33, No. 7, pp. 1516-1522.
Senanayake, C. Presentation: "Timely Chemical Process Research is a Critical Part for Efficient Drug Development". 4th Siegfried Symposium, Sep. 23, 2010, p. 1-91, Retrieved from internet: URL: http://www.siegfred/ch/fileadmin/User2/Bilder/Fotogalerien/Symposium_2010/Award_Talk_Senanayake.pdf. Retrieved on Feb. 23, 2010.
Souillac et al., Characterization of Delivery Systems, Differential Scanning Calorimetry, pp. 217-218 (in Encyclopedia of Controlled Drug Delivery, 1999, John Wiley & Sons, pp. 212-227).
Stewart et al. Vitam Horm. 1999;57:249-324.
Sullivan, John M. and Efner, Howard F., "The Preparation of 6-Aryltetrahydro-1,3-oxazin-2-ones and Their Hydrolysis to 3-Substituted Propylamines," The Journal of Organic Chemistry, 33 (5): 2134-2136 (1968). cited by other.
Tamaru, Y. et al., "Palladium (2+)-Catalyzed Intramolecular Aminocarbonylation of 3-Hydroxy-4-pentenylamines and 4-Hydroxy-5-hexenylamines". Journal Organic Chemistry, vol. 53, No. 24, 1988, p. 5731-5741.
Tang, W. et al., "Novel and Efficient Chiral Bisphosphorus Ligands for Rhodium-Catalyzed Asymmetric Hydrogenation". Organic Letters, 2010, vol. 12, No. 5, p. 1104-1107.

\* cited by examiner

CYCLIC UREA INHIBITORS OF 11β-HYDROXYSTEROID DEHYDROGENASE 1

RELATED APPLICATIONS

This application is the U.S. National Stage of International Application No. PCT/US2008/012618, filed Nov. 7, 2008, which claims priority to U.S. Provisional Application No. 61/002,157, filed on Nov. 7, 2007, the entire teachings of which are incorporated herein by reference.

BACKGROUND OF THE INVENTION

Glucocorticoids, such as cortisol (hydrocortisone), are steroid hormones that regulate fat metabolism, function and distribution, and play a role in carbohydrate, protein and fat metabolism. Glucocorticoids are also known to have physiological effects on development, neurobiology, inflammation, blood pressure, metabolism, and programmed cell death. Cortisol and other corticosteroids bind both the glucocorticoid receptor (GR) and the mineralocorticoid receptor (MR), which are members of the nuclear hormone receptor superfamily and have been shown to mediate cortisol function in vivo. These receptors directly modulate transcription via DNA-binding zinc finger domains and transcriptional activation domains.

Until recently, the major determinants of glucocorticoid action were attributed to three primary factors: (1) circulating levels of glucocorticoid (driven primarily by the hypothalamic-pituitary-adrenal (HPA) axis); (2) protein binding of glucocorticoids in circulation; and (3) intracellular receptor density inside target tissues. Recently, a fourth determinant of glucocorticoid function has been identified: tissue-specific pre-receptor metabolism by glucocorticoid-activating and -inactivating enzymes. These 11β-hydroxysteroid dehydrogenase (11β-HSD) pre-receptor control enzymes modulate activation of GR and MR by regulation of glucocorticoid hormones. To date, two distinct isozymes of 11-beta-HSD have been cloned and characterized: 11β-HSD1 (also known as 11-beta-HSD type 1, 11betaHSD1, HSD11B1, HDL, and HSD11L) and 11β-HSD2. 11β-HSD1 is a bi-directional oxidoreductase that regenerates active cortisol from inactive 11-keto forms, whereas 11β-HSD2 is a unidirectional dehydrogenase that inactivates biologically active cortisol by converting it into cortisone.

The two isoforms are expressed in a distinct tissue-specific fashion, consistent with the differences in their physiological roles. 11β-HSD1 is widely distributed in rat and human tissues; expression of the enzyme and corresponding mRNA have been detected in human liver, adipose tissue, lung, testis, bone and ciliary epithelium. In adipose tissue, increased cortisol concentrations stimulate adipocyte differentiation and may play a role in promoting visceral obesity. In the eye, 11β-HSD1 may regulate intraocular pressure and may contribute to glaucoma; some data suggest that inhibition of 11β-HSD1 may cause a drop in intraocular pressure in patients with intraocular hypertension (Kotelevstev et al. (1997), Proc. Natl. Acad. Sci. USA 94(26):14924-9). Although 11β-HSD1 catalyzes both 11-beta-dehydrogenation and the reverse 11-oxoreduction reaction, 11β-HSD1 acts predominantly as a NADPH-dependent oxoreductase in intact cells and tissues, catalyzing the formation of active cortisol from inert cortisone (Low et al. (1994) J. Mol. Endocrin. 13: 167-174). In contradistinction, 11β-HSD2 expression is found mainly in mineralocorticoid target tissues such as kidney (cortex and medulla), placenta, sigmoid and rectal colon, salivary gland and colonic epithelial cell lines. 11β-HSD2 acts as an NAD-dependent dehydrogenase catalyzing the inactivation of cortisol to cortisone (Albiston et al. (1994) Mol. Cell. Endocrin. 105: R11-R17), and has been shown to protect the MR from glucocorticoid excess (e.g., high levels of receptor-active cortisol) (Blum, et al. (2003) Prog. Nucl. Acid Res. Mol. Biol. 75:173-216).

Mutations in either the 11β-HSD1 or the 11β-HSD2 genes result in human pathology. For example, individuals with mutations in 11β-HSD2 are deficient in this cortisol-inactivation activity and, as a result, present with a syndrome of apparent mineralocorticoid excess (also referred to as 'SAME') characterized by hypertension, hypokalemia, and sodium retention (Edwards et al. (1988) Lancet 2: 986-989; Wilson et al. (1998) Proc. Natl. Acad. Sci. 95: 10200-10205). Similarly, mutations in 11β-HSD1 and in the gene encoding a co-localized NADPH-generating enzyme, hexose 6-phosphate dehydrogenase (H6PD), can result in cortisone reductase deficiency (CRD); these individuals present with ACTH-mediated androgen excess (hirsutism, menstrual irregularity, hyperandrogenism), a phenotype resembling polycystic ovary syndrome (PCOS) (Draper et al. (2003) Nat. Genet. 34: 434-439).

Notably, disruption of homeostasis in the HPA axis by either deficient or excess secretion or action results in Cushing's syndrome or Addison's disease, respectively (Miller and Chrousos (2001) Endocrinology and Metabolism, eds. Felig and Frohman (McGraw-Hill, New York), 4$^{th}$ Ed.: 387-524). Patients with Cushing's syndrome or receiving glucocorticoid therapy develop reversible visceral fat obesity. The phenotype of Cushing's syndrome patients closely resembles that of Reaven's metabolic syndrome (also known as Syndrome X or insulin resistance syndrome), the symptoms of which include visceral obesity, glucose intolerance, insulin resistance, hypertension, type 2 diabetes and hyperlipidemia (Reaven (1993) Ann. Rev. Med. 44: 121-131). Although the role of glucocorticoids in human obesity is not fully characterized, there is mounting evidence that 11β-HSD1 activity plays an important role in obesity and metabolic syndrome (Bujalska et al. (1997) Lancet 349: 1210-1213); (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Data from studies in mouse transgenic models supports the hypothesis that adipocyte 11β-HSD1 activity plays a central role in visceral obesity and metabolic syndrome (Alberts et al. (2002) Diabetologia. 45(11): 1526-32). Over-expression in adipose tissue of 11β-HSD1 under the control of the aP2 promoter in transgenic mice produced a phenotype remarkably similar to human metabolic syndrome (Masuzaki et al. (2001) Science 294: 2166-2170; Masuzaki et al. (2003) J. Clinical Invest. 112: 83-90). Moreover, the increased activity of 11β-HSD1 in these mice is very similar to that observed in human obesity (Rask et al. (2001) J. Clin. Endocrinol. Metab. 86: 1418-1421). In addition, data from studies with 11β-HSD1-deficient mice produced by homologous recombination demonstrate that the loss of 11β-HSD1 leads to an increase in insulin sensitivity and glucose tolerance due to a tissue-specific deficiency in active glucocorticoid levels (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938).

The published data supports the hypothesis that increased expression of 11β-HSD1 contributes to increased local conversion of cortisone to cortisol in adipose tissue and hence that 11β-HSD1 plays a role in the pathogenesis of central obesity and the appearance of the metabolic syndrome in humans (Engeli, et al., (2004) Obes. Res. 12: 9-17). Therefore, 11β-HSD1 is a promising pharmaceutical target for the treatment of the metabolic syndrome (Masuzaki, et al., (2003) Curr. Drug Targets Immune Endocr. Metabol. Disord. 3: 255-62). Furthermore, inhibition of 11β-HSD1 activity may prove beneficial in treating numerous glucocorticoid-related disorders. For example, 11β-HSD1 inhibitors could be effective in combating obesity and/or aspects of the metabolic syndrome cluster, including glucose intolerance, insulin resistance, hyperglycemia, hypertension, and/or hyperlipidemia (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). In addition, inhibition of 11β-HSD1 activity may have beneficial effects on the pancreas, including the enhancement of glucose-stimulated insulin release (Billaudel and Sutter (1979) Horm. Metab. Res. 11: 555-560; Ogawa et al. (1992) J. Clin. Invest. 90: 497-504; Davani et al. (2000) J. Biol. Chem. 275: 34841-34844).

Furthermore, given that inter-individual differences in general cognitive function have been linked to variability in the long-term exposure to glucocorticoids (Lupien et al. (1998) Nat. Neurosci. 1: 69-73) and dysregulation of the HPA axis resulting in chronic exposure to glucocorticoid excess in certain brain subregions has been theorized to contribute to the decline of cognitive function (McEwen and Sapolsky (1995) Curr. Opin. Neurobiol. 5: 205-216), one might predict that inhibition of 11β-HSD1 could reduce exposure to glucocorticoids in the brain and thereby protect against deleterious glucocorticoid effects on neuronal function, including cognitive impairment, dementia, and/or depression. Notably, it is known that stress and glucocorticoids influence cognitive function (de Quervain et al. (1998) Nature 394: 787-790); and it has been shown that 11β-HSD1, through its control of glucocorticoid action in the brain, may have effects on neurotoxicity (Rajan et al. (1996) Neuroscience 16: 65-70; Seckl (2000) Neuroendocrinol. 18:49-99).

There is also evidence that glucocorticoids and 11β-HSD1 play a role in regulation of in intra-ocular pressure (IOP) (Stokes et al. (2000) Invest. Opthalmol. Vis. Sci. 41: 1629-1683; Rauz et al. (2001) Invest. Opthalmol. Vis. Sci. 42: 2037-2042); if left untreated, elevated IOP can lead to partial visual field loss and eventually blindness. Thus, inhibition of 11β-HSD1 in the eye could reduce local glucocorticoid concentrations and IOP, and 11β-HSD1 hence could potentially be used to treat glaucoma and other visual disorders.

Transgenic aP2-11βHSD1 mice exhibit high arterial blood pressure and have increased sensitivity to dietary salt. Moreover, plasma angiotensinogen levels are elevated in the transgenic mice, as are angiotensin II and aldosterone; and treatment of the mice with an angiotensin II antagonist alleviates the hypertension (Masuzaki et al. (2003) J. Clinical Invest. 112: 83-90). This suggests that hypertension may be caused or exacerbated by 11β-HSD1 activity. Thus, 11β-HSD1 inhibitors may be useful for treatment of hypertension and hypertension-related cardiovascular disorders. Inhibition of 11β-HSD1 in mature adipocytes is also expected to attenuate secretion of plasminogen activator inhibitor 1 (PAI-1), which is an independent cardiovascular risk factor (Halleux et al. (1999) J. Clin. Endocrinol. Metabl. 84: 4097-4105).

Glucocorticoids can have adverse effects on skeletal tissues; and prolonged exposure to even moderate glucocorticoid doses can result in osteoporosis (Cannalis (1996) J. Clin. Endocrinol. Metab. 81: 3441-3447). In addition, 11β-HSD1 has been shown to be present in cultures of human primary osteoblasts as well as cells from adult bone (Cooper et al. (2000) Bone 27: 375-381), and the 11β-HSD1 inhibitor carbenoxolone has been shown to attenuate the negative effects of glucocorticoids on bone nodule formation (Bellows et al. (1998) Bone 23: 119-125). Thus, inhibition of 11β-HSD1 is predicted to decrease the local glucocorticoid concentration within osteoblasts and osteoclasts, thereby producing beneficial effects in various forms of bone disease, including osteoporosis.

11β-HSD1 inhibitors may also be useful for immunomodulation. Although glucocorticoids are perceived to suppress the immune system, in actuality, there is a complex, dynamic interaction between the HPA axis and the immune system (Rook (1999) Baillier's Clin. Endocrinol. Metabl. 13: 576-581). Glucocorticoids play a role in modulating the balance between cell-mediated and humoral immune response, with high glucocorticoid activity normally associated with a humoral response. Inhibition of 11β-HSD1 therefore can be used a means of shifting the immune response towards a cell-mediated response. Certain disease states, such as tuberculosis, leprosy (Hansen's disease) and psoriasis, trigger immune responses that are biased towards a humoral response whereas the more effective immune response may be a cell-mediated response. Hence, 11β-HSD1 inhibitors may be useful for treating such diseases.

It has been reported that glucocorticoids inhibit wound healing, especially in diabetic patients with ulcers (Bitar et al. (1999) J. Surg. Res. 82: 234-243; Bitar et al. (1999) Surgery 125: 594-601; Bitar (2000) Surgery 127: 687-695; Bitar (1998) Am. J. Pathol. 152: 547-554). Patients that exhibit impaired glucose tolerance and/or type 2 diabetes often also have impaired wound healing. Glucocorticoids have been shown to increase the risk of infection and delay wound healing (Anstead (1998) Adv. Wound Care 11:277-285). Moreover, there is a correlation between elevated levels of cortisol in wound fluid and non-healing wounds (EP Patent App. No. 0 902 288). Recent published patent applications have suggested that certain 11β-HSD1 inhibitors may be useful for promoting wound healing (PCT/US2006/043, 951).

As evidenced herein, there is a continuing need for new and improved drugs that inhibit 11β-HSD1. The novel compounds of the instant invention are effective inhibitors of 11β-HSD1.

SUMMARY OF THE INVENTION

It has now been found that compounds of Formula I or pharmaceutically acceptable salts or prodrugs thereof, are effective inhibitors of 11β-HSD1. In a first embodiment of the invention, Formula I and its constituent members are defined herein as follows:

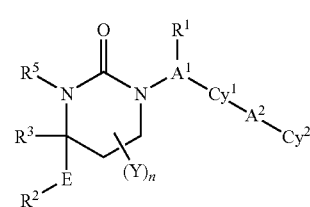

wherein:
$R^1$ is (a) absent or (b) selected from $(C_1-C_6)$alkyl, $(C_2-C_6)$alkenyl, $(C_2-C_6)$alkynyl, $(C_1-C_3)$alkoxy$(C_1-C_3)$alkoxy, or $(C_1-C_3)$alkoxy$(C_1-C_3)$alkyl and is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, aryl, cycloalkyl, heterocyclyl, heteroaryl, arylamino and heteroarylamino;

$A^1$ is (a) a bond, or (b) $(C_1-C_3)$alkylene, $CH_2CH_2O$, wherein the oxygen is attached to $Cy^1$, or $CH_2C(=O)$, wherein the carbonyl carbon is attached to $Cy^1$;

$Cy^1$ is aryl, heteroaryl, monocyclic cycloalkyl or monocyclic heterocyclyl and is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, $\{(C_3-C_6)$cycloalkyl$\}\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl and di$(C_3-C_6)$cycloalkylaminocarbonyl$(C_1-C_6)$alkyl;

$A^2$ is (a) a bond, O, S or $NR^4$; or (b) $(C_1-C_3)$alkylene or $(C_1-C_2)$alkyleneoxy, each of which is optionally substituted with 1 to 4 groups independently selected from methyl, ethyl, trifluoromethyl or oxo;

$Cy^2$ is (a) hydrogen or (b) aryl, heteroaryl, cycloalkyl or heterocyclyl and is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, $\{(C_3-C_6)$cycloalkyl$\}\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl and di$(C_3-C_6)$cycloalkylaminocarbonyl$(C_1-C_6)$alkyl;

Y is $(C_1-C_6)$alkyl or halo$(C_1-C_6)$alkyl;

n is 0, 1 or 2;

E is (a) a bond or (b) $(C_1-C_3)$alkylene or $(C_1-C_2)$alkylenyloxy, wherein the 0 is attached to $R^2$, each of which is optionally substituted with 1 to 4 groups independently selected from methyl, ethyl, trifluoromethyl or oxo;

$R^2$ is $(C_1-C_6)$alkyl, aryl, heteroaryl, cycloalkyl or heterocyclyl and is optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$ cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, $\{(C_3-C_6)$cycloalkyl$\}\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl and di$(C_3-C_6)$cycloalkylaminocarbonyl$(C_1-C_6)$alkyl;

$R^3$ is selected from $(C_1-C_6)$alkyl, $(C_2-C_6)$alkenyl, $(C_2-C_6)$alkynyl, $(C_3-C_6)$cycloalkyl$(C_1-C_4)$alkyl, $(C_1-C_3)$alkoxy$(C_1-C_3)$alkoxy, or $(C_1-C_3)$alkoxy$(C_1-C_3)$alkyl and is optionally substituted with up to four groups independently selected from fluorine, cyano, oxo, $R^4$, $R^4O—$, $(R^4)_2N—$, $R^4O_2C—$, $R^4C(=O)O—$, $R^4S$, $R^4S(=O)—$, $R^4S(=O)_2—$, $R^4C(=O)NR^4—$, $(R^4)_2NC(=O)—$, $(R^4)_2NC(=O)O—$, $(R^4)_2NC(=O)NR^4—$, $R^4OC(=O)NR^4—$, $(R^4)_2NC(=NCN)N(R^4O)_2P(=O)O—$, $(R^4O)_2P(=O)NR^4—$, $R^4OS(=O)_2NR^4—$, $(R^4)_2NS(=O)_2O—$, $(R^4)_2NS(=O)_2NR^4—$, $R^4S(=O)_2NHC(=O)—$, $R^4S(=O)_2NHC(=O)O—$, $R^4S(=O)_2NHC(=O)NR^4—$, $R^4OS(=O)_2NHC(=O)—$, $R^4OS(=O)_2NHC(=O)O—$, $R^4OS(=O)_2NHC(=O)NR^4—$, $(R^4)_2NS(=O)_2NHC(=O)—$, $(R^4)_2NS(=O)_2NHC(=O)O—$, $(R^4)_2NS(=O)_2NHC(=O)NR^4—$, $R^4C(=O)NHS(=O)_2—$, $R^4C(=O)NHS(=O)_2O—$, $R^4C(=O)NHS(=O)_2NR^4—$, $R^4OC(=O)NHS(=O)_2—$, $R^4OC(=O)NHS(=O)_2O—$, $R^4OC(=O)NHS(=O)_2NR^4—$, $(R^4)_2NC(=O)NHS(=O)_2—$, $(R^4)_2NC(=O)NHS(=O)_2O—$, $(R^4)_2NC(=O)NHS(=O)_2NR^4—$, spirocycloalkyl; heterocyclyl (which in turn may be optionally substituted with alkyl, haloalkyl, halogen or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CON H_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

$R^4$ is independently selected from H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl; and $R^5$ is H, $(C_1-C_6)$alkyl, halo$(C_1-C_6)$alkyl, hydroxy$(C_1-C_6)$alkyl;

or a pharmaceutically acceptable salt, enantiomer or diastereomer thereof.

In a second embodiment of the invention, Formula I and its constituent members are defined herein as follows:

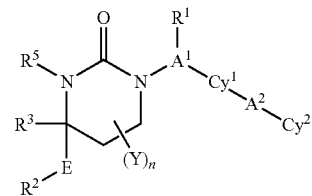

I $R^1$ is (a) absent or (b) is selected from $(C_1-C_6)$alkyl, $(C_2-C_6)$alkenyl, $(C_2-C_6)$alkynyl or $(C_1-C_3)$alkoxy$(C_1-C_3)$alkyl, wherein each is optionally substituted with up to four groups independently selected from fluorine, cyano, oxo, $R^4$, $R^4O—$, $(R^4)_2N—$, $R^4O_2C—$, $R^4S$, $R^4S(=O)—$, $R^4S(=O)_2—$, $R^4C(=O)NR^4—$, $(R^4)_2NC(=O)—$, $(R^4)_2NC(=O)O—$, $(R^4)_2NC(=O)NR^4—$, $R^4OC(=O)NR^4—$, $(R^4)_2NC(=NCN)NR^4—$, $(R^4O)_2P(=O)O—$, $(R^4O)_2P(=O)NR^4—$, $R^4OS(=O)_2NR^4—$, $(R^4)_2NS(=O)_2O—$, $(R^4)_2NS(=O)_2NR^4—$, $R^4S(=O)_2NR^4—$, $R^4S(=O)_2NHC(=O)—$, $R^4S(=O)_2NHC(=O)O—$, $R^4S(=O)_2NHC(=O)NR^4—$, $R^4OS(=O)_2NHC(=O)—$, $R^4OS(=O)_2NHC(=O)O—$, $R^4OS(=O)_2NHC(=O)NR^4—$, $(R^4)_2NS(=O)_2NHC(=O)—$, $(R^4)_2NS(=O)_2NHC(=O)O—$, $(R^4)_2NS(=O)_2NHC(=O)NR^4—$, $R^4C(=O)NHS(=O)_2—$, $R^4C(=O)NHS(=O)_2O—$, $R^4C(=O)NHS(=O)_2NR^4—$, $R^4OC(=O)NHS(=O)_2—$, $R^4OC(=O)NHS(=O)_2O—$, $R^4OC(=O)NHS(=O)_2NR^4—$, $(R^4)_2NC(=O)NHS(=O)_2—$, $(R^4)_2NC(=O)NHS(=O)_2O—$, $(R^4)_2NC(=O)NHS(=O)_2NR^4—$, aryl, cycloalkyl, heterocyclyl, heteroaryl, arylamino and heteroarylamino;

$A^1$ is (a) a bond, or (b) $(C_1-C_3)$alkylene, $CH_2CH_2O$, wherein the oxygen is attached to $Cy^1$, or $CH_2C(=O)$, wherein the carbonyl carbon is attached to $Cy^1$;

$Cy^1$ is aryl, heteroaryl, monocyclic cycloalkyl or monocyclic heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$ cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, $(C_1-C_6)$alkoxy$(C_1-C_6)$alkyl, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;

$A^2$ is (a) a bond, O, S or $NR^4$; or (b) $(C_1-C_3)$alkylene or $(C_1-C_2)$alkyleneoxy, each of which is optionally substituted with 1 to 4 groups independently selected from methyl, ethyl, trifluoromethyl or oxo;

$Cy^2$ is (a) hydrogen or (b) aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, $(C_1-C_6)$alkoxy$(C_1-C_6)$alkyl, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;

Y is $(C_1-C_6)$alkyl or halo$(C_1-C_6)$alkyl;

n is 0, 1 or 2;

E is (a) a bond or (b) $(C_1-C_3)$alkylene or $(C_1-C_2)$alkylenyloxy, wherein the 0 is attached to $R^2$, each of which is optionally substituted with 1 to 4 groups independently selected from methyl, ethyl, trifluoromethyl or oxo;

$R^2$ is $(C_1-C_6)$alkyl, aryl, heteroaryl, cycloalkyl or heterocyclyl, wherein each is optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;

$R^3$ is selected from $(C_1-C_6)$alkyl, $(C_2-C_6)$alkenyl, $(C_2-C_6)$alkynyl and $(C_1-C_3)$alkoxy$(C_1-C_3)$alkyl, wherein each is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$, $R^4S(=O)_2NR^4$—, $R^4S(=O)_2NHC(=O)$—, $R^4S(=O)_2NHC(=O)$—, $R^4S(=O)_2NHC(=O)NR^4$, $R^4OS(=O)_2NHC(=O)$—, $R^4OS(=O)_2NHC(=O)O$—, $R^4OS(=O)_2NHC(=O)NR^4$, $(R^4)_2NS(=O)_2NHC(=O)$—, $(R^4)_2NS(=O)_2NHC(=O)O$—, $(R^4)_2NS(=O)_2NHC(=O)NR^4$, $R^4C(=O)NHS(=O)_2$—, $R^4C(=O)NHS(=O)_2O$—, $R^4C(=O)NHS(=O)_2NR^4$, $R^4OC(=O)NHS(=O)_2$—, $R^4OC(=O)NHS(=O)_2O$—, $R^4OC(=O)NHS(=O)_2NR^4$, $(R^4)_2NC(=O)NHS(=O)_2$—, $(R^4)_2NC(=O)NHS(=O)_2O$—, $(R^4)_2NC(=O)NHS(=O)_2NR^4$, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

$R^4$ is independently selected from H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl;

$R^5$ is H, $(C_1-C_6)$alkyl, halo$(C_1-C_6)$alkyl, or hydroxy$(C_1-C_6)$alkyl;

or a pharmaceutically acceptable salt, enantiomer or diastereomer thereof.

Another embodiment of the invention is a compound of Formulas I, Ia, Ib, Ic, Id, Ie, If, Ig, Ih, Ij, Ik, Il$^{1-3}$, Im$^{1-3}$, In$^{1-3}$, Io$^{1-2}$, Ip$^{1-6}$, Iq$^{1-6}$, Ir$^{1-6}$ and Is$^{1-2}$ or a pharmaceutically acceptable salt, enantiomer or diastereomer thereof, wherein any one of the following provisos apply or any combination thereof:

Proviso 1: If -Cy$^1$-A$_2$-Cy$_2$ is one of the following groups:

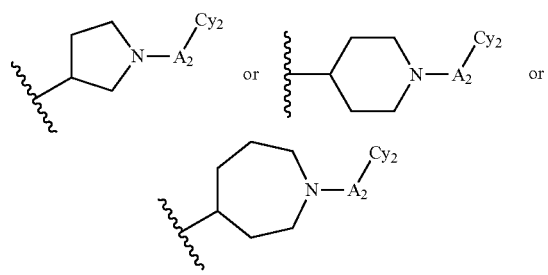

and if the nitrogen-containing heterocycle represented by -Cy$^1$ is unsubstituted or substituted with one or two $(C_1-C_4)$ alkyl groups; and $R^3$ is unsubstituted $C_1-C_6$)alkyl; then $A^1$ cannot be a bond.

Proviso 2: If A$_1$ is a C$_2$-C$_3$ alkylene, then -Cy$^1$-A$_2$-Cy$_2$ cannot be

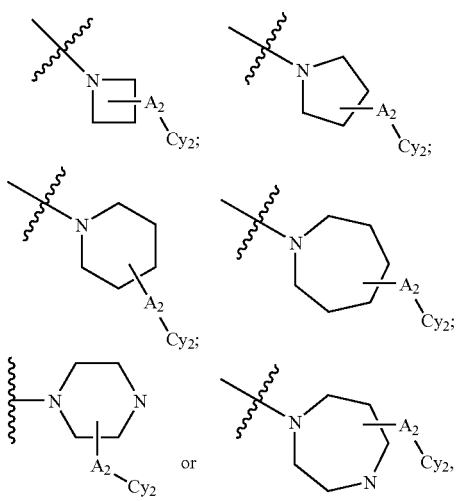

wherein the nitrogen-containing heterocycle represented by Cy$^1$ is optionally substituted.

Proviso 3: When A$^1$ is —CH$_2$— and Cy$^1$ is optionally substituted phenyl, A$^2$ is a bond and Cy$_2$ is H, then Cy$^1$ is substituted with a group other than ortho —COOH.

Proviso 4: (i) when R$^3$ or E-R$^2$ is C$_1$-C$_4$ alkyl, it is substituted, but not with C$_1$-C$_2$ alkoxy or halogen; or
(ii) when E-R$^2$ is phenylmethyl, it is substituted, but not with C$_1$-C$_2$ alkoxy or halogen.

Proviso 5: If —R$^3$ is C$_1$-C$_4$ alkyl substituted with halogen or C$_1$-C$_2$ alkoxy; E-R$^2$ is C$_1$-C$_4$ alkyl or benzyl substituted with halogen or C$_1$-C$_2$ alkoxy, and n is not zero, and Y is alpha to —R$^3$, Y cannot be $(C_1-C_3)$alkyl.

Proviso 6: If R$^3$ is alkoxyalkyl substituted with heteroaryl, then E-R$^2$ cannot be optionally substituted heteroaryl or phenyl.

Proviso 7: If A$_1$ is a bond; Cy$_1$ is a C$_5$-C$_7$ aryl; A$_2$ is —CH$_2$—; and Cy$_2$ is an optionally substituted

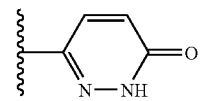

fused to an optionally substituted aromatic ring, and R$^3$ is C$_1$-C$_6$ alkyl, then E-R$^2$ cannot be an optionally substituted C$_1$-C$_6$ alkyl or C$_5$-C$_6$ aryl.

Proviso 8: If R$^5$ is H, or $(C_1-C_5)$alkyl, or halo$(C_1-C_5)$alkyl; E is a bond or C$_1$alkylene, R$_2$ is aryl, heteroaryl or heterocyclyl, A$^1$ is $(C_1)$alkylene, R$^3$ is optionally fluorinated $(C_1-C_5)$alkyl, $(C_2-C_5)$alkenyl or $(C_2-C_6)$alkynyl and Cy$^1$ is optionally substituted phenyl, then Cy$^1$ is not substituted at the ortho position by optionally substituted aryl, heteroaryl, heterocyclyl or cycloalkyl.

Proviso 9: If A$_1$ is a bond; Cy$_1$ is aryl; E-R$^2$ is alkyl or aryl, then R$^3$ can not be alkyl.

Proviso 10: If (a) A is C$_1$-C$_5$ alkyl (b) R$^3$ is methyl or vinyl (c) then E-R$^2$ is not methyl or phenyl.

Another embodiment of the present invention is a compound of Formulas I, Ia, Ib, Ic, Id, Ie, If, Ig, Ih, Ij, Ik, Il$^{1-3}$. Im$^{1-3}$, In$^{1-3}$, Io$^{1-2}$, Ip$^{1-6}$, Iq$^{1-6}$, Ir$^{1-6}$ and Is$^{1-2}$, or a pharmaceutically acceptable salt, enantiomer of diastereomer thereof, wherein all of the above Provisos apply. Yet another embodiment of the present invention is a compound of Formula I, Ia, Ib, Ic, Id, Ie, If, Ig, Ih, Ij, Ik, Il$^{1-3}$. Im$^{1-3}$, In$^{1-3}$, Io$^{1-2}$, Ip$^{1-6}$, Iq$^{1-6}$, Ir$^{1-6}$ and Is$^{1-2}$, or a pharmaceutically acceptable salt, enantiomer of diastereomer thereof, wherein the above Provisos 1, 2, 3, 7 or 10 apply. Yet another embodiment of the present invention is a compound of Formula I, Ia, Ib, Ic, Id, Ie, If, Ig, Ih, Ij, Ik, Il$^{1-3}$. Im$^{1-3}$, In$^{1-3}$, Io$^{1-2}$, Ip$^{1-6}$, Iq$^{1-6}$, Ir$^{1-6}$ and Is$^{1-2}$ or a pharmaceutically acceptable salt, enantiomer of diastereomer thereof, wherein the above Provisos 4, 5, 6, 8 and 9 apply. Yet another embodiment of the present invention is a compound of Formula I, Ia, Ib, Ic, Id, Ie, If, Ig, Ih, Ij, Ik, Il$^{1-3}$. Im$^{1-3}$, In$^{1-3}$, Io$^{1-2}$, Ip$^{1-6}$, Iq$^{1-6}$, Ir$^{1-6}$ and Is$^{1-2}$ or a pharmaceutically acceptable salt, pharmaceutically acceptable salt, enantiomer of diastereomer thereof, wherein the above Provisos 6 and 8 apply.

Another embodiment of the present invention is a pharmaceutical composition comprising: i) a pharmaceutically acceptable carrier or diluent; and ii) a compound of Formula I, Ia, Ib, Ic, Id, Ie, If, Ig, Ih, Ij, Ik, Il$^{1-3}$. Im$^{1-3}$, In$^{1-3}$, Io$^{1-2}$, Ip$^{1-6}$, Iq$^{1-6}$, Ir$^{1-6}$ and Is$^{1-2}$ or a pharmaceutically acceptable salt, enantiomer of diastereomer thereof, wherein the above Provisos 1, 2, 4, 5, 6, 7, 8 and 10 apply.

Another embodiment of the present invention is a pharmaceutical composition comprising a pharmaceutically acceptable carrier or diluent; and ii) a compound of Formulas I, Ia, Ib, Ic, Id, Ie, If, Ig, Ih, Ij, Ik, Il$^{1-3}$. Im$^{1-3}$, In$^{1-3}$, Io$^{1-2}$, Ip$^{1-6}$, Iq$^{1-6}$, Ir$^{1-6}$ and Is$^{1-2}$, or a pharmaceutically acceptable salt, enantiomer of diastereomer thereof, wherein Provisos 2, 6, and 8 applies.

Another embodiment of the present invention is a pharmaceutical composition comprising a pharmaceutically acceptable carrier or diluent; and ii) a compound of Formulas I, Ia, Ib, Ic, Id, Ie, If, Ig, Ih, Ij, Ik, Il$^{1-3}$. Im$^{1-3}$, In$^{1-3}$, Io$^{1-2}$, Ip$^{1-6}$, Iq$^{1-6}$, Ir$^{1-6}$ and Is$^{1-2}$, or a pharmaceutically acceptable salt, enantiomer of diastereomer thereof, wherein Proviso 8 applies.

Another embodiment of the invention is a method of inhibiting 11β-HSD1 activity comprising the step of administering to a mammal in need of such treatment an effective amount of a compound of Formulas I, Ia, Ib, Ic, Id, Ie, If, Ig, Ih, Ij, Ik, Il$^{1-3}$. Im$^{1-3}$, In$^{1-3}$, Io$^{1-2}$, Ip$^{1-6}$, Iq$^{1-6}$, Ir$^{1-6}$ and Is$^{1-2}$, or a pharmaceutically acceptable salt, enantiomer or diastereomer thereof.

Another embodiment of the invention is a method of treating a subject with a disease associated with the activity or expression of 11β-HSD1, comprising the step of administering to the subject an effective amount of a compound of Formulas I, Ia, Ib, Ic, Id, Ie, If, Ig, Ih, Ij, Ik, Il$^{1-3}$. Im$^{1-3}$, In$^{1-3}$, Io$^{1-2}$, Ip$^{1-6}$, Iq$^{1-6}$, Ir$^{1-6}$ and Is$^{1-2}$, or a pharmaceutically acceptable salt, enantiomer or diastereomer thereof.

Another embodiment of the invention is the use of a compound of Formulas I, Ia, Ib, Ic, Id, Ie, If, Ig, Ih, Ij, Ik, Il$^{1-3}$. Im$^{1-3}$, In$^{1-3}$, Io$^{1-2}$, Ip$^{1-6}$, Iq$^{1-6}$, Ir$^{1-6}$ and Is$^{1-2}$, or a pharmaceutically acceptable salt, enantiomer or diastereomer thereof for the manufacture of a medicament for inhibiting 11β-HSD1 activity in a mammal in need of such treatment.

Another embodiment of the invention is the use of a compound of Formulas I, Ia, Ib, Ic, Id, Ie, If, Ig, Ih, Ij, Ik, Il$^{1-3}$. Im$^{1-3}$, In$^{1-3}$, Io$^{1-2}$, Ip$^{1-6}$, Iq$^{1-6}$, Ir$^{1-6}$ and Is$^{1-2}$, or a pharmaceutically acceptable salt, enantiomer or diastereomer thereof for the manufacture of a medicament for treating a subject with a disease associated with the activity or expression of 11β-HSD1

Another embodiment of the invention is a compound of Formulas I, Ia, Ib, Ic, Id, Ie, If, Ig, Ih, Ij, Ik, Il$^{1-3}$. Im$^{1-3}$, In$^{1-3}$, Io$^{1-2}$, Ip$^{1-6}$, Iq$^{1-6}$, Ir$^{1-6}$ and Is$^{1-2}$, or a pharmaceutically acceptable salt, enantiomer or diastereomer thereof for use in inhibiting 11β-HSD1 activity in a mammal in need of such treatment.

Another embodiment of the invention is a compound of Formulas I, Ia, Ib, Ic, Id, Ie, If, Ig, Ih, Ij, Ik, Il$^{1-3}$. Im$^{1-3}$, In$^{1-3}$, Io$^{1-2}$, Ip$^{1-6}$, Iq$^{1-6}$, Ir$^{1-6}$ and Is$^{1-2}$, or a pharmaceutically acceptable salt, enantiomer or diastereomer thereof for use in for treating a subject with a disease associated with the activity or expression of 11β-HSD1.

In one embodiment, Provisos 2 and/or 6 applies when the subject is being treated to lower intra-ocular pressure.

In one embodiment, Provisos 6 and/or 8 applies when the subject is being treated for obesity.

In one embodiment, Proviso 8 applies when the subject is being treated for atherosclerosis, dyslipidemia, or cardiovascular disorders.

DETAILED DESCRIPTION OF THE INVENTION

A third embodiment of the invention is a compound of Formula I or any one of Formulas Ia-f wherein the values are as defined for Formula I above in the first or second embodiment; and Cy$^1$ (For Formulas I and Ia-e) is aryl, heteroaryl, monocyclic cycloalkyl or heterocyclyl, which contains 1 to 2 heteroatoms independently selected from O and S, wherein the aryl, heteroaryl, cycloalkyl or heterocyclyl is optionally substituted with 1 to 4 groups independently selected from fluorine, chlorine, bromine, iodine, cyano, nitro, amino, hydroxy, ($C_1$-$C_6$)alkyl, hydroxy($C_1$-$C_6$)alkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_4$-$C_7$)cycloalkylalkyl, ($C_1$-$C_6$)alkoxy, ($C_4$-$C_7$)cycloalkylalkoxy, halo($C_1$-$C_6$)alkoxy, halo($C_4$-$C_7$)cycloalkylalkoxy, ($C_1$-$C_6$)alkylthio, ($C_3$-$C_6$)cycloalkylhio, ($C_4$-$C_7$)cycloalkylalkylthio, halo($C_1$-$C_6$)alkylthio, halo($C_3$-$C_6$)cycloalkylhio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl and ($C_1$-$C_6$)alkylcarbonyl;

A$^2$ (For Formulas I and Ia-e) is (a) a bond, O, S or NR$^4$; or (b) ($C_1$-$C_3$)alkylene or ($C_1$-$C_2$)alkyleneoxy, each of which is optionally substituted with 1 to 4 groups independently selected from methyl, ethyl, trifluoromethyl or oxo, wherein A$_2$ is attached at least two ring atoms away from A$^1$;

Cy$^2$ (For Formulas I and Ia-e) is (a) hydrogen or (b) aryl, cycloalkyl, heterocyclyl or a heteroaryl selected from 2- or 3-thienyl, 2- or 3-furanyl, 2- or 3-pyrrolyl, 2-, 3-, or 4-pyridyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, 5-, 6-, 7- or 8-quinazolinyl, 2-, 3-, 5-, 6-, 7- or 8-quinoxalinyl, 2-, 3-, 4-, 5-, 6-, 7- or 8-quinolinyl, 1-, 3-, 4-, 5-, 6-, 7- or 8-isoquinolinyl, 2-, 4-, or 5-thiazolyl, 2-, 3-, 4-, or 5-pyrazolyl, 2-, 3-, 4-, or 5-imidazolyl, wherein each is optionally substituted with 1 to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylhio, ($C_4$-$C_7$)cycloalkylalkylthio, halo($C_1$-$C_6$)alkylthio, halo($C_3$-$C_6$)cycloalkylhio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl and ($C_1$-$C_6$)alkylcarbonyl;

In one aspect of the invention, the heterocyclyl represented by $Cy^2$ is other than optionally substituted thiazolidine-2,4-dionyl.

$R^2$ (For Formulas I, Ia-c, and Ie-f) is aryl, heteroaryl, cycloalkyl or heterocyclyl, wherein each is optionally substituted with up to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylthio, ($C_4$-$C_7$)cycloalkylalkylthio, halo($C_1$-$C_6$)alkylthio, halo($C_3$-$C_6$)cycloalkylthio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl and ($C_1$-$C_6$)alkylcarbonyl; or oxo; or ($C_1$-$C_6$)alkyl substituted with up to 4 groups independently selected from cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylhio, ($C_4$-$C_7$)cycloalkylalkylthio, halo($C_1$-$C_6$)alkylthio, halo($C_3$-$C_6$)cycloalkylhio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl and ($C_1$-$C_6$)alkylcarbonyl;

provided that if E-$R^2$ is benzyl then it is not an unsubstituted benzyl or a benzyl substituted with alkoxy or halogen;

$R^3$ (For Formulas I and Ia-f) is selected from, ($C_2$-$C_6$)alkenyl, ($C_2$-$C_6$)alkynyl and ($C_1$-$C_3$)alkoxy($C_1$-$C_3$)alkyl, wherein each is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, heterocyclyl (which in turn may be optionally substituted with alkyl, haloalkyl or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); or is, ($C_1$-$C_6$)alkyl substituted with up to four groups independently selected from cyano, oxo, $R^4$, $(R^4)_2N$—, $R^4O_2O$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, heterocyclyl (which in turn may be optionally substituted with alkyl, haloalkyl or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo).

A fourth embodiment of the invention is a compound of Formula I or any one of Formulas Ia-f wherein the values are as defined for Formula I above in the first, second or third embodiment; and $R^3$ is selected from $(C_1-C_6)$alkyl, $(C_2-C_6)$alkenyl, $(C_2-C_6)$alkynyl, or $(C_1-C_3)$alkoxy$(C_1-C_3)$alkyl and wherein each is substituted with one to four groups independently selected from cyano, oxo, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4SO_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$— and $(R^4)_2NC(=O)NHS(=O)_2NR^4$—.

A fifth embodiment of the invention is a compound of Formula I or any one of Formulas Ia-f wherein the values are as defined for Formula I above in the first, second, third or fourth embodiment and $R^1$ (for Formulas I and Id) is absent or is methyl or ethyl;

$A^1$ (for Formulas I and Id) is a bond or $CH_2$ or if $R^1$ is present, then $A^1$ is CH;

$Cy^1$ (for Formulas I and Ia-e) is phenyl, cyclopropyl, cyclohexyl, pyrrolidinyl, pyridyl, N-oxo-pyridyl, thiazolyl or pyrimidinyl optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, t-butoxycarbonyl, hydroxy, hydroxymethyl, 2-hydroxyethyl, 2-hydroxy-2-propyl, methoxymethyl, methylsulfonyl and methylsulfonylamino;

$A^2$ (for Formulas I and Ia-e) is a bond, O, $OCH_2CO$ or C=O;

$Cy^2$ (for Formulas I and Ia-e) is (a) hydrogen or (b) phenyl, thienyl, pyridyl, N-oxo-pyridyl, cyclopropyl, piperidinyl, piperazinyl, morpholinyl, thiazolyl, oxadiazolyl, thiadiazolyl, pyrazolyl, S,S-dioxothiazinyl, 2-oxo-1,2-dihydropyridyl optionally substituted by 1 to 4 groups independently selected from halo, hydroxy, methoxy, hydroxymethyl, methoxycarbonyl, amino, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylaminosulfonyl, pyrrolidine-1-sulfonyl, methylsulfonylaminomethyl, tetrazolyl, methyl, trifluoromethyl, acetyl, 2-hydroxyethyl and 1-aminoethyl;

n (for Formula I) is 0;

E (for Formulas I, Ia-c and Ie-g) is a bond or $CH_2$;

$R^2$ (for Formulas I, Ia-c and Ie-g) is isopropyl, thienyl, phenyl, or pyridyl, each optionally substituted with halo, methyl, methylthio or (4-morpholino)methyl;

$R^3$ (for Formulas I and Ia-g) is methyl, ethyl, propyl, butyl, vinyl, allyl or ethoxyethyl, each optionally substituted with up to two groups independently selected from HO—, MeO—, $H_2N$—, MeC(=O)NH—, MeS(=O)_2NH—, $H_2NC(=O)$—, MeNHC(=O)—, $HO_2C$—, $(HO)_2P(=O)O$—, $H_2NS(=O)_2O$—, $H_2NS(=O)_2NH$—, MeNHC(=O)NH—, MeNHC(=O)O— oxo, cyano, $HO_2C$—, $HOCH_2CH_2NH$—, 4-morpholino, $HOCH_2C(=O)NH$—, $H_2NCH_2C(=O)NH$—, EtNHC(=O)NH, MeOC(=O)NH—, MeNHC(=NC=N)NH—, Me-, MeS—, $MeSO_2$-$MeSO_2N(Me)$-, $MeS(=O)_2NHC(=O)$—, imidazolylamino-, imidazolyl, tetrazolyl, $H_2NCONH$—, $H_2NCO_2$—, $HOCH_2CH_2O$—, MeNH—, $Me_2N$— and MeCONMe;

$R^5$ (Formulas I and Ia-g) is hydrogen or methyl.

A sixth embodiment of the invention is a compound of Formula I or any one of Formulas Ia-f wherein the values are as defined for Formula I above in the first, second, third, forth or fifth embodiment; and $R^1$ is (a) absent or (b) is selected from $(C_1-C_6)$alkyl, $(C_2-C_6)$alkenyl, $(C_2-C_6)$alkynyl, $(C_1-C_3)$alkoxy$(C_1-C_3)$alkoxy, or $(C_1-C_3)$alkoxy$(C_1-C_3)$alkyl and is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, heterocyclyl, heteroaryl, arylamino and heteroarylamino;

$A^1$ is (a) a bond, or (b) $(C_1)$alkylene, $CH_2CH_2O$, wherein the oxygen is attached to $Cy^1$, or $CH_2C(=O)$, wherein the carbonyl carbon is attached to $Cy^1$;

$Cy^1$ is aryl, heteroaryl, monocyclic cycloalkyl or monocyclic heterocyclyl, each optionally substituted with 1 to 4 groups independently selected from nitro, amino, hydroxy, carboxy, $(C_1-C_6)$alkyl, hydroxy$(C_1-C_6)$alkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_4-C_7)$cycloalkylalkyl, $(C_1-C_6)$alkoxy, $(C_3-C_6)$cycloalkoxy, $(C_4-C_2)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_2)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_2)$cycloalkylalkanesulfonyl, halo$(C_1-C_6)$alkanesulfonyl, halo$(C_3-C_6)$cycloalkanesulfonyl, halo$(C_4-C_2)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, oxo, amino$(C_1-C_6)$alkyl, $(C_1-C_6)$alkylamino$(C_1-C_6)$alkyl, di$(C_1-C_6)$alkylamino$(C_1-C_6)$ alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy and ($C_1$-$C_6$)alkylcarbonyl; or if the substitution is either meta or para to $A^1$, the substituents may also include optionally substituted cycloalkyl, optionally substituted halocycloalkyl or optionally substituted heteroaryl.

$A^2$ is (a) a bond, O, S or $NR^4$; or (b) ($C_1$-$C_3$)alkylene or ($C_1$-$C_2$)alkyleneoxy, each of which is optionally substituted with 1 to 4 groups independently selected from methyl, ethyl, trifluoromethyl or oxo;

$Cy^2$ is meta or para to $A_1$ and is (a) hydrogen or (b) aryl, heteroaryl, cycloalkyl pyrrolidine, pyrrolidin-2-one, 1-methylpyrrolidin-2-one, piperidine, piperidin-2-one, dihydropyridine, tetrahydropyridine, piperazine, 1-(2,2,2-trifluoroethyl)piperazine, 1,2-dihydro-2-oxopyridine, 1,4-dihydro-4-oxopyridine, piperazin-2-one, 3,4,5,6-tetrahydro-4-oxopyrimidine, 3,4-dihydro-4-oxopyrimidine, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide isothiazolidine 1,1-dioxide, 6-oxo-1,6-dihydropyridazin-3-yl, 6-oxo-1,6-dihydropyridazin-4-yl, 5-oxo-4,5-dihydro-1H-1,2,4-triazol-3-yl and 5-oxo-4,5-dihydro-1H-imidazol-2-yl optionally substituted with 1 to 4 groups independently selected from fluorine, chlorine, bromine, iodine, cyano, nitro, hydroxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylthio, ($C_4$-$C_7$)cycloalkylalkylthio, halo($C_1$-$C_6$)alkylthio, halo($C_3$-$C_6$)cycloalkylhio, halo($C_4$-$C_7$)cycloalkylalkylthio, ($C_1$-$C_6$)alkanesulfinyl, ($C_3$-$C_6$)cycloalkanesulfinyl, $C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy and ($C_1$-$C_6$)alkylcarbonyl;

E is (a) a bond or (b) ($C_1$-$C_3$)alkylene or ($C_1$-$C_2$)alkylenyloxy, wherein the 0 is attached to $R^2$, each of which is optionally substituted with 1 to 4 groups independently selected from methyl, ethyl, trifluoromethyl or oxo;

$R^2$ is ($C_1$-$C_6$)alkyl, aryl, heteroaryl, cycloalkyl or heterocyclyl and is optionally substituted with up to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylthio, ($C_4$-$C_7$)cycloalkylalkylthio, halo($C_1$-$C_6$)alkylthio, halo($C_3$-$C_6$)cycloalkylhio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy and ($C_1$-$C_6$)alkylcarbonyl;

$R^3$ is selected from ($C_1$-$C_6$)alkyl, ($C_2$-$C_6$)alkenyl, ($C_2$-$C_6$)alkynyl, ($C_3$-$C_5$)cycloalkyl($C_1$-$C_4$)alkyl, ($C_1$-$C_3$)alkoxy($C_1$-$C_3$)alkoxy, or ($C_1$-$C_3$)alkoxy($C_1$-$C_3$)alkyl and is optionally substituted with up to four groups independently selected from fluorine, cyano, oxo, $R^4$, $R^4O$—, $(R^4)_2N$—, $R^4O_2C$—, $R^4C(=O)O$—, $R^4S$, $R^4S(=O)$—, $R^4S(=O)_2$—, $R^4C(=O)NR^4$, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)N(R^4O)_2P(=O)O$—, $(R^4)_2NC(=O)P(=O)NR^4$—, $R^4OS(=O)_2NR^4$—, $(R^4)_2NS(=O)_2O$—, $(R^4)_2NS(=O)_2NR^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, spirocycloalkyl; heterocyclyl (which in turn may be optionally substituted with alkyl, haloalkyl, halogen or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); and $R^4$ is independently selected from H, $(C_1$-$C_6)$alkyl, halo$(C_1$-$C_6)$alkyl, amino$(C_1$-$C_6)$alkyl, $(C_1$-$C_6)$alkylamino$(C_1$-$C_6)$alkyl, di$(C_1$-$C_6)$alkylamino$(C_1$-$C_6)$alkyl, hydroxy$(C_1$-$C_6)$alkyl and $(C_1$-$C_6)$alkoxy$(C_1$-$C_6)$alkyl;

or a pharmaceutically acceptable salt, enantiomer or diastereomer thereof.

Another embodiment is a compound of Formula Ia:

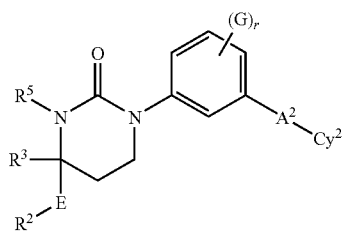

Ia wherein $A^2$, $Cy^2$, E, $R^2$, $R^3$, and $R^5$ are as defined for Formula I above; r is 0, 1, 2, 3 or 4; and substituents G are independently selected from fluorine, chlorine, bromine, iodine, cyano, nitro, amino, hydroxy, carboxy, $(C_1$-$C_6)$alkyl, hydroxy$(C_1$-$C_6)$alkyl, $(C_3$-$C_6)$cycloalkyl, hydroxy$(C_3$-$C_6)$cycloalkyl, $(C_4$-$C_7)$cycloalkylalkyl, $(C_2$-$C_6)$alkenyl, halo$(C_2$-$C_6)$alkenyl, hydroxy$(C_2$-$C_6)$alkenyl, $(C_2$-$C_6)$alkynyl, $(C_3$-$C_6)$cycloalkyl$(C_2$-$C_4)$alkynyl, halo$(C_1$-$C_6)$alkyl, halo$(C_3$-$C_6)$cycloalkyl, halo$(C_4$-$C_7)$cycloalkylalkyl, $(C_1$-$C_6)$alkoxy, $(C_3$-$C_6)$cycloalkoxy, $(C_4$-$C_7)$cycloalkylalkoxy, halo$(C_1$-$C_6)$alkoxy, halo$(C_3$-$C_6)$cycloalkoxy, halo$(C_4$-$C_7)$cycloalkylalkoxy, $(C_1$-$C_6)$alkylthio, $(C_3$-$C_6)$cycloalkylhio, $(C_4$-$C_7)$cycloalkylalkylthio, halo$(C_1$-$C_6)$alkylthio, halo$(C_3$-$C_6)$cycloalkylhio, halo$(C_4$-$C_7)$cycloalkylalkylthio, $(C_1$-$C_6)$alkanesulfinyl, $(C_3$-$C_6)$cycloalkanesulfinyl, $(C_4$-$C_7)$cycloalkylalkanesulfinyl, halo$(C_1$-$C_6)$alkane-sulfinyl, halo$(C_3$-$C_6)$cycloalkanesulfinyl, halo$(C_4$-$C_7)$cycloalkylalkanesulfinyl, $(C_1$-$C_6)$alkanesulfonyl, $(C_3$-$C_6)$cycloalkanesulfonyl, $(C_4$-$C_7)$cycloalkylalkanesulfonyl, halo$(C_1$-$C_6)$alkanesulfonyl, halo$(C_3$-$C_6)$cycloalkanesulfonyl, halo$(C_4$-$C_7)$cycloalkylalkanesulfonyl, $(C_1$-$C_6)$alkylamino, di$(C_1$-$C_6)$alkylamino, $(C_1$-$C_6)$alkoxy$(C_1$-$C_6)$alkoxy, halo$(C_1$-$C_6)$alkoxy$(C_1$-$C_6)$alkoxy, $(C_1$-$C_6)$alkoxycarbonyl, $H_2NCO$, $H_2NSO_2$, $(C_1$-$C_6)$alkylaminocarbonyl, di$(C_1$-$C_6)$alkylaminocarbonyl, $(C_1$-$C_3)$alkoxy$(C_1$-$C_3)$alkylaminocarbonyl, heterocyclylcarbonyl, $(C_1$-$C_6)$alkylaminosulfonyl, di$(C_1$-$C_6)$alkylaminosulfonyl, heterocyclosulfonyl, $(C_1$-$C_6)$alkylcarbonylamino, $(C_1$-$C_6)$alkylcarbonylamino$(C_1$-$C_6)$alkyl, $(C_1$-$C_6)$alkylsulfonylamino, $(C_1$-$C_6)$alkylsulfonylamino$(C_1$-$C_6)$alkyl, $(C_1$-$C_6)$alkoxycarbonyl$(C_1$-$C_6)$alkoxy, $(C_1$-$C_6)$alkoxy$(C_1$-$C_6)$alkyl, halo$(C_1$-$C_6)$alkoxy$(C_1$-$C_6)$alkyl, hydroxy$(C_1$-$C_6)$alkoxy, heteroaryl, amino$(C_1$-$C_6)$alkyl, $(C_1$-$C_6)$alkylamino$(C_1$-$C_6)$alkyl, di$(C_1$-$C_6)$alkylamino$(C_1$-$C_6)$alkyl amino$(C_2$-$C_6)$alkoxy, $(C_1$-$C_6)$alkylamino$(C_2$-$C_6)$alkoxy, di$(C_1$-$C_6)$alkylamino$(C_2$-$C_6)$alkoxyl or $(C_1$-$C_6)$alkylcarbonyl;

or a pharmaceutically acceptable salt, enantiomer or diastereomer thereof.

Another embodiment is a compound of Formula Ib:

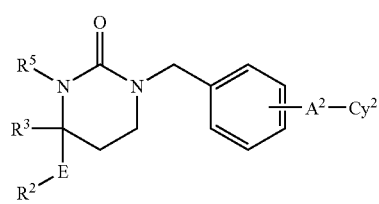

Ib wherein $A^2$, $Cy^2$, E, $R^2$, $R^3$ and $R^5$ are as defined for Formula I above;

or a pharmaceutically acceptable salt, enantiomer or diastereomer thereof. In a specific embodiment, $A^2$-$Cy^2$ is meta or para to the carbon atom bonded to —$CH_2$—UR, wherein "UR" is the urea ring.

Another embodiment is a compound of Formula Ic:

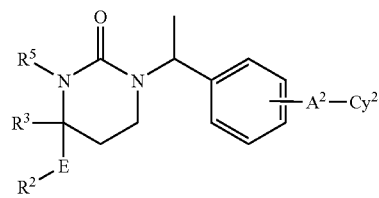

Ic wherein $A^2$, $Cy^2$, E, $R^2$, $R^3$ and $R^5$ are as defined for Formula I above;

or a pharmaceutically acceptable salt, enantiomer or diastereomer thereof. In a specific embodiment, $A^2$-$Cy^2$ is meta or para to the carbon atom bonded to —$CH(CH_3)$—UR, wherein "UR" is the urea ring.

Another embodiment is a compound of Formula Id:

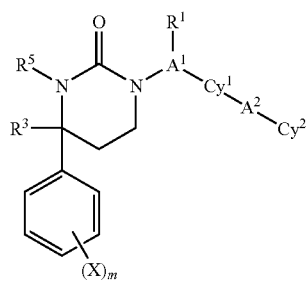

Id wherein $A^1$, $R^1$, $Cy^1$, $A^2$, $Cy^2$, $R^3$, and $R^5$ are as defined for Formula I above; m is 0, 1, 2, 3 or 4; and substituents X are independently selected from fluorine, chlorine, bromine, iodine, cyano, nitro, amino, hydroxy, carboxy, $(C_1$-$C_6)$alkyl, hydroxy$(C_1$-$C_6)$alkyl, $(C_3$-$C_6)$cycloalkyl, hydroxy$(C_3$-$C_6)$cycloalkyl, $(C_4$-$C_7)$cycloalkylalkyl, $(C_2$-$C_6)$alkenyl, halo$(C_2$-$C_6)$alkenyl, hydroxy$(C_2$-$C_6)$alkenyl, $(C_2$-$C_6)$alkynyl, $(C_3$-$C_6)$cycloalkyl$(C_2$-$C_4)$alkynyl, halo$(C_1$-$C_6)$alkyl, halo$(C_3$-$C_6)$cycloalkyl, halo$(C_4$-$C_7)$cycloalkylalkyl, $(C_1$-$C_6)$alkoxy, $(C_3$-$C_6)$cycloalkoxy, $(C_4$-$C_7)$cycloalkylalkoxy, halo$(C_1$-$C_6)$alkoxy, halo$(C_3$-$C_6)$cycloalkoxy, halo$(C_4$-$C_7)$cycloalkylalkoxy, $(C_1$-$C_6)$alkylthio, $(C_3$-$C_6)$cycloalkylhio, $(C_4$-$C_7)$cycloalkylalkylthio, halo$(C_1$-$C_6)$alkylthio, halo$(C_3$-$C_6)$cycloalkylhio, halo$(C_4$-$C_7)$cycloalkylalkylthio, $(C_1$-$C_6)$alkanesulfinyl, $(C_3$-$C_6)$cycloalkanesulfinyl, $(C_4$-$C_7)$cycloalkylalkanesulfinyl, halo$(C_1$-$C_6)$alkane-sulfinyl, halo$(C_3$-

$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl and ($C_1$-$C_6$)alkylcarbonyl;

or a pharmaceutically acceptable salt, enantiomer or diastereomer thereof. In a specific embodiment, $A^2$-$Cy^2$ is meta or para to the carbon atom bonded to -$A_1$.

Another embodiment is a compound of Formula Ie:

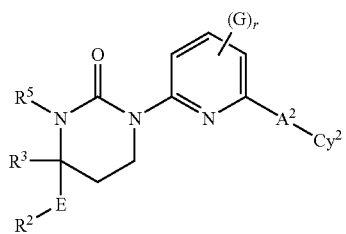

Ie wherein $A^2$, $Cy^2$, E, $R^2$, $R^3$, and $R^5$ are as defined for Formula I above, r is 0, 1, 2, 3 or 4; and substituents G are independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylthio, ($C_4$-$C_7$)cycloalkylalkylthio, halo($C_1$-$C_6$)alkylthio, halo($C_3$-$C_6$)cycloalkylthio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl and ($C_1$-$C_6$)alkylcarbonyl;

or a pharmaceutically acceptable salt, enantiomer or diastereomer thereof.

Another embodiment is a compound of Formula If:

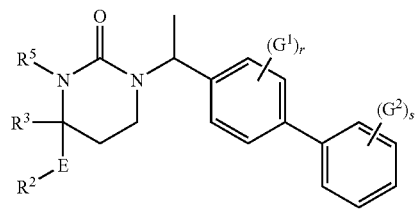

If wherein E, $R^2$, $R^3$, and $R^5$ are as defined for Formula I above, r and s are independently 0, 1, 2, 3 or 4; and $G^1$ and $G^2$ are independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylthio, ($C_4$-$C_7$)cycloalkylalkylthio, halo($C_1$-$C_6$)alkylthio, halo($C_3$-$C_6$)cycloalkylhio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, amino($C_1$-$C_6$)alkyl, ($C_1$-$C_6$)alkylamino($C_1$-$C_6$)alkyl, di($C_1$-$C_5$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl and ($C_1$-$C_6$)alkylcarbonyl;

or a pharmaceutically acceptable salt, enantiomer or diastereomer thereof.

Another embodiment is a compound of Formula Ig:

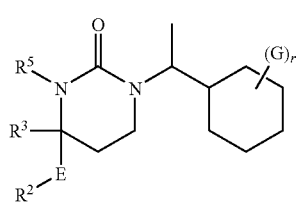

Ig wherein E, $R^2$, $R^3$ and $R^5$ are as defined for Formula I above, r is 0, 1, 2, 3 or 4; and substituents G are independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;

or a pharmaceutically acceptable salt, enantiomer or diastereomer thereof.

Another embodiment is a compound of Formula Ih:

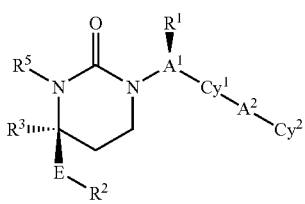

Ih wherein, $Cy^1$, $A^1$, $R^1$, $A^2$, $Cy^2$, $R^2$, E, $R^3$ and $R^5$ are as defined for the first, second, third, fourth, fifth or sixth embodiments described for Formula I above and at least one and preferably both stereocenters are in the configuration depicted. Pharmaceutically acceptable salts, enantiomers or diastereomers thereof are also included.

Another embodiment is a compound of Formula Ii:

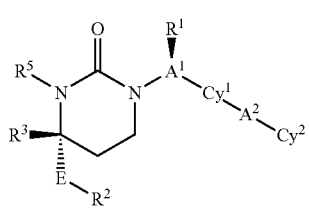

Ii wherein, $Cy^1$, $A^1$, $R^1$, $A^2$, $Cy^2$, $R^2$, E, $R^3$ and $R^5$ are as defined for the first, second, third, fourth, fifth or sixth embodiments described for Formula I above and at least one and preferably both stereocenters are in the configuration depicted. Pharmaceutically acceptable salts, enantiomers or diastereomers thereof are also included.

Another embodiment is a compound of Formula Ij:

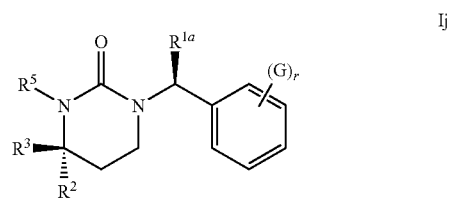

Ij wherein $R^2$, $R^3$ and $R^5$ are as defined for the first, second, third, fourth, fifth or sixth embodiments described for Formula I above, $R^{1a}$ is methyl or ethyl, r is 0, 1, 2, 3 or 4, and substituents G are independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_2)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl;

or a pharmaceutically acceptable salt, enantiomer or diastereomer thereof.

Alternatively for Formula Ij:

$R^2$, $R^3$ and $R^5$ are as defined for the first, second, third, fourth, fifth or sixth embodiments described for Formula I above, $R^{1a}$ is methyl or ethyl, r is 0, 1, 2, 3 or 4, and substituents G are independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo ($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylthio, ($C_4$-$C_7$)cycloalkylalkylthio, halo($C_1$-$C_6$)alkylthio, halo($C_3$-$C_6$)cycloalkylthio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl; or a pharmaceutically acceptable salt, enantiomer or diastereomer thereof.

Another embodiment is a compound of Formula Ik:

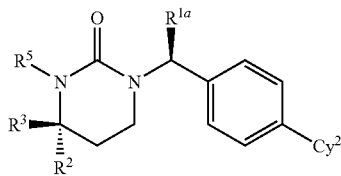

Ik wherein $Cy^2$, $R^2$, $R^3$ and $R^5$ are as defined for the first, second, third, fourth, fifth or sixth embodiments described for Formula I above, and $R^{1a}$ is methyl or ethyl;
or a pharmaceutically acceptable salt, enantiomer or diastereomer thereof.

Another embodiment is a compound of Formula Ik wherein $R^{1a}$ is methyl or ethyl, $R^2$ is phenyl optionally substituted with up to 2 groups selected from halogen, methyl, trifluoromethyl and cyano, $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl and $Cy^2$ is heterocyclyl optionally substituted with up to 3 groups independently selected from those described for $G^2$ in Formula If and oxo; or a pharmaceutically acceptable salt, enantiomer or diastereomer thereof.

Another embodiment is a compound of Formula Ik wherein $R^{1a}$ is methyl or ethyl, $R^2$ is phenyl optionally substituted with up to 2 groups selected from halogen, methyl, trifluoromethyl and cyano, $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl and $Cy^2$ is 1,2-dihydro-2-oxo-4-pyridyl, 1,2-dihydro-2-oxo-5-pyridyl, 5-thiazolyl, 2-thiazolyl, 3-pyridyl, 4-pyridyl, cyclopropyl or 2-thienyl each optionally substituted with up to 3 groups independently selected from fluorine, chlorine, cyano, hydroxy, amino, ($C_1$-$C_4$)alkyl, ($C_3$-$C_4$)cycloalkyl, ($C_3$-$C_4$)cycloalkyl($C_1$-$C_2$)alkyl, halo($C_1$-$C_4$)alkyl, ($C_1$-$C_4$)alkoxy, ($C_1$-$C_4$)haloalkoxy, $CONH_2$, ($C_1$-$C_4$)alkylaminocarbonyl, di($C_1$-$C_4$)alkylaminocarbonyl, and ($C_1$-$C_4$)alkylcarbonylamino; or a pharmaceutically acceptable salt, enantiomer or diastereomer thereof.

Another embodiment is a compound of Formula Ik wherein $R^{1a}$ is methyl or ethyl, $R^2$ is phenyl optionally substituted with up to 2 groups selected from halogen, methyl, trifluoromethyl and cyano, $R^3$ is 2-hydroxy-2-methylpropyl or 2-cyano-2-methylpropyl and $Cy^2$ is 1,2-dihydro-2-oxo-5-pyridyl, 1,2-dihydro-2-oxo-4-pyridyl, 5-thiazolyl, 2-thiazolyl, 3-pyridyl, 4-pyridyl or 2-thienyl optionally substituted with up to 2 groups independently selected from ($C_1$-$C_4$)alkyl, ($C_3$-$C_4$)cycloalkyl, halo($C_1$-$C_4$)alkyl and halogen;

or a pharmaceutically acceptable salt, enantiomer or diastereomer thereof.

Another embodiment is a compound of Formula Ik wherein $R^{1a}$ is methyl or ethyl, $R^2$ is phenyl optionally substituted with up to 2 groups selected from halogen, methyl, trifluoromethyl and cyano, $R^3$ is 2-hydroxy-2-methylpropyl or 2-cyano-2-methylpropyl and $Cy^2$ is heteroaryl optionally substituted with up 2 groups selected from ($C_1$-$C_4$)alkyl, halo($C_1$-$C_4$)alkyl, halogen, cyano, $CONH_2$, ($C_1$-$C_4$)alkylaminocarbonyl, di($C_1$-$C_4$)alkylaminocarbonyl and ($C_3$-$C_5$)cycloalkylaminocarbonyl or a pharmaceutically acceptable salt, enantiomer or diastereomer thereof. In another embodiment, $Cy^2$ is heteroaryl optionally substituted with one group selected from ($C_1$-$C_4$)alkyl, halo($C_1$-$C_4$)alkyl, halogen, cyano, CONHMe and $CONMe_2$; or a pharmaceutically acceptable salt, enantiomer or diastereomer thereof. In an alternative embodiment $CONH_2$ is excluded as a permissible substituent when $Cy^2$ is pyridine or thiazole. In yet another embodiment, $Cy^2$ is heteroaryl optionally substituted with one group selected from ($C_1$-$C_4$)alkyl, halo($C_1$-$C_4$)alkyl, halogen, cyano; or a pharmaceutically acceptable salt, enantiomer or diastereomer thereof.

Another embodiment is a compound of Formula Ik wherein $R^{1a}$ is methyl or ethyl, $R^2$ is phenyl or fluorophenyl, $R^3$ is 2-hydroxy-2-methylpropyl or 2-cyano-2-methylpropyl and $Cy^2$ is pyridine, thiazole or thienyl, each optionally substituted with methyl, fluorine, chlorine, cyano, $CONH_2$, CONHMe, $CONMe_2$, CONHt-Bu or CONHc-Pr; or a pharmaceutically acceptable salt, enantiomer or diastereomer thereof. In an alternative embodiment $CONH_2$ is excluded as a permissible substituent when $Cy^2$ is pyridine or thiazole.

Another embodiment of the invention is a compound of any one of Formulas $Il^{1-3}$ or a pharmaceutically acceptable salt, enantiomer or diastereomer thereof:

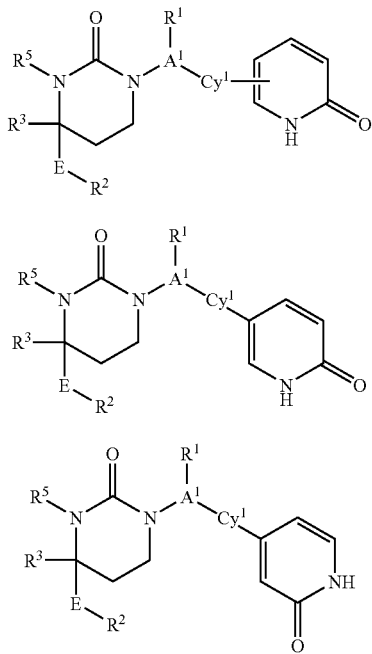

In Formulas Il$^{1-3}$, the oxodihydropyridyl ring in Formulas Il$^{1-3}$ are optionally substituted (substitution at ring carbons bonded to hydrogen and ring nitrogen atoms bonded to hydrogen atoms are encompassed, i.e., a "substitutable ring nitrogen atom") with up to four substituents as described above for Cy$^2$. Suitable substituents for Cy$^2$ and suitable values for R$^1$, R$^2$, R$^3$, R$^5$, A$^1$, Cy$^1$ and E are as defined in any one of the first, second, third, fourth, fifth or sixth embodiments. Alternatively, suitable substituents for Cy$^1$ and the oxodihydropyridyl ring in Formulas Il$^{1-3}$ are as described for G$^1$ and G$^2$, respectively, in Formula If, and values for R$^1$, R$^2$, R$^3$, R$^5$, A$^1$, Cy$^1$ and E are as defined in any one of the first, second, third, fourth, fifth or sixth embodiments. Alternatively, suitable substituents for Cy$^1$ include (C$_1$-C$_4$)alkyl, (C$_1$-C$_4$)alkoxy, (C$_1$-C$_4$)haloalkyl, (C$_1$-C$_4$)haloalkoxy, halogen, cyano and nitro; suitable substituents for a substitutable ring nitrogen atom in the oxodihydropyridyl ring in Formulas Il$^{1-3}$ include (C$_1$-C$_4$)alkyl, (C$_3$-C$_4$)cycloalkyl, (C$_3$-C$_4$)cycloalkyl(C$_1$-C$_2$)alkyl, and (C$_1$-C$_4$)haloalkyl; suitable substituents for a ring carbon atom in the oxodihydropyridyl ring in Formulas Il$^{1-3}$ include fluorine, chlorine, cyano, hydroxy, amino, (C$_1$-C$_4$) alkyl, (C$_3$-C$_4$)cycloalkyl, (C$_3$-C$_4$)cycloalkyl(C$_1$-C$_2$)alkyl, halo(C$_1$-C$_4$)alkyl, (C$_1$-C$_4$)alkoxy, (C$_1$-C$_4$)haloalkoxy, CONH$_2$, (C$_1$-C$_4$)alkylaminocarbonyl, di(C$_1$-C$_4$)alkylaminocarbonyl and (C$_1$-C$_4$)alkylcarbonylamino; and suitable values for R$^1$, R$^2$, R$^3$, R$^5$, A$^1$, Cy$^1$ and E are as defined in any one of the first, second, third, fourth, fifth or sixth embodiments.

For each of the embodiments described in the previous paragraph, R$^1$ is preferably methyl or ethyl.

For each of the embodiments described in the paragraph immediately following Formulas Il$^{1-3}$, R$^1$ is preferably methyl or ethyl; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas Il$^{1-3}$, R$^1$ is preferably methyl or ethyl; and R$^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiments described in the paragraph immediately following Formulas Il$^{1-3}$, R$^1$ is preferably methyl or ethyl; R$^2$ is phenyl optionally substituted with 1, 2 or 3 substituents selected from halo, cyano, CONH$_2$, (C$_1$-C$_4$) alkyl, (C$_1$-C$_4$)haloalkyl, and SO$_2$Me; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas Il$^{1-3}$, R$^1$ is preferably methyl or ethyl; R$^2$ is phenyl optionally substituted with 1, 2 or 3 substituents selected from halo, cyano, CONH$_2$, (C$_1$-C$_4$) alkyl, (C$_1$-C$_4$)haloalkyl, and SO$_2$Me; and R$^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiments described in the paragraph immediately following Formulas Il$^{1-3}$, R$^1$ is preferably methyl or ethyl; and R$^3$ is 2-hydroxy-2-methylpropyl or 2-cyano-2-methylpropyl.

For each of the embodiments described in the paragraph immediately following Formulas Il$^{1-3}$, R$^1$ is preferably methyl or ethyl; R$^2$ is phenyl or fluorophenyl; and R$^3$ is 2-hydroxy-2-methylpropyl or 2-cyano-2-methylpropyl.

For each of the embodiments described in the paragraph immediately following Formulas Il$^{1-3}$, R$^1$ is preferably methyl or ethyl; R$^2$ is phenyl or fluorophenyl; R$^3$ is 2-hydroxy-2-methylpropyl or 2-cyano-2-methylpropyl; the substituent on the substitutable ring nitrogen atom in the oxodihydropyridyl ring in Formulas Il$^{1-3}$ is (C$_1$-C$_4$)alkyl, (C$_3$-C$_4$)cycloalkyl, (C$_3$-C$_4$)cycloalkyl(C$_1$-C$_2$)alkyl, or (C$_1$-C$_2$)haloalkyl; and one or two ring carbon atoms in the oxodihydropyridyl ring in Formulas Il$^{1-3}$ are optionally substituted with methyl or ethyl.

For each of the embodiments described in the paragraph immediately following Formulas Il$^{1-3}$, R$^5$ is preferably hydrogen, methyl or ethyl. Specifically, R$^5$ is hydrogen or methyl.

Another embodiment of the invention is a compound of any one of Formulas Im$^{1-3}$, or a pharmaceutically acceptable salt, enantiomer or diastereomer thereof:

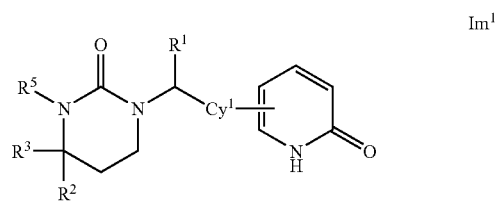

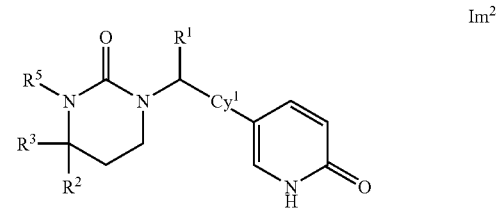

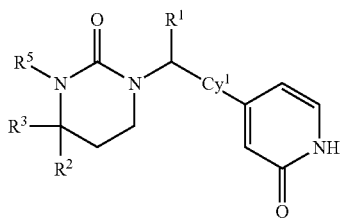

In Formulas Im$^{1-3}$, the oxodihydropyridyl ring are optionally substituted (substitution at ring carbons bonded to hydrogen and at nitrogen atoms bonded to hydrogen atoms are encompassed, i.e., a "substitutable ring nitrogen atom") with up to four substituents as described above for Cy$^2$. Suitable substituents for Cy$^2$ and suitable values for R$^1$, R$^2$, R$^3$, R$^5$ and Cy$^1$ are as defined in any one of the first, second, third, fourth, fifth or sixth embodiments. Alternatively, suitable substituents for Cy$^1$ and the oxodihydropyridyl ring in Formulas Im$^{1-3}$ are as described for G$^1$ and G$^2$, respectively, in Formula If, and values for R$^1$, R$^2$, R$^3$, R$^5$ and Cy$^1$ are as defined in any one of the first, second, third, fourth, fifth or sixth embodiments. Alternatively, suitable substituents for Cy$^1$ include (C$_1$-C$_4$)alkyl, (C$_1$-C$_4$)alkoxy, (C$_1$-C$_4$)haloalkyl, (C$_1$-C$_4$)haloalkoxy, halogen, cyano and nitro; suitable substituents for a substitutable ring nitrogen atom in the oxodihydropyridyl ring in Formulas Im$^{1-3}$ include (C$_1$-C$_4$)alkyl, (C$_3$-C$_4$)cycloalkyl, (C$_3$-C$_4$)cycloalkyl(C$_1$-C$_2$)alkyl and (C$_1$-C$_4$)haloalkyl; suitable substituents for a ring carbon atom in the oxodihydropyridyl ring in Formulas Im$^{1-3}$ include fluorine, chlorine, cyano, hydroxy, amino, (C$_1$-C$_4$)alkyl, (C$_3$-C$_4$)cycloalkyl, (C$_3$-C$_4$)cycloalkyl(C$_1$-C$_2$)alkyl, halo(C$_1$-C$_4$)alkyl, (C$_1$-C$_4$)alkoxy, (C$_1$-C$_4$)haloalkoxy, CONH$_2$, (C$_1$-C$_4$)alkylaminocarbonyl, di(C$_1$-C$_4$)alkylaminocarbonyl and (C$_1$-C$_4$) alkylcarbonylamino; and suitable values for R$^1$, R$^2$, R$^3$, R$^5$ and Cy$^1$ are as defined in any one of the first, second, third, fourth, fifth or sixth embodiments.

For each of the embodiments described in the previous paragraph, R$^1$ is preferably methyl or ethyl.

For each of the embodiments described in the paragraph immediately following Formulas Im$^{1-3}$, R$^1$ is preferably methyl or ethyl; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas Im$^{1-3}$, R$^1$ is preferably methyl or ethyl; and R$^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiments described in the paragraph immediately following Formulas Im$^{1-3}$, R$^1$ is preferably methyl or ethyl; R$^2$ is phenyl optionally substituted with 1, 2 or 3 substituents selected from halo, cyano, CONH$_2$, (C$_1$-C$_4$) alkyl, (C$_1$-C$_4$)haloalkyl and SO$_2$Me; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas Im$^{1-3}$, R$^1$ is preferably methyl or ethyl; R$^2$ is phenyl optionally substituted with 1, 2 or 3 substituents selected from halo, cyano, CONH$_2$, (C$_1$-C$_4$) alkyl, (C$_1$-C$_4$)haloalkyl and SO$_2$Me; and R$^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiments described in the paragraph immediately following Formulas Im$^{1-3}$, R$^1$ is preferably methyl or ethyl; and R$^3$ is 2-hydroxy-2-methylpropyl or 2-cyano-2-methylpropyl.

For each of the embodiments described in the paragraph immediately following Formulas Im$^{1-3}$, R$^1$ is preferably methyl or ethyl; R$^2$ is phenyl or fluorophenyl; and R$^3$ is 2-hydroxy-2-methylpropyl or 2-cyano-2-methylpropyl.

For each of the embodiments described in the paragraph immediately following Formulas Im$^{1-3}$, R$^1$ is preferably methyl or ethyl; R$^2$ is phenyl or fluorophenyl; R$^3$ is 2-hydroxy-2-methylpropyl or 2-cyano-2-methylpropyl; the substituent on the substitutable ring nitrogen atom in the oxodihydropyridyl ring in Formulas Im$^{1-3}$ is (C$_1$-C$_4$)alkyl, (C$_3$-C$_4$) cycloalkyl, (C$_3$-C$_4$)cycloalkyl(C$_1$-C$_2$)alkyl, or (C$_1$-C$_2$) haloalkyl; and one or two ring carbon atoms in the oxodihydropyridyl ring in Formulas Im$^{1-3}$ are optionally substituted with methyl or ethyl.

For each of the embodiments described in the paragraph immediately following Formulas In$^{1-3}$, R$^5$ is preferably hydrogen, methyl or ethyl. Specifically, R$^5$ is hydrogen or methyl.

Another embodiment of the invention is a compound of any one for Formulas In$^{1-3}$, or a pharmaceutically acceptable salt thereof:

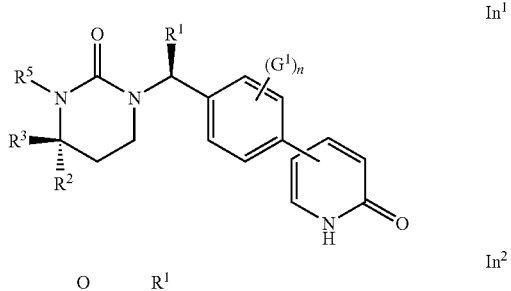

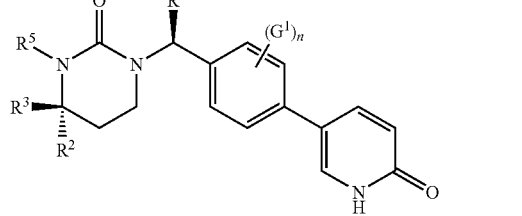

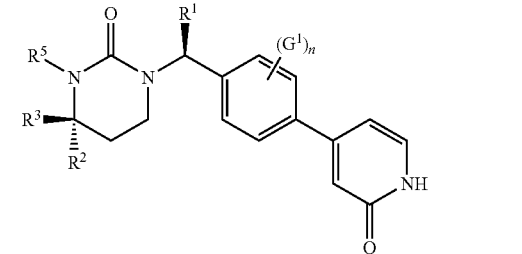

In Formulas In$^{1-3}$, the oxodihydropyridyl ring in Formulas In$^{1-3}$ are optionally substituted (substitution at ring carbons bonded to hydrogen and at nitrogen atoms bonded to hydrogen atoms are encompassed, i.e., a "substitutable ring nitrogen atom") with up to four substituents as described above for Cy$^2$; suitable values for G$^1$ are as described for G$^1$ in Formula If; n is 0, 1, 2 or 3; and suitable substituents for Cy$^2$ and suitable values for $R^1$, $R^2$, $R^3$ and $R^5$ are as defined in any one of the first, second, third, fourth, fifth or sixth embodiments. Alternatively, n is 0, 1, 2 or 3; suitable values for $G^1$ and substituents for the oxodihydropyridyl ring in Formulas $In^{1-3}$ are as described for $G^1$ and $G^2$, respectively, in Formula If, and values for $R^1$, $R^2$, $R^3$ and $R^5$ are as defined in any one of the first, second, third, fourth, fifth or sixth embodiments. Alternatively, n is 0, 1, 2 or 3; suitable values for $G^1$ include $(C_1$-$C_4)$alkyl, $(C_1$-$C_4)$alkoxy, $(C_1$-$C_4)$haloalkyl, $(C_1$-$C_4)$haloalkoxy, halogen, cyano and nitro; suitable substituents for a substitutable ring nitrogen atom in the oxodihydropyridyl ring in Formulas $In^{1-3}$ include $C_1$-$C_4$ alkyl, $(C_3$-$C_4)$cycloalkyl, $(C_3$-$C_4)$cycloalkyl$(C_1$-$C_2)$alkyl and $C_1$-$C_4$ haloalkyl; suitable substituents for a ring carbon atom in the oxopyridyl, oxopyridazinyl, oxopyrimidinyl and oxopyrazinyl rings in Formulas $In^{1-3}$ include fluorine, chlorine, cyano, hydroxy, amino, $(C_1$-$C_4)$alkyl, $(C_3$-$C_4)$cycloalkyl, $(C_3$-$C_4)$cycloalkyl$(C_1$-$C_2)$alkyl, halo$(C_1$-$C_4)$alkyl, $(C_1$-$C_4)$alkoxy, $(C_1$-$C_4)$haloalkoxy, $CONH_2$, $(C_1$-$C_4)$alkylaminocarbonyl, di$(C_1$-$C_4)$alkylaminocarbonyl and $(C_1$-$C_4)$alkylcarbonylamino; and suitable values for $R^1$, $R^2$, $R^3$ and $R^5$ are as defined in any one of the first, second, third, fourth, fifth or sixth embodiments.

For each of the embodiments described in the previous paragraph, $R^1$ is preferably methyl or ethyl.

For each of the embodiments described in the paragraph immediately following Formulas $In^{1-3}$, $R^1$ is preferably methyl or ethyl; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas $In^{1-3}$, $R^1$ is preferably methyl or ethyl; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiments described in the paragraph immediately following Formulas $In^{1-3}$, $R^1$ is preferably methyl or ethyl; $R^2$ is phenyl optionally substituted with 1, 2 or 3 substituents selected from halo, cyano, $CONH_2$, $(C_1$-$C_4)$ alkyl, $(C_1$-$C_4)$haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas $In^{1-3}$, $R^1$ is preferably methyl or ethyl; $R^2$ is phenyl optionally substituted with 1, 2 or 3 substituents selected from halo, cyano, $CONH_2$, $(C_1$-$C_4)$ alkyl, $(C_1$-$C_4)$haloalkyl and $SO_2Me$; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiments described in the paragraph immediately following Formulas $In^{1-3}$, $R^1$ is preferably methyl or ethyl; and $R^5$ is 2-hydroxy-2-methylpropyl or 2-cyano-2-methylpropyl.

For each of the embodiments described in the paragraph immediately following Formulas $In^{1-3}$, $R^1$ is preferably methyl or ethyl; $R^2$ is phenyl or fluorophenyl; and $R^3$ is 2-hydroxy-2-methylpropyl or 2-cyano-2-methylpropyl.

For each of the embodiments described in the paragraph immediately following Formulas $In^{1-3}$, $R^1$ is preferably methyl or ethyl; $R^2$ is phenyl or fluorophenyl; $R^3$ is 2-hydroxy-2-methylpropyl or 2-cyano-2-methylpropyl; the substituent on the substitutable ring nitrogen atom in the oxodihydropyridyl ring in Formulas $In^{1-3}$ is $(C_1$-$C_4)$alkyl, $(C_3$-$C_4)$ cycloalkyl, $(C_3$-$C_4)$cycloalkyl$(C_1$-$C_2)$alkyl, or $(C_1$-$C_2)$ haloalkyl; and one or two ring carbon atoms in the oxodihydropyridyl ring in Formulas $In^{1-3}$ are optionally substituted with methyl or ethyl.

For each of the embodiments described in the paragraph immediately following Formulas $In^{1-3}$, $R^5$ is preferably hydrogen, methyl or ethyl. Specifically, $R^5$ is hydrogen or methyl.

Another embodiment of the invention is a compound represented by any one of Formulas $Io^{1-2}$ or a pharmaceutically acceptable salt thereof:

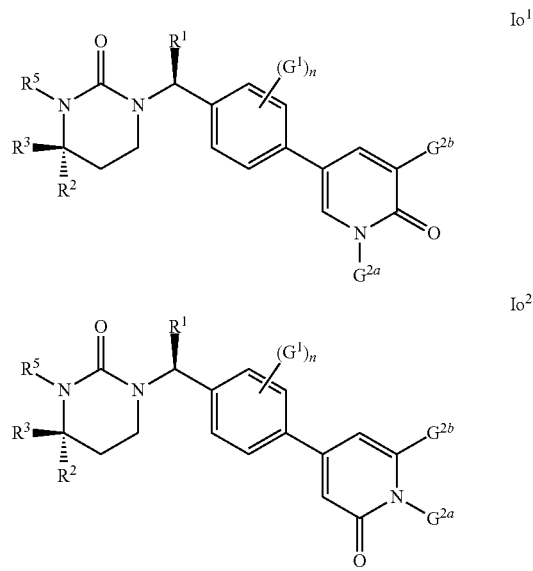

In Formulas $Io^{1-2}$, $G^1$ is $(C_1$-$C_4)$alkyl, $(C_1$-$C_4)$alkoxy, $(C_1$-$C_4)$ haloalkyl, $(C_1$-$C_4)$haloalkoxy, halogen, cyano or nitro; n is 0, 1 or 2; $G^{2a}$ is $(C_1$-$C_4)$alkyl, $(C_3$-$C_4)$cycloalkyl or $(C_1$-$C_4)$ haloalkyl; $G^{2b}$ is hydrogen, fluorine, chlorine, cyano, hydroxy, amino, $(C_1$-$C_4)$alkyl, $(C_3$-$C_4)$cycloalkyl, $(C_3$-$C_4)$ cycloalkyl$(C_1$-$C_2)$alkyl, halo$(C_1$-$C_4)$alkyl, $(C_1$-$C_4)$alkoxy, $(C_1$-$C_4)$haloalkoxy, $CONH_2$, $(C_1$-$C_4)$alkylaminocarbonyl, di$(C_1$-$C_4)$alkylaminocarbonyl or $(C_1$-$C_4)$alkylcarbonylamino; and suitable values for $R^1$, $R^2$, $R^3$ and $R^5$ are as defined in any one of the first, second, third, fourth, fifth or sixth embodiments.

For each of the embodiments described in the previous paragraph, $R^1$ is preferably methyl or ethyl.

For each of the embodiments described in the paragraph immediately following Formulas $Io^{1-2}$, $R^1$ is preferably methyl or ethyl; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas $Io^{1-2}$, $R^1$ is preferably methyl or ethyl; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiments described in the paragraph immediately following Formulas $Io^{1-2}$, $R^1$ is preferably methyl or ethyl; $R^2$ is phenyl optionally substituted with 1, 2 or 3 substituents selected from halo, cyano, $CONH_2$, $(C_1$-$C_4)$ alkyl, $(C_1$-$C_4)$haloalkyl and $SO_2Me$; and $R^3$ is $MeSO_2NHCH_2CH_2CH_2$, $H_2NC(=O)CH_2CH_2$, $H_2NC(=O)$ $CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas Io$^{1-2}$, R$^1$ is preferably methyl or ethyl; R$^2$ is phenyl optionally substituted with 1, 2 or 3 substituents selected from halo, cyano, CONH$_2$, (C$_1$-C$_4$) alkyl, (C$_1$-C$_4$)haloalkyl and SO$_2$Me; and R$^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiments described in the paragraph immediately following Formulas Io$^{1-2}$, R$^1$ is preferably methyl or ethyl; and R$^3$ is 2-hydroxy-2-methylpropyl or 2-cyano-2-methylpropyl.

For each of the embodiments described in the paragraph immediately following Formulas Io$^{1-2}$, R$^1$ is preferably methyl or ethyl; R$^2$ is phenyl or fluorophenyl; and R$^3$ is 2-hydroxy-2-methylpropyl or 2-cyano-2-methylpropyl.

For each of the embodiment described in the paragraph immediately following Formulas Io$^{1-2}$, R$^1$ is preferably methyl or ethyl; R$^2$ is phenyl or fluorophenyl; R$^3$ is 2-hydroxy-2-methylpropyl or 2-cyano-2-methylpropyl; the substituent G$^{2a}$ is selected from (C$_1$-C$_4$)alkyl, (C$_3$-C$_4$)cycloalkyl, (C$_3$-C$_4$)cycloalkyl(C$_1$-C$_2$)alkyl, and (C$_1$-C$_2$)haloalkyl; and G$^{2b}$ is optionally selected from hydrogen, methyl or ethyl.

For each of the embodiments described in the paragraph immediately following Formulas Io$^{1-2}$, R$^5$ is preferably hydrogen, methyl or ethyl. Specifically, R$^5$ is hydrogen or methyl.

Another embodiment of the invention is a compound of any one of Formulas Ip$^{1-6}$ or a pharmaceutically acceptable salt, enantiomer or diastereomer thereof:

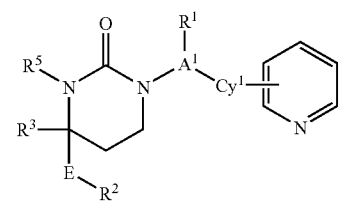

Ip$^1$

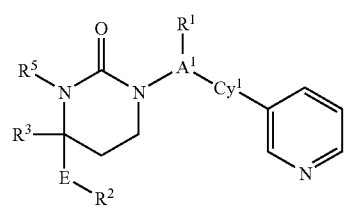

Ip$^2$

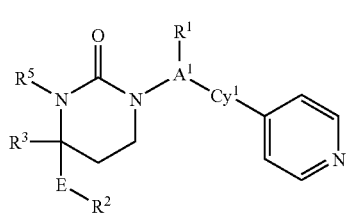

Ip$^3$

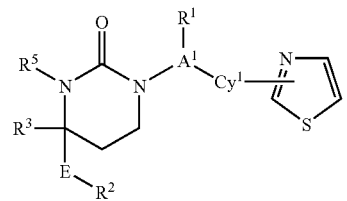

Ip$^4$

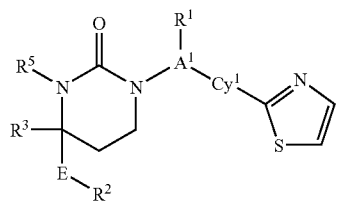

Ip$^5$

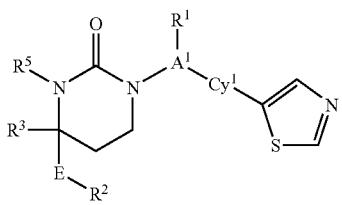

Ip$^6$

In Formulas Ip$^{1-6}$, the pyridine and thiazole rings in Formulas Ip$^{1-6}$ are optionally substituted (substitution at ring carbons bonded to hydrogen and ring nitrogen atoms bonded to hydrogen atoms are encompassed, i.e., a "substitutable ring nitrogen atom") with up to four substituents as described above for Cy$^2$. Alternatively, —CHO, NH$_2$—SO$_2$NH$_2$, —COOH, and —CONH$_2$ are excluded as permissible substituents for the pyridine and thiazole rings at the position corresponding to Cy$^2$ for all of the specific embodiments described above for Formulas Ip$^{1-6}$. Suitable substituents for Cy$^2$ and suitable values for R$^1$, R$^2$, R$^3$, R$^5$, A$^1$, Cy$^1$ and E are as defined in any one of the first, second, third, fourth, fifth or sixth embodiments. Alternatively, suitable substituents for Cy$^1$ and the pyridine and thiazole rings in Formulas Ip$^{1-6}$ are as described for G$^1$ and G$^2$, respectively, in Formula If, and values for R$^1$, R$^2$, R$^3$, R$^5$, A$^1$, Cy$^1$ and E are as defined in any one of the first, second, third, fourth, fifth or sixth embodiments. Alternatively, suitable substituents for Cy$^1$ include (C$_1$-C$_4$)alkyl, (C$_1$-C$_4$)alkoxy, (C$_1$-C$_4$)haloalkyl, (C$_1$-C$_4$)haloalkoxy, halogen, cyano and nitro; suitable substituents for a ring carbon atom in the pyridine and thiazole rings in Formulas Ip$^{1-6}$ include fluorine, chlorine, cyano, amino, (C$_1$-C$_4$)alkyl, (C$_3$-C$_4$)cycloalkyl, (C$_3$-C$_4$)cycloalkyl(C$_1$-C$_2$)alkyl, halo(C$_1$-C$_4$)alkyl, (C$_1$-C$_4$)alkoxy, (C$_1$-C$_4$)haloalkoxy, CONH$_2$, (C$_1$-C$_4$)alkylaminocarbonyl, di(C$_1$-C$_4$)alkylaminocarbonyl, (C$_3$-C$_4$)cycloalkylaminocarbonyl, {(C$_1$-C$_4$)alkyl}{(C$_3$-C$_4$)cycloalkyl}aminocarbonyl and (C$_1$-C$_4$)alkylcarbonylamino; the ring nitrogen in the pyridine rings in Formulas Ip$^{1-3}$ is optionally substituted by oxo; and suitable values for R$^1$, R$^2$, R$^3$, R$^5$, A$^1$, Cy$^1$ and E are as defined in any one of the first, second, third, fourth, fifth or sixth embodiments.

For each of the embodiments described in the previous paragraph, R$^1$ is preferably methyl or ethyl.

For each of the embodiments described in the paragraph immediately following Formulas Ip$^{1-6}$, R$^1$ is preferably methyl or ethyl; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas Ip$^{1-6}$, R$^1$ is preferably methyl or ethyl; and R$^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiments described in the paragraph immediately following Formulas Ip$^{1-6}$, R$^1$ is preferably methyl or ethyl; R$^2$ is phenyl optionally substituted with 1, 2 or 3 substituents selected from halo, cyano, CONH$_2$, (C$_1$-C$_4$) alkyl, (C$_1$-C$_4$)haloalkyl and SO$_2$Me; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas Ip$^{1-6}$, R$^1$ is preferably methyl or ethyl; R$^2$ is phenyl optionally substituted with 1, 2 or 3 substituents selected from halo, cyano, CONH$_2$, (C$_1$-C$_4$) alkyl, (C$_1$-C$_4$)haloalkyl and SO$_2$Me; and R$^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiments described in the paragraph immediately following Formulas Ip$^{1-6}$, R$^1$ is preferably methyl or ethyl; and R$^3$ is 2-hydroxy-2-methylpropyl or 2-cyano-2-methylpropyl.

For each of the embodiments described in the paragraph immediately following Formulas Ip$^{1-5}$, R$^1$ is preferably methyl or ethyl; R$^2$ is phenyl or fluorophenyl; and R$^3$ is 2-hydroxy-2-methylpropyl or 2-cyano-2-methylpropyl.

For each of the embodiments described in the paragraph immediately following Formulas Ip$^{1-5}$, R$^1$ is preferably methyl or ethyl; R$^2$ is phenyl or fluorophenyl; R$^3$ is 2-hydroxy-2-methylpropyl or 2-cyano-2-methylpropyl; one or two ring carbon atoms in the pyridine and thiazole rings in Formulas Ip$^{1-5}$ are optionally substituted with fluoro, chloro, cyano, CONH$_2$, CONHMe, CONMe$_2$, CONHc-Pr, methoxy, ethoxy, methyl, ethyl or CF$_3$; the ring nitrogen in the pyridine rings in Formulas Ip$^{1-3}$ is optionally substituted by oxo.

For each of the embodiments described in the paragraph immediately following Formulas Ip$^{1-5}$ R$^5$ is preferably hydrogen, methyl or ethyl. Specifically, R$^5$ is hydrogen or methyl.

Another embodiment of the invention is a compound of any one of Formulas Iq$^{1-5}$, or a pharmaceutically acceptable salt, enantiomer or diastereomer thereof:

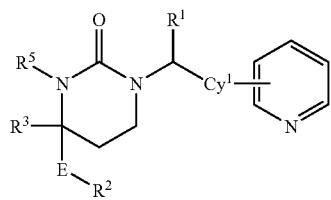

Iq$^1$

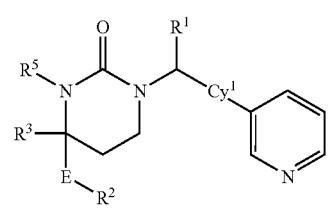

Iq$^2$

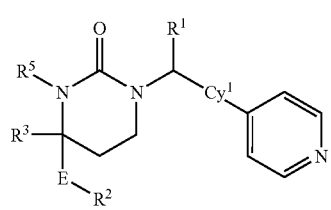

Iq$^3$

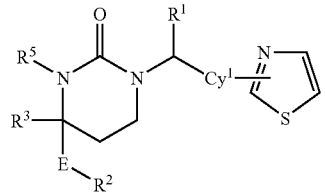

Iq$^4$

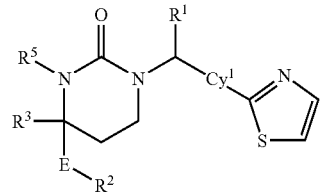

Iq$^5$

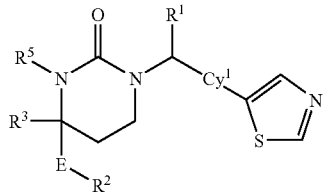

Iq$^6$

In Formulas Iq$^{1-5}$, the pyridine and thiazole rings in Formulas Iq$^{1-5}$ are optionally substituted (substitution at ring carbons bonded to hydrogen and ring nitrogen atoms bonded to hydrogen atoms are encompassed, i.e., a "substitutable ring nitrogen atom") with up to four substituents as described above for Cy$^2$. Suitable substituents for Cy$^2$ and suitable values for R$^1$, R$^2$, R$^3$, R$^5$, Cy$^1$ and E are as defined in any one of the first, second, third, fourth, fifth or sixth embodiments. Alternatively, —CHO, NH$_2$—SO$_2$NH$_2$, —COOH, and —CONH$_2$ are excluded as permissible substituents for the pyridine and thiazole rings at the position corresponding to Cy$^2$ for all of the specific embodiments described above for Formulas Iq$^{1-6}$. Alternatively, suitable substituents for Cy$^1$ and the pyridine and thiazole rings in Formulas Iq$^{1-6}$ are as described for G$^1$ and G$^2$, respectively, in Formula If, and values for R$^1$, R$^2$, R$^3$, R$^5$, Cy$^1$ and E are as defined in any one of the first, second, third, fourth, fifth or sixth embodiments. Alternatively, suitable substituents for Cy$^1$ include (C$_1$-C$_4$)alkyl, (C$_1$-C$_4$) alkoxy, (C$_1$-C$_4$)haloalkyl, (C$_1$-C$_4$)haloalkoxy, halogen, cyano and nitro; suitable substituents for a ring carbon atom in the pyridine and thiazole rings in Formulas Iq$^{1-6}$ include fluorine, chlorine, cyano, hydroxy, amino, (C$_1$-C$_4$)alkyl, (C$_3$-C$_4$)cycloalkyl, (C$_3$-C$_4$)cycloalkyl(C$_1$-C$_2$)alkyl, halo(C$_1$-C$_4$) alkyl, (C$_1$-C$_4$)alkoxy, (C$_1$-C$_4$)haloalkoxy, CONH$_2$, (C$_1$-C$_4$) alkylaminocarbonyl, di(C$_1$-C$_4$)alkylaminocarbonyl, (C$_3$-C$_4$) cycloalkylaminocarbonyl, {(C$_1$-C$_4$)alkyl}{(C$_3$-C$_4$) cycloalkyl}aminocarbonyl and (C$_1$-C$_4$)alkylcarbonylamino; the ring nitrogen in pyridines Iq$^{1-3}$ is optionally substituted by oxo; and suitable values for R$^1$, R$^2$, R$^3$, R$^5$, Cy$^1$ and E are as defined in any one of the first, second, third, fourth, fifth or sixth embodiments.

For each of the embodiment described in the previous paragraph, R$^1$ is preferably methyl or ethyl.

For each of the embodiment described in the paragraph immediately following Formulas Iq$^{1-6}$, R$^1$ is preferably methyl or ethyl; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiment described in the paragraph immediately following Formulas $Iq^{1-6}$, $R^1$ is preferably methyl or ethyl; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiment described in the paragraph immediately following Formulas $Iq^{1-5}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^a$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiment described in the paragraph immediately following Formulas $Iq^{1-6}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiment described in the paragraph immediately following Formulas $Iq^{1-6}$, $R^1$ is preferably methyl or ethyl; and $R^3$ is 2-hydroxy-2-methylpropyl or 2-cyano-2-methylpropyl.

For each of the embodiment described in the paragraph immediately following Formulas $Iq^{1-6}$, $R^1$ is preferably methyl or ethyl; $R^2$ is phenyl or fluorophenyl; and $R^3$ is 2-hydroxy-2-methylpropyl or 2-cyano-2-methylpropyl.

For each of the embodiment described in the paragraph immediately following Formulas $Iq^{1-6}$, $R^1$ is preferably methyl or ethyl; $R^2$ is phenyl or fluorophenyl; $R^3$ is 2-hydroxy-2-methylpropyl or 2-cyano-2-methylpropyl; one or two ring carbon atoms in the pyridine and thiazole rings in Formulas $Iq^{1-5}$ are optionally substituted with fluoro, chloro, cyano, $CONH_2$, $CONHMe$, $CONMe_2$, $CONHc$-Pr, methoxy, ethoxy, methyl, ethyl or $CF_3$, the ring nitrogen in the pyridine rings in Formulas $Iq^{1-3}$ is optionally substituted by oxo.

For each of the embodiments described in the paragraph immediately following Formulas $Iq^{1-6}$, $R^5$ is preferably hydrogen, methyl or ethyl. Specifically, $R^5$ is hydrogen or methyl.

Another embodiment of the invention is a compound of any one of Formulas $Ir^{1-6}$, or a pharmaceutically acceptable salt, enantiomer or diastereomer thereof:

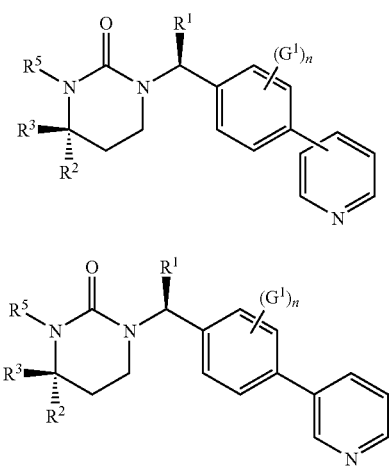

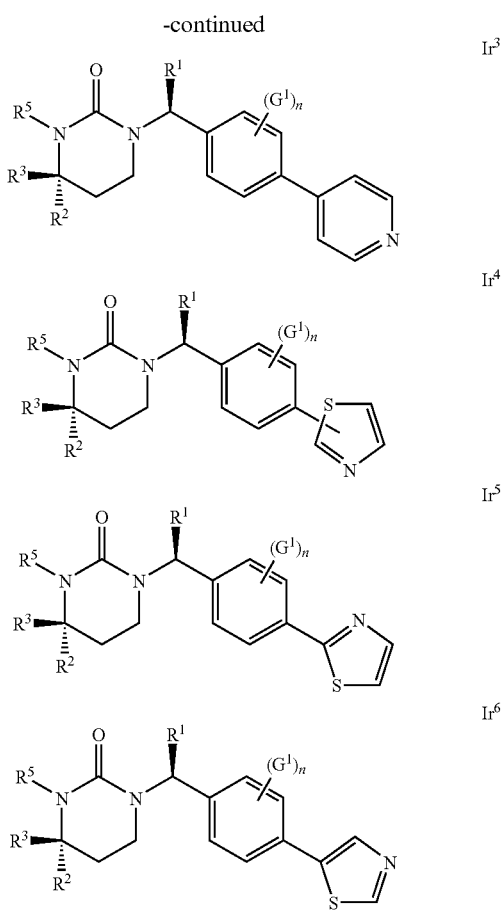

In Formulas $Ir^{1-6}$, the pyridine and thiazole rings in Formulas $Ir^{1-6}$ are optionally substituted (substitution at ring carbons bonded to hydrogen and ring nitrogen atoms bonded to hydrogen atoms are encompassed, i.e., a "substitutable ring nitrogen atom") with up to four substituents as described above for $Cy^2$. Alternatively, $—CHO$, $NH_2$—$SO_2NH_2$, $—COOH$, and $—CONH_2$ are excluded as permissible substituents for the pyridine and thiazole rings at the position corresponding to $Cy^2$ for all of the specific embodiments described above for Formulas $II^{1-6}$, and $Is^{1-2}$.

Suitable values for $G^1$ are as described in Formula If; n is 0, 1 or 2; substituents for $Cy^2$ and suitable values for $R^1$, $R^2$, $R^3$ and $R^5$ are as defined in any one of the first, second, third, fourth, fifth or sixth embodiments. Alternatively, n is 0, 1 or 2, suitable values for $G^1$ in Formulas $Ir^{1-6}$ and suitable substituents for the pyridine and thiazole rings in Formulas $Ir^{1-6}$ are as described for $G^1$ and $G^2$, respectively, in Formula If, and values for $R^1$, $R^2$, $R^3$ and $R^5$ are as defined in any one of the first, second, third, fourth, fifth or sixth embodiments. Alternatively, n is 0, 1 or 2; suitable values for $G^1$ include $(C_1-C_4)$alkyl, $(C_1-C_4)$alkoxy, $(C_1-C_4)$haloalkyl, $(C_1-C_4)$haloalkoxy, halogen, cyano and nitro; suitable substituents for a ring carbon atom in the pyridine and thiazole rings in Formulas $Ir^{1-6}$ include fluorine, chlorine, cyano, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl, $(C_3-C_4)$cycloalkylaminocarbonyl, $\{(C_1-C_4)$alkyl$\}\{(C_3-C_4)$cycloalkyl$\}$aminocarbonyl and $(C_1-C_4)$alkylcarbonylamino; the ring nitrogen in pyridines $Ir^{1-3}$ is optionally substituted by oxo; and suitable values for $R^1$, $R^2$, $R^3$ and $R^5$ are as defined in any one of the first, second, third, fourth, fifth or sixth embodiments.

For each of the embodiment described in the previous paragraph, $R^1$ is preferably methyl or ethyl.

For each of the embodiment described in the paragraph immediately following Formulas $Ir^{1-6}$, $R^1$ is preferably methyl or ethyl; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiment described in the paragraph immediately following Formulas $Ir^{1-6}$, $R^1$ is preferably methyl or ethyl; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiment described in the paragraph immediately following Formulas $Ir^{1-6}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiment described in the paragraph immediately following Formulas $Ir^{1-6}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiment described in the paragraph immediately following Formulas $Ir^{1-6}$, $R^1$ is preferably methyl or ethyl; and $R^3$ is 2-hydroxy-2-methylpropyl or 2-cyano-2-methylpropyl.

For each of the embodiment described in the paragraph immediately following Formulas $Ir^{1-6}$, $R^1$ is preferably methyl or ethyl; $R^2$ is phenyl or fluorophenyl; and $R^3$ is 2-hydroxy-2-methylpropyl or 2-cyano-2-methylpropyl.

For each of the embodiment described in the paragraph immediately following Formulas $Ir^{1-6}$, $R^1$ is preferably methyl or ethyl; $R^2$ is phenyl or fluorophenyl; $R^3$ is 2-hydroxy-2-methylpropyl or 2-cyano-2-methylpropyl; one or two ring carbon atoms in the pyridine and thiazole rings in Formulas $Ir^{1-6}$ are optionally substituted with fluoro, chloro, cyano, $CONH_2$, $CONHMe$, $CONMe_2$, $CONHc$-Pr, methyl, ethyl or $CF_3$, the ring nitrogen in the pyridine rings in Formulas $Ir^{1-3}$ is optionally substituted by oxo.

For each of the embodiments described in the paragraph immediately following Formulas $Ir^{1-6}$, $R^5$ is preferably hydrogen, methyl or ethyl. Specifically, $R^5$ is hydrogen or methyl.

Another embodiment of the invention is a compound represented by any one of Formulas $Is^{1-2}$, or a pharmaceutically acceptable salt thereof:

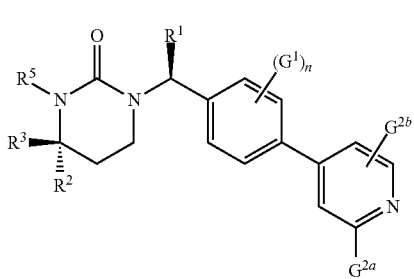

$Is^1$

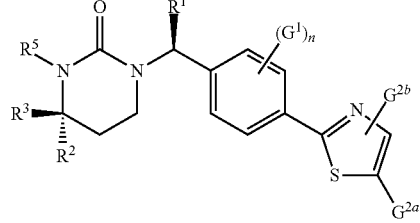

$Is^2$

In Formulas $Is^{1-2}$, $G^1$ is $(C_1-C_4)$alkyl, $(C_1-C_4)$alkoxy, $(C_1-C_4)$haloalkyl, $(C_1-C_4)$haloalkoxy, halogen, cyano and nitro; n is 0 1 or 2; $G^{2a}$ and $G^{2b}$ are independently selected from hydrogen, fluorine, chlorine, cyano, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl, $(C_3-C_4)$cycloalkylaminocarbonyl, $\{(C_1-C_4)$alkyl$\}\{(C_3-C_4)$cycloalkyl$\}$aminocarbonyl and $(C_1-C_4)$alkylcarbonylamino; $G^{2c}$ is $(C_1-C_4)$alkyl, $(C_3-C_4)$cycloalkyl or $(C_1-C_4)$haloalkyl; and suitable values for $R^1$, $R^2$, $R^3$ and $R^5$ are as defined in any one of the first, second, third, fourth, fifth or sixth embodiments. Alternatively, —CHO, $NH_2-SO_2NH_2$, —COOH, and —$CONH_2$ are excluded as permissible substituents for the pyridine and thiazole rings at the position corresponding to $Cy^2$ for all of the specific embodiments described above for Formulas $Is^{1-2}$.

For each of the embodiment described in the previous paragraph, $R^1$ is preferably methyl or ethyl.

For each of the embodiment described in the paragraph immediately following Formulas $Is^{1-2}$, $R^1$ is preferably methyl or ethyl; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiment described in the paragraph immediately following Formulas $Is^{1-2}$, $R^1$ is preferably methyl or ethyl; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiment described in the paragraph immediately following Formulas $Is^{1-2}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiment described in the paragraph immediately following Formulas $Is^{1-2}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $H_2NC(=O)CMe_2CH_2$, 3-hydroxy-3-methylbutyl, 2-hydroxyethyl, 2-hydroxy-2-methylpropyl or 2-cyano-2-methylpropyl.

For each of the embodiment described in the paragraph immediately following Formulas $Is^{1-2}$, $R^1$ is preferably methyl or ethyl; and $R^3$ is 2-hydroxy-2-methylpropyl or 2-cyano-2-methylpropyl.

For each of the embodiment described in the paragraph immediately following Formulas $Is^{1-2}$, $R^1$ is preferably methyl or ethyl; $R^2$ is phenyl or fluorophenyl; and $R^3$ is 2-hydroxy-2-methylpropyl or 2-cyano-2-methylpropyl.

For each of the embodiments described in the paragraph immediately following Formulas Is$^{1-2}$, R$^5$ is preferably hydrogen, methyl or ethyl. Specifically, R$^5$ is hydrogen or methyl.

Alternatively, —CHO, NH$_2$—SO$_2$NH$_2$, —COOH, and —CONH$_2$ are excluded as permissible substituents for the pyridine and thiazole rings at the position corresponding to Cy$^2$ for all of the specific embodiments described above for Formulas Ip$^{1-6}$, Iq$^{1-6}$, Ir$^{1-6}$ and Is$^{1-2}$.

The present invention further provides methods of inhibiting 11β-HSD1 by contacting 11β-HSD1 with a compound of Formula I, Ia, Ib, Ic, Id, Ie, If, Ig, Ih, Ij, Ik, Il$^{1-3}$. Im$^{1-3}$, In$^{1-3}$, Io$^{1-2}$, Ip$^{1-6}$, Ir$^{1-6}$ and Is$^{1-2}$ of the invention.

The present invention further provides methods of inhibiting or reducing the conversion of cortisone to cortisol in a cell using a compound of Formula I, Ia, Ib, Ic, Id, Ie, If, Ig, Ih, Ij, Ik, Il$^{1-3}$. Im$^{1-3}$, In$^{1-3}$, Io$^{1-2}$, Ip$^{1-6}$, Ir$^{1-6}$ and Is$^{1-2}$ is of the invention.

The present invention further provides methods of inhibiting or reducing production of cortisol in a cell using a compound of Formula I, Ia, Ib, Ic, Id, Ie, If, Ig, Ih, Ij, Ik, Il$^{1-3}$. Im$^{1-3}$, In$^{1-3}$, Io$^{1-2}$, Ip$^{1-6}$, Ir$^{1-6}$ and Is$^{1-2}$ of the invention.

The present invention further provides methods of increasing insulin sensitivity in a subject in need thereof using a compound of Formula I, Ia, Ib, Ic, Id, Ie, If, Ig, Ih, Ij, Ik, Il$^{1-3}$. Im$^{1-3}$, In$^{1-3}$, Io$^{1-2}$, Ip$^{1-6}$, Ir$^{1-6}$ and Is$^{1-2}$ of the invention.

The present invention further provides methods of treating a subject with a disease associated with activity of expression of 11β-HSD1 using a compound of Formula I, Ia, Ib, Ic, Id, Ie, If, Ig, Ih, Ij, Ik, Il$^{1-3}$. Im$^{1-3}$, In$^{1-3}$, Io$^{1-2}$, Ip$^{1-6}$, Ir$^{1-6}$ and Is$^{1-2}$ of the invention.

Alternative values for the variables in the above-described structural formulas I, Ia, Ib, Ic, Id, Ie, If, Ig, Ih, Ij, Ik, Il$^{1-3}$. Im$^{1-3}$, In$^{1-3}$, Io$^{1-2}$, Ip$^{1-6}$, Ir$^{1-6}$ and Is$^{1-2}$ are provided below:

A$^1$ is a bond. Alternatively, A$^1$ is (C$_1$-C$_3$)alkylene. In another specific embodiment, A$^1$ is methylene. In another specific embodiment, if R$^1$ is present, A$^1$ is CH.

R$^1$ is (a) absent or (b) is selected from (C$_1$-C$_6$)alkyl, (C$_2$-C$_6$)alkenyl, (C$_2$-C$_6$)alkynyl or (C$_1$-C$_3$)alkoxy(C$_1$-C$_3$)alkyl, wherein each is optionally substituted with up to four groups independently selected from fluorine, cyano, oxo, R$^4$, R$^4$O—, (R$^4$)$_2$N—, R$^4$O$_2$C—, R$^4$S, R$^4$S(=O)—, R$^4$S(=O)$_2$—, R$^4$C(=O)NR$^4$—, (R$^4$)$_2$NC(=O)—, (R$^4$)$_2$NC(=O)O—, (R$^4$)$_2$NC(=O)NR$^4$—, R$^4$OC(=O)NR$^4$—, (R$^4$)$_2$NC(=NCN)NR$^4$—, (R$^4$O)$_2$P(=O)O—, (R$^4$O)$_2$P(=O)NR$^4$—, R$^4$OS(=O)$_2$NR$^4$—, (R$^4$)$_2$NS(=O)$_2$O—, (R$^4$)$_2$NS(=O)$_2$NR$^4$—, R$^4$S(=O)$_2$NR$^4$—, R$^4$S(=O)$_2$NHC(=O)—, R$^4$S(=O)$_2$NHC(=O)O—, R$^4$S(=O)$_2$NHC(=O)NR$^4$—, R$^4$OS(=O)$_2$NHC(=O)—, R$^4$OS(=O)$_2$NHC(=O)O—, R$^4$OS(=O)$_2$NHC(=O)NR$^4$—, (R$^4$)$_2$NS(=O)$_2$NHC(=O)—, (R$^4$)$_2$NS(=O)$_2$NHC(=O)O—, (R$^4$)$_2$NS(=O)$_2$NHC(=O)NR$^4$—, R$^4$C(=O)NHS(=O)$_2$—, R$^4$C(=O)NHS(=O)$_2$O—, R$^4$C(=O)NHS(=O)$_2$NR$^4$—, R$^4$OC(=O)NHS(=O)$_2$—, R$^4$OC(=O)NHS(=O)$_2$O—, R$^4$OC(=O)NHS(=O)$_2$NR$^4$—, (R$^4$)$_2$NC(=O)NHS(=O)$_2$—, (R$^4$)$_2$NC(=O)NHS(=O)$_2$O—, (R$^4$)$_2$NC(=O)NHS(=O)$_2$NR$^4$—, aryl, cycloalkyl, heterocyclyl, heteroaryl, arylamino and heteroarylamino. Alternatively, R$^1$ is (a) absent or (b) is selected from (C$_1$-C$_6$)alkyl, (C$_2$-C$_6$)alkenyl, (C$_2$-C$_6$)alkynyl or (C$_1$-C$_3$)alkoxy(C$_1$-C$_3$)alkyl, wherein each is optionally substituted with up to four groups independently selected from fluorine, cyano, oxo, R$^4$, R$^4$O—, (R$^4$)$_2$N—, R$^4$O$_2$C—, R$^4$S, R$^4$OC(=O)NR$^4$—, (R$^4$)$_2$NC(=NCN)NR$^4$—, (R$^4$O)$_2$P(=O)O—, (R$^4$O)$_2$P(=O)NR$^4$—, R$^4$OS(=O)$_2$NR$^4$—, (R$^4$)$_2$NS(=O)$_2$O—, (R$^4$)$_2$NS(=O)$_2$NR$^4$—, R$^4$S(=O)$_2$NR$^4$—, R$^4$S(=O)$_2$NHC(=O)—, R$^4$S(=O)$_2$NHC(=O)O—, R$^4$S(=O)$_2$NHC(=O)NR$^4$—, R$^4$OS(=O)$_2$NHC(=O)—, R$^4$OS(=O)$_2$NHC(=O)O—, R$^4$OS(=O)$_2$NHC(=O)NR$^4$—, (R$^4$)$_2$NS(=O)$_2$NHC(=O)—, (R$^4$)$_2$NS(=O)$_2$NHC(=O)O—, (R$^4$)$_2$NS(=O)$_2$NHC(=O)NR$^4$—, R$^4$C(=O)NHS(=O)$_2$—, R$^4$C(=O)NHS(=O)$_2$O—, R$^4$C(=O)NHS(=O)$_2$NR$^4$—, R$^4$OC(=O)NHS(=O)$_2$—, R$^4$OC(=O)NHS(=O)$_2$O—, R$^4$OC(=O)NHS(=O)$_2$NR$^4$—, (R$^4$)$_2$NC(=O)NHS(=O)$_2$—, (R$^4$)$_2$NC(=O)NHS(=O)$_2$O—, (R$^4$)$_2$NC(=O)NHS(=O)$_2$NR$^4$—, heterocyclyl, heteroaryl, arylamino and heteroarylamino. In another alternative, R$^1$ is (C$_1$-C$_6$)alkyl. Alternatively, R$^1$ is methyl or ethyl.

Cy$^1$ is optionally substituted aryl or optionally substituted heteroaryl. Alternatively, Cy$^1$ is optionally substituted phenyl or optionally substituted pyridyl. In another alternative, Cy$^1$ is optionally substituted monocyclic cycloalkyl. In another alternative, Cy$^1$ is optionally substituted cyclohexyl. In another alternative, Cy$^1$ is optionally substituted phenyl. In yet another specific embodiment, Cy$^1$ is substituted with fluorine chlorine, bromine, methoxy, methoxycarbonyl, carboxy, or methyl. In yet another specific embodiment, Cy$^1$ is substituted with fluorine or bromine. In another embodiment A$^2$ is a bond, Cy$^2$ is H and Cy$^1$ is optionally substituted monocyclic cycloalkyl. In another embodiment A$^2$ is a bond, Cy$^2$ is H and Cy$^1$ is optionally substituted cyclohexyl. In another embodiment A$^2$ is a bond, Cy$^2$ is H and Cy$^1$ is phenyl substituted with fluorine, chlorine, bromine, methyl, methoxy, methoxycarbonyl, trifluoromethyl, hydroxymethyl, 2-hydroxy-2-propyl, trifluoromethoxy or difluoromethoxy.

A$^2$ is a bond and Cy$^2$ is hydrogen. Alternatively, A$^2$ is a bond and Cy$^2$ is cyclopropyl. Alternatively, A$^2$ is a bond and Cy$^2$ is optionally substituted aryl or optionally substituted heteroaryl. In another specific embodiment, A$^2$ is a bond and Cy$^2$ is optionally substituted phenyl or optionally substituted pyridyl. In yet another specific embodiment, A$^2$ is a bond and Cy$^2$ is optionally substituted phenyl. In yet another specific embodiment, A$^2$ is a bond and Cy$^2$ is substituted with 1 to 4 groups independently selected from chlorine or fluorine. In yet another specific embodiment, A$^2$ is a bond and Cy$^2$ is difluorophenyl. In yet another specific embodiment, A$^2$ is a bond and Cy$^2$ is fluorophenyl. In yet another specific embodiment A$^2$ is a bond and Cy$^2$ is optionally substituted 2-thienyl, 1-pyrazolyl, 3-pyrazolyl, 1,2,4-thiadiazol-3-yl, thiazolyl or 2-oxo-1,2-dihydro-5-pyridyl. In yet another specific embodiment, A$^2$ is a bond and Cy$^2$ is phenyl or thienyl substituted with amino(C$_1$-C$_6$)alkyl. In yet another specific embodiment, Cy$^2$ is 2-oxo-1,2-dihydro-4-pyridyl.

In a specific embodiment E is a bond. In another specific embodiment, E is a bond when R$^2$ is optionally substituted aryl, optionally substituted heteroaryl or optionally substituted cycloalkyl. In another specific embodiment, E is a bond when R$^2$ is optionally substituted phenyl, optionally substituted thienyl or optionally substituted pyridyl. In yet another specific embodiment, E is a bond when R$^2$ is optionally substituted phenyl.

R$^3$ is hydroxy(C$_2$-C$_4$)alkyl. In yet another specific embodiment R$^3$ is 3-hydroxypropyl, 2-hydroxypropyl or 2-hydroxyethyl. Alternatively, R$^3$ is dihydroxy(C$_3$-C$_4$)alkyl. In yet another specific embodiment R$^3$ is 2,3-dihydroxypropyl. In another specific embodiment, R$^3$ is ω-H$_2$NCO(C$_1$-C$_3$)alkyl. In yet another specific embodiment R$^3$ is H$_2$NC(=O)CH$_2$CH$_2$—. In yet another specific embodiment, R$^3$ is (C$_1$-C$_2$)alkoxy(C$_1$-C$_3$)alkyl. In yet another specific embodiment, R$^3$ is H$_2$NSO$_2$O(C$_2$-C$_4$)alkyl. In yet another specific embodiment, R$^3$ is H$_2$NSO$_2$NH(C$_2$-C$_4$)alkyl. In yet another specific embodiment, R$^3$ is oxo(C$_2$-C$_4$)alkyl. In yet another specific embodiment, R$^3$ is MeCOCH$_2$. In yet another specific embodiment, R$^3$ is alkenyl. In yet another specific embodiment, $R^3$ is allyl. In yet another specific embodiment, $R^3$ is MeC(=O)NH($C_2$-$C_4$)alkyl. In yet another specific embodiment, $R^3$ is MeOC(=O)NH($C_2$-$C_4$)alkyl. In yet another specific embodiment, $R^3$ is cyanoalkyl. In yet another specific embodiment, $R^3$ is alkylsulfonylaminoalkyl. In yet another specific embodiment $R^3$ is MeSO$_2$NH($C_2$-$C_4$)alkyl. In yet another specific embodiment $R^3$ is MeSO$_2$NHCH$_2$CH$_2$—. In yet another specific embodiment, $R^3$ is hydroxyalkoxyalkyl. In yet another specific embodiment $R^3$ is alkylhydroxyalkyl. In yet another specific embodiment, $R^3$ is aminocarbonylaminoalkyl. In yet another specific embodiment, $R^3$ is aminocarboxyalkyl. In yet another specific embodiment $R^3$ is 2-(4-morpholino)ethyl. In yet another specific embodiment $R^3$ is 2-(1-imidazolyl)ethyl. In yet another specific embodiment, $R^3$ is 2-hydroxy-2-methylpropyl, (1-hydroxycyclopropyl)methyl, 2-cyano-2-methylpropyl or H$_2$NC(=O)CMe$_2$CH$_2$.

$R^2$ is optionally substituted aryl, optionally substituted heteroaryl or cycloalkyl or alkyl. In one specific embodiment, $R^2$ is optionally substituted phenyl, optionally substituted pyridyl or optionally substituted thienyl. In another embodiment, $R^2$ is optionally substituted alkyl. In one specific embodiment, $R^2$ is optionally substituted isopropyl. In another specific embodiment, $R^2$ is optionally substituted phenyl. In yet another specific embodiment, $R^2$ is fluorophenyl.

$R^5$ is hydrogen or methyl. In one specific embodiment, $R^5$ is hydrogen.

In another embodiment of the invention, the provisos applied to pharmaceutical compositions comprising compounds of Formula I also apply to methods of treatment utilizing any one of the compounds of Formula I or Formulas Ia-Ig.

DEFINITIONS

The term "alkyl" means a straight or branched hydrocarbon radical having 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "cycloalkyl" means a monocyclic, bicyclic or tricyclic, saturated hydrocarbon ring having 3-10 carbon atoms and includes, for example, cyclopropyl, cyclobutyl, cyclopentyl, cyclohexyl, cycloheptyl, cyclooctyl, bicyclo[2.2.2]octyl, bicyclo[2.2.1]heptyl, spiro[4.4]nonane, adamantyl and the like.

The term "aryl" means an aromatic radical which is a phenyl group, a naphthyl group, an indanyl group or a tetrahydronaphthalene group. An aryl group is optionally substituted with 1-4 substituents. Exemplary substituents include alkyl, alkoxy, alkylthio, alkylsulfonyl, halogen, trifluoromethyl, dialkylamino, nitro, cyano, CO$_2$H, CONH$_2$, N-monoalkyl-substituted amido and N,N-dialkyl-substituted amido.

The term "heteroaryl" means a 5- and 6-membered heteroaromatic radical which may optionally be fused to a saturated or unsaturated ring containing 0-4 heteroatoms selected from N, O, and S and includes, for example, a heteroaromatic radical which is 2- or 3-thienyl, 2- or 3-furanyl, 2- or 3-pyrrolyl, 2-, 3-, or 4-pyridyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, 5-, 6-, 7- or 8-quinazolinyl, 2-, 3-, 5-, 6-, 7- or 8-quinoxalinyl, 2-, 3-, 4-, 5-, 6-, 7- or 8-quinolinyl, 1-, 3-, 4-, 5-, 6-, 7- or 8-isoquinolinyl, 2-, 4-, or 5-thiazolyl, 2-, 3-, 4-, or 5-pyrazolyl, 2-, 3-, 4-, or 5-imidazolyl. A heteroaryl is optionally substituted. Exemplary substituents include alkyl, alkoxy, alkylthio, alkylsulfonyl, halogen, trifluoromethyl, dialkylamino, nitro, cyano, CO$_2$H, CONH$_2$, N-monoalkyl-substituted amido and N,N-dialkyl-substituted amido, or by oxo to form an N-oxide.

The term "heterocyclyl" means a 4-, 5-, 6- and 7-membered saturated or partially unsaturated heterocyclic ring containing 1 to 4 heteroatoms independently selected from N, O, and S. Exemplary heterocyclyls include pyrrolidine, pyrrolidin-2-one, 1-methylpyrrolidin-2-one, piperidine, piperidin-2-one, 2-pyridone, 4-pyridone, piperazine, 1-(2,2,2-trifluoroethyl)piperazine, piperazin-2-one, 5,6-dihydropyrimidin-4-one, pyrimidin-4-one, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide and isothiazolidine 1,1-dioxide. A heterocyclyl can be optionally substituted with 1-4 substituents. Exemplary substituents include alkyl, haloalkyl and oxo.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R" and "S" denote the relative configurations of substituents around one or more chiral carbon atoms.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

"R," "S," "St," "R*," "E," "Z," "cis," and "trans," indicate configurations relative to the core molecule.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has at least one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphosphate, polygalacturonate, salicylate, stearate, subacetate, succinate, sulfate, hydrogensulfate, tannate, tartrate, teoclate, tosylate, and triethiodide salts.

Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

The following abbreviations have the indicated meanings:

| Abbreviation | Meaning |
| --- | --- |
| Boc | tert-butoxy carbonyl or t-butoxy carbonyl |
| (Boc)$_2$O | di-tert-butyl dicarbonate |
| Cbz | Benzyloxycarbonyl |
| CbzCl | Benzyl chloroformate |
| DAST | diethylaminosulfur trifluoride |
| DBU | 1,8-diazabicyclo[5.4.0]undec-7-ene |

-continued

| Abbreviation | Meaning |
| --- | --- |
| DCC | N,N'-dicyclohexylcarbodiimide |
| DCU | N,N'-dicyclohexylurea |
| DIAD | diisopropyl azodicarboxylate |
| DIEA | N,N-diisopropylethylamine |
| DMAP | 4-(dimethylamino)pyridine |
| DMF | N,N-dimethylformamide |
| DMPU | 1,3-dimethyl-3,4,5,6-tetrahydro-2(1H)-pyrimidinone |
| 2,4-DNP | 2,4-dinitrophenylhydrazine |
| DPTBS | Diphenyl-t-butylsilyl |
| EDC•HCl, EDCl | 1-[3-(dimethylamino)propyl]-3-ethylcarbodiimide hydrochloride |
| Equiv | equivalents |
| Fmoc | 1-[[(9H-fluoren-9-ylmethoxy)carbonyl]oxy]- |
| Fmoc-OSu | 1-[[(9H-fluoren-9-ylmethoxy)carbonyl]oxy]-2,5-pyrrolidinedione |
| h, hr | hour(s) |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1H-Benzotriazol-1-yl)-1,1,3,3-tetramethyluronium hexafluorophosphate |
| KHMDS | potassium hexamethyldisilazane |
| LAH or LiAlH$_4$ | lithium aluminum hydride |
| LC-MS | liquid chromatography-mass spectroscopy |
| LHMDS | lithium hexamethyldisilazane |
| Me | methyl |
| MsCl | methanesulfonyl chloride |
| Min | minute |
| MS | mass spectrum |
| NaH | sodium hydride |
| NaHCO$_3$ | sodium bicarbonate |
| NaN$_3$ | sodium azide |
| NaOH | sodium hydroxide |
| Na$_2$SO$_4$ | sodium sulfate |
| NMM | N-methylmorpholine |
| NMP | N-methylpyrrolidinone |
| Pd$_2$(dba)$_3$ | tris(dibenzylideneacetone)dipalladium(0) |
| PE | petroleum ether |
| Quant | quantitative yield |
| Satd | saturated |
| SOCl$_2$ | thionyl chloride |
| SFC | supercritical fluid chromatography |
| SPA | scintillation proximity assay |
| SPE | solid phase extraction |
| TBAF | tetrabutylammonium fluoride |
| TBS | t-butyldimethylsilyl |
| TBDPS | t-butyldiphenylsilyl |
| TBSCl | t-butyldimethylsilyl chloride |
| TBDPSCl | t-butyldiphenylsilyl chloride |
| TEA | triethylamine or Et$_3$N |
| TEMPO | 2,2,6,6-tetramethyl-1-piperidinyloxy free radical |
| Teoc | 1-[2-(trimethylsilyl)ethoxycarbonyloxy]- |
| Teoc-OSu | 1-[2-(trimethylsilyl)ethoxycarbonyloxy]pyrrolidin-2,5-dione |
| TFA | trifluoroacetic acid |
| Tlc, TLC | thin layer chromatography |
| TMS | trimethylsilyl |
| TMSCl | chlorotrimethylsilane or trimethylsilyl chloride |
| t$_R$ | retention time |
| TsOH | p-toluenesulfonic acid |

General Description of Synthetic Methods

Compounds of Formula I can be prepared by several processes. In the discussion below, $A^1$, $A^2$, $Cy^1$, $Cy^2$, E, $R^1$, $R^2$, $R^3$, $R^5$, Y and n have the meanings indicated above unless otherwise noted. In cases where the synthetic intermediates and final products of Formulas I described below contain potentially reactive functional groups, for example amino, hydroxyl, thiol and carboxylic acid groups, that may interfere with the desired reaction, it may be advantageous to employ protected forms of the intermediate. Methods for the selection, introduction and subsequent removal of protecting groups are well known to those skilled in the art. (T. W.

Greene and P. G. M. Wuts "Protective Groups in Organic Synthesis" John Wiley & Sons, Inc., New York 1999). Such protecting group manipulations are assumed in the discussion below and not described explicitly. Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

In a first process a compound of Formula I, wherein can be prepared by reaction of a diamine intermediate of Formula II with a reagent of Formula III, wherein $Z^1$ and $Z^2$ are leaving groups such as chloride, 1-imidazolyl or aryloxide in an inert solvent such as THF, $CH_2Cl_2$, toluene or MeCN, usually in the presence of an organic or inorganic base such as triethylamine or $NaHCO_3$ respectively, at $-10°$ C. to $120°$ C.:

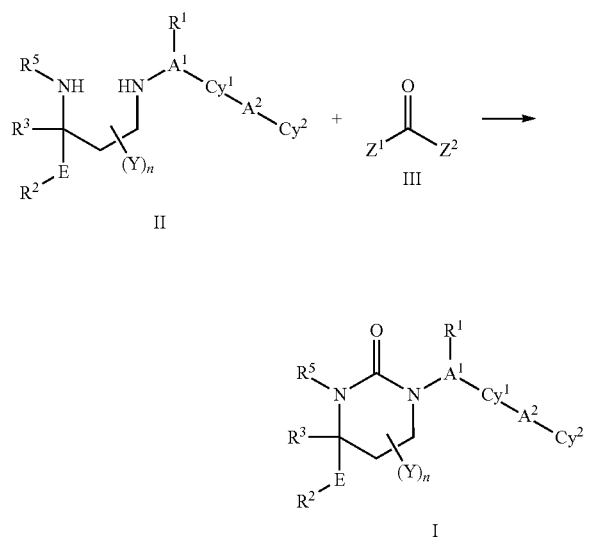

Certain instances of reagent III are especially convenient because they are commercially available. For example when $Z^1$ and $Z^2$ are both chloride, III is phosgene. When $Z^1$ and $Z^2$ are both 1-imidazolyl, III is carbonyl diimidazole. When $Z^1$ is chloride and $Z^2$ is p-nitrophenoxide, III is p-nitrophenyl chloroformate. When $Z^1$ and $Z^2$ are both $OCCl_3$, III is triphosgene and as little as one third of molar equivalent can be used.

Diamine intermediates of Formula II can be prepared by reduction of amides of Formula IV using a hydride reagent such as $BH_3.THF$ solution, $BH_3.Me_2S$ or $LiAlH_4$ in an inert solvent ethereal such as THF or DME at $20°$ C. to $100°$ C. for between 1 h and 48 h:

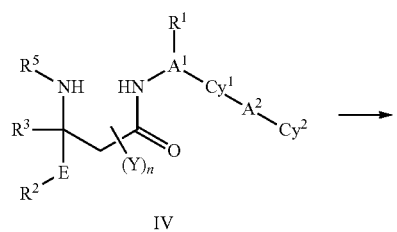

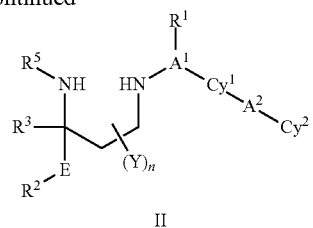

Intermediates of Formula IV can be prepared by coupling of a β-aminoacid of Formula V with an amine of Formula VI using standard peptide coupling reagents such as EDC in the presence of HOBt and N,N-diisopropylethylamine in an inert solvent such as $CH_2Cl_2$ at $0-30°$ C. for between 1 h and 24 h:

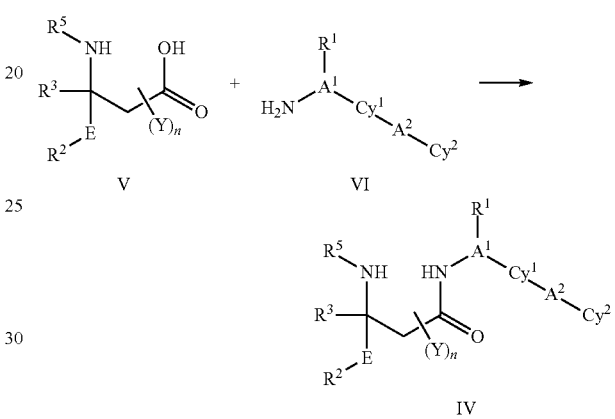

Methods for the synthesis β-aminoacids have been reviewed (Enantioselective Synthesis of β-Amino Acids (2nd Edition) (2005), Publisher: John Wiley & Sons, Inc., Hoboken, N.J). One method for the synthesis of a compound of Formula V', wherein Y is $(C_1-C_6)$alkyl group, attached as shown, $R^5$ is H and n is 0, 1 or 2, is the addition of the enolate of an ester of Formula VIII, wherein $R^a$ is $(C_1-C_6)$alkyl, to a sulfinylimine of Formula VII to give a compound of Formula IX, followed by ester hydrolysis and removal of the t-butylsulfinyl group:

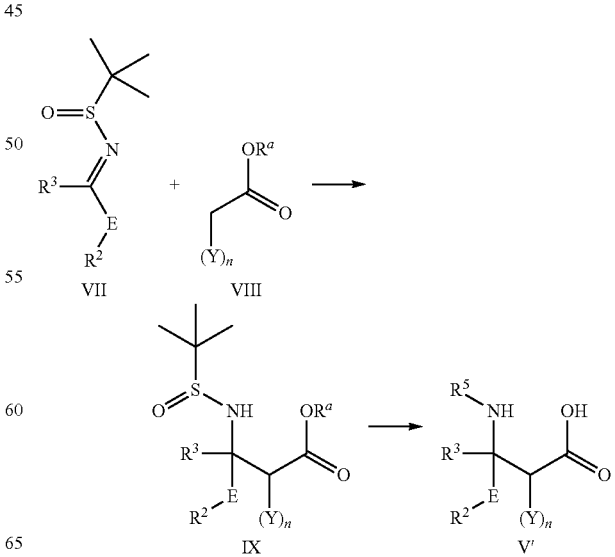

Amine intermediates of Formula VI, wherein $A^1=CH_2$ and $R^1$ is absent, can be prepared by reduction of amides of Formula X using a hydride reagent such as $BH_3.THF$ solution, $BH_3.Me_2S$ or $LiAlH_4$ in an inert solvent ethereal such as THF or DME at 20° C. to 100° C. for between 1 h and 48 h:

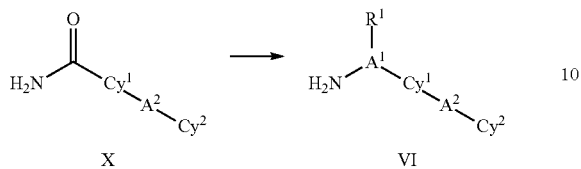

Amine intermediates of Formula VI, wherein $A^1$ is a bond, $R^1$ is absent and $Cy^1$ is not an aromatic or heteroaromatic ring, can be prepared from ketones of formula XI via oximes of Formula XII or by reductive amination of a ketone of Formula XI with ammonia:

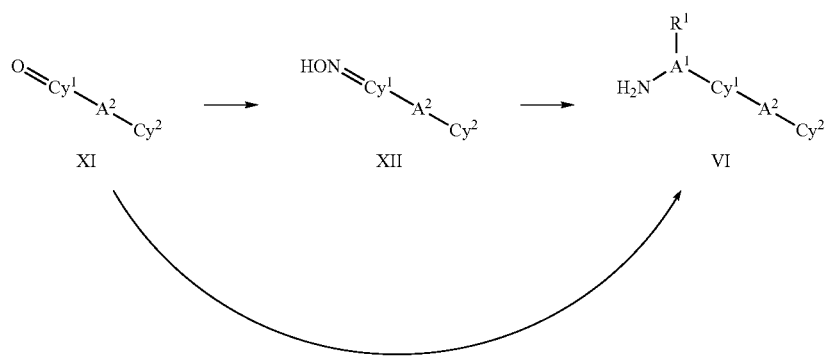

Methods for the conversion of ketones to oximes are described in Smith, M. B. and March, J. "March's Advanced Organic Chemistry" pp 1194-1195, 5th Edition, Wiley, New York, N.Y., 2001. Methods for the reduction of oximes to primary amines are described in Smith, M. B. and March, J. "March's Advanced Organic Chemistry" p 1555, 5th Edition, Wiley, New York, N.Y., 2001. Methods for the reductive amination of ketones are described in Baxter, E. W. and Reitz, A. B. "Organic Reactions" Volume 59, Ed. Overman, L. E., Wiley Interscience, 2002.

Intermediates of Formula II, wherein $A^1=CH_2$ and $R^1$ is absent, can be prepared by reduction of amide intermediates of formula XIII using a hydride reagent such as $BH_3.THF$ solution, $BH_3.Me_2S$ or $LiAlH_4$ in an inert solvent ethereal such as THF or DME at 20° C. to 100° C. for between 1 h and 48 h:

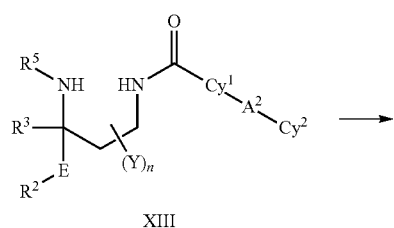

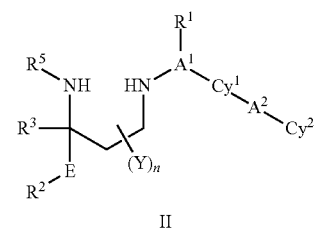

Amide intermediates of Formula XIII can be prepared by reaction of diamine intermediate of Formula XIV with an activated carboxylic acid of Formula XV wherein $Z^3$ is chloride or an activated ester, such as an N-hydroxysuccinimide ester:

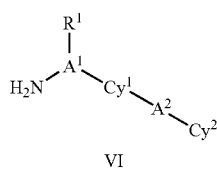

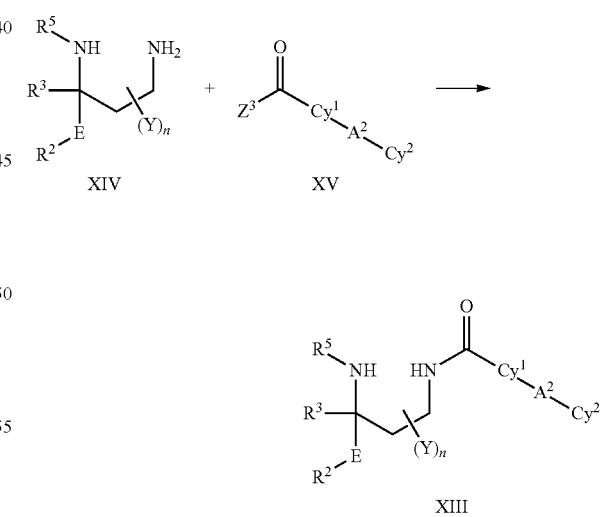

Diamine intermediates of Formula XIV, wherein n=0 and $R^5$=H, can be prepared by reaction of an aziridine of Formula XVI, wherein $R^b$ is a suitable amine protecting group such as t-butoxycarbonyl, with cyanide ion followed by deprotection to give a β-aminonitrile of Formula XVII followed by reduction with hydrogen gas in the presence of a catalyst or with a hydride source such as $LiAlH_4$:

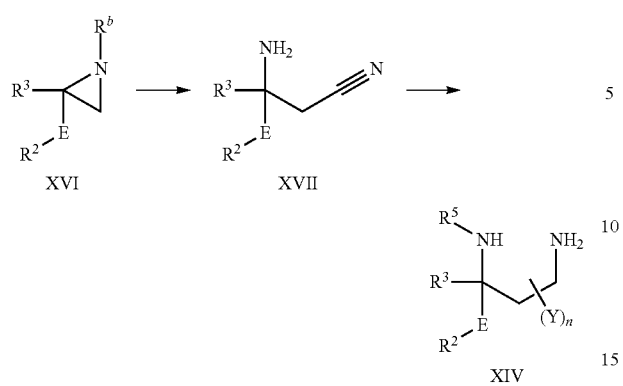

Diamine intermediates of Formula XIV, wherein n is 0, can be prepared by treatment of sulfonate intermediates of Formula XIX, wherein $R^c$ is for example methyl, trifluoromethyl or p-methylphenyl, with (i) ammonia or (ii) with $NaN_3$ followed by reduction using $PPh_3$ in wet THF or $H_2$ gas and a palladium catalyst:

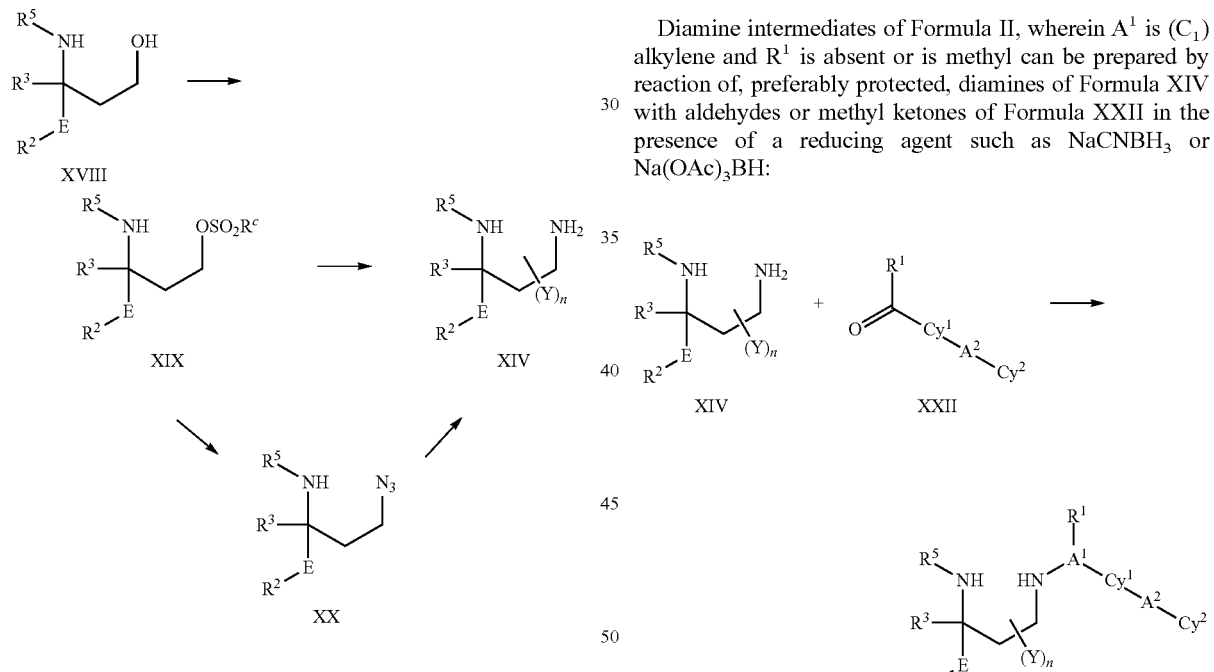

Sulfonate intermediates of Formula XIX are prepared by reaction of, preferably N-protected, alcohol intermediates Formula XVIII with $R^cSO_2Cl$ or $(R^cSO_2)_2O$. In addition sulfonate intermediates of Formula XIX can be reacted with amines of Formula VI to afford diamine intermediates of Formula II:

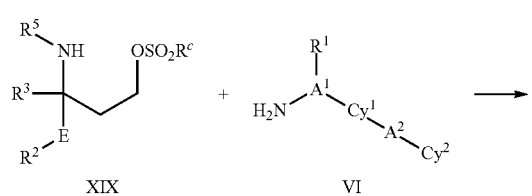

Aminoalcohol intermediates of Formula XVIII can be prepared by hydroboration of allylic amines of Formula XXI:

Diamine intermediates of Formula II, wherein $A^1$ is $(C_1)$ alkylene and $R^1$ is absent or is methyl can be prepared by reaction of, preferably protected, diamines of Formula XIV with aldehydes or methyl ketones of Formula XXII in the presence of a reducing agent such as $NaCNBH_3$ or $Na(OAc)_3BH$:

Methods for the reductive amination of aldehydes and ketones are described in Baxter, E. W. and Reitz, A. B. "Organic Reactions" Volume 59, Ed. Overman, L. E., Wiley Interscience, 2002.

In a second process a compound of Formula I can be prepared by treatment of an aminocarbamate of Formula XXIII, wherein $R^d$ is an alkyl or arylalkyl group such as methyl, t-butyl or benzyl, with a strong base such as sodium hydride:

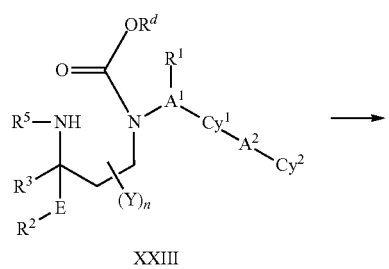

XXIII

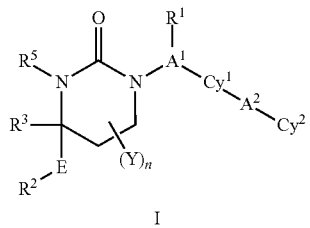

I

Aminocarbamates of Formula XXIII, wherein $R^5$ is H, can be prepared by reaction of iminocarbamates of Formula XXIV, wherein $R^d$ is an alkyl or arylalkyl group such as methyl, t-butyl or benzyl, with organometallic reagents of Formula XXV, wherein M is Li, MgCl, MgBr and MgI, followed by removal of the t-butylsulfinyl group:

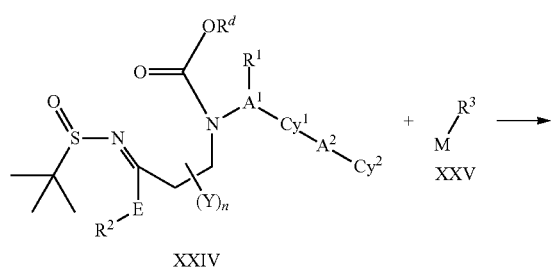

XXIV

XXIII

Alternatively, aminocarbamates of Formula XXIII, wherein $R^5$ is H, can be prepared by reaction of iminocarbamates of Formula XXVI, wherein $R^d$ is an alkyl or arylalkyl group such as methyl, t-butyl or benzyl, with organometallic reagents of Formula XXVII, wherein M is Li, MgCl, MgBr and MgI, followed by removal of the t-butylsulfinyl group:

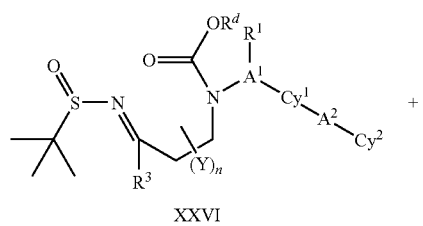

XXVI

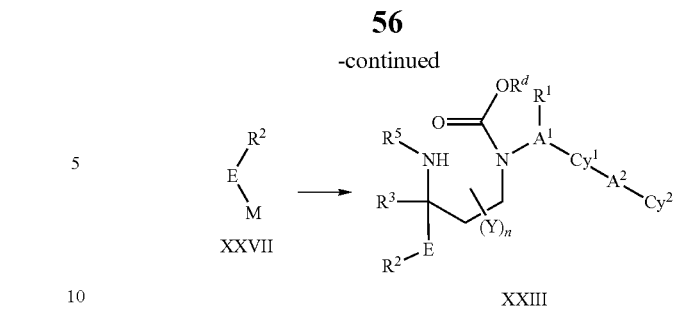

XXVII

XXIII

Iminocarbamates of Formula XXIV can be prepared by reaction of ketocarbamates of Formula XXVIII with 2-methylpropane-2-sulfinamide:

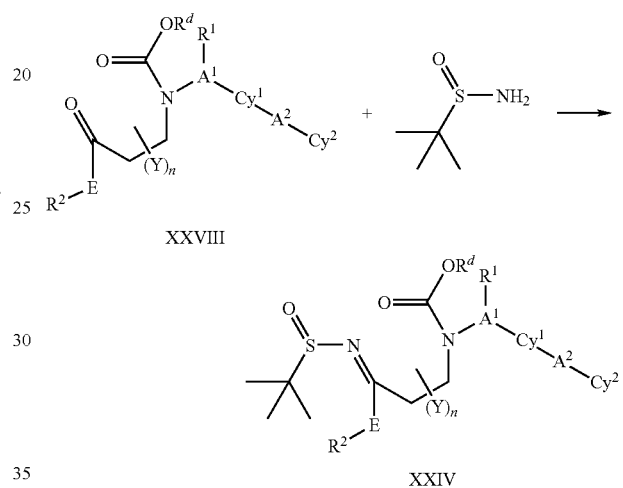

XXVIII

XXIV

Ketocarbamates of Formula XXVIII can be prepared by reaction of aminoketones of Formula XXIX with intermediates of Formula XXX wherein $R^e$ is a leaving group such as chloride, succinyloxy, imidazolyl or t-butoxycarboxycarbonyl:

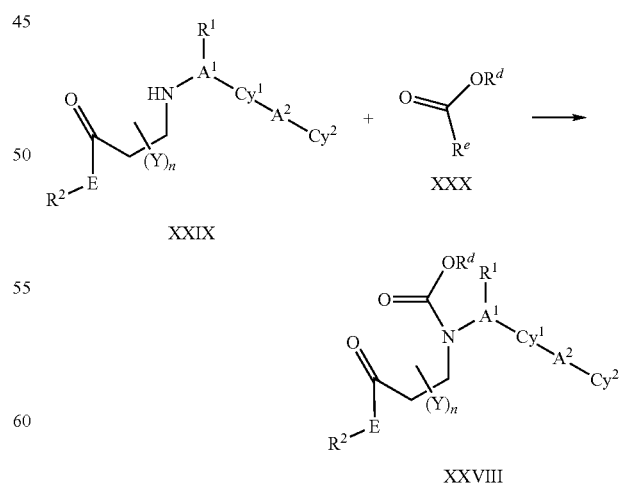

XXIX

XXX

XXVIII

Aminoketones of Formula XXIX, wherein n=0, can be prepared by reaction of α,β-unsaturated ketones of Formula XXXI with amines of Formula VI:

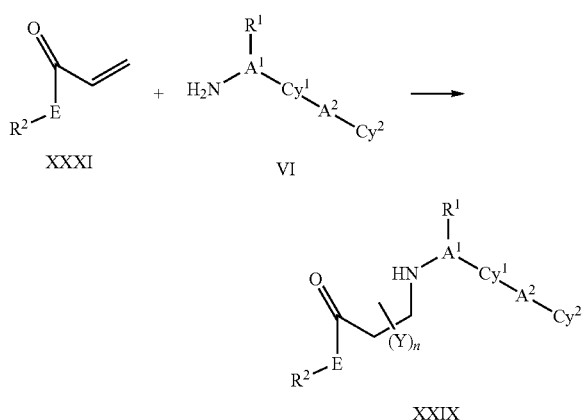

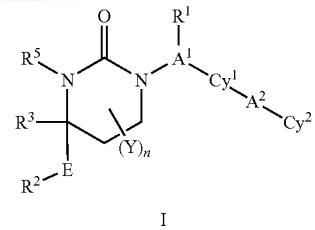

Compounds of Formula XXIII can be prepared by treatment of compounds of Formula XIV with various reagents of Formula III, wherein $Z^1$ and $Z^2$ are leaving groups such as chloride, 1-imidazolyl or aryloxide in an inert solvent such as THF, $CH_2Cl_2$, toluene or MeCN, usually in the presence of an organic or inorganic base such as triethylamine or $NaHCO_3$ respectively, at $-10°$ C. to $120°$ C.:

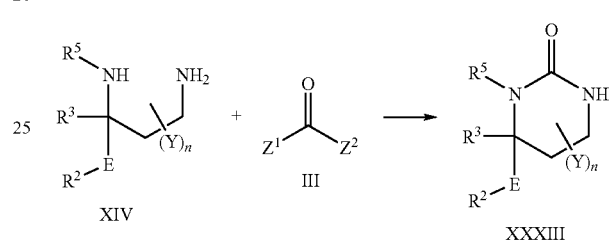

Aminoketones of Formula XXIX, wherein n=0, can also be prepared by reaction of β-dialkylaminoketones of Formula XXXII, wherein $R^f$ is lower alkyl especially methyl, with amines of Formula VI:

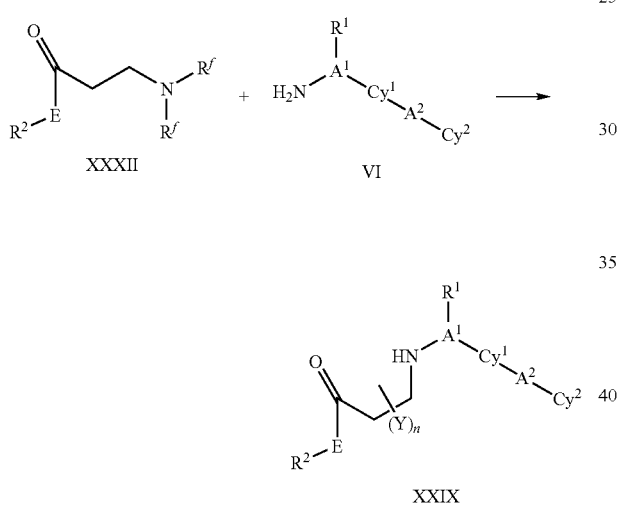

In a fourth process a compound of Formula I, wherein A is a bond can be prepared by reaction of a compound of Formula XXXIII, with a compound of Formula XXXV, wherein $R^g$ is a leaving group such as chloro, bromo, iodo or $OSO_2CF_3$, in the presence of a base such as $K_2CO_3$ and a copper or palladium catalyst in an inert solvent such as dioxane, DMF or NMP at elevated temperature:

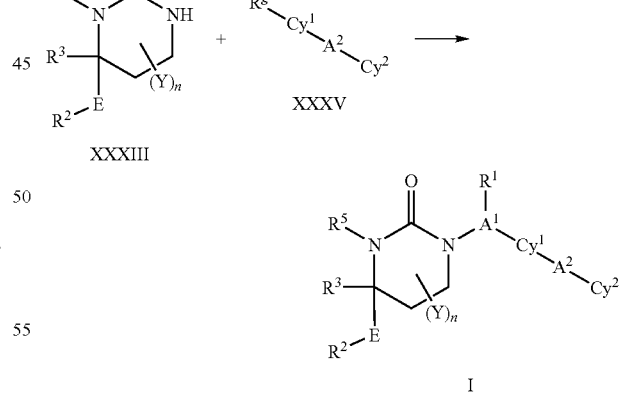

β-Dialkylaminoketones of Formula XXXII are in turn derived from α,β-unsaturated ketones of Formula XXXI with dialkylamines of Formula $R^fNHR^f$.

In a third process a compound of Formula I, wherein $A^1$ is $CH_2$ or $CH_2CH_2$ and $R^1$ is absent, can be prepared by reaction of a compound of Formula XXXIII, with a compound of Formula XXXIV, wherein $A^1$ is $CH_2$ or $CH_2CH_2$ and $R^g$ is a leaving group such as Br, I, $OSO_2Me$, $OSO_2CF_3$ or $OSO_2Ph$, in the presence of a base such as NaH or $K_2CO_3$:

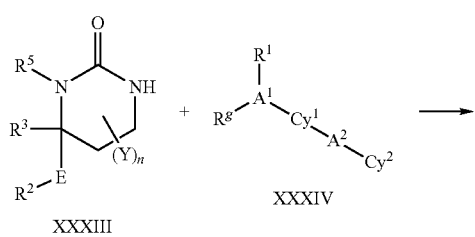

In a fifth process a compound of Formula I can be prepared from another compound of Formula I. For example:

(1) a compound of Formula I wherein $Cy^1$ is substituted with bromine or iodine, $A^2$ is a bond and $Cy^2$ is hydrogen can be reacted with an optionally substituted aryl or heteroarylboronic acid or ester in the presence of a palladium catalyst to give a compound of Formula I wherein $A^2$ is a bond and $Cy^2$ is optionally substituted aryl or heteroaryl.

(2) a compound of Formula I wherein $R^1$ or $R^3$ is ω-hydroxy($C_2$-$C_6$)alkyl can be oxidized to a compound of Formula I wherein $R^1$ or $R^3$ is ω-carboxy($C_1$-$C_3$)alkyl using Jones reagent.

(3) a compound of Formula I wherein $R^1$ or $R^3$ is ω-carboxy($C_1$-$C_6$)alkyl can be coupled with ammonia or a ($C_1$-$C_6$) alkylamine using a standard peptide coupling reagent such as EDC to afford a compound of Formula I wherein $R^1$ or $R^3$ is ω-$H_2$NC(=O)($C_1$-$C_6$)alkyl or ω-{($C_1$-$C_3$)alkylNHC(=O)}($C_1$-$C_6$)alkyl.

(4) a compound of Formula I wherein $R^1$ or $R^3$ is ω-hydroxy($C_1$-$C_6$)alkyl can be converted to its methanesulfonate or trifluoromethanesulfonate, treated with sodium azide and reduced to give a compound of Formula I, wherein $R^1$ or $R^3$ is ω-amino($C_1$-$C_3$)alkyl.

(5) a compound of Formula I wherein $R^1$ or $R^3$ is amino ($C_1$-$C_6$)alkyl can be reacted with acetic anhydride or acetyl chloride to give a compound of Formula I wherein $R^1$ or $R^3$ is {acetylamino}($C_1$-$C_6$)alkyl.

(6) a compound of Formula I wherein $R^1$ or $R^3$ is amino ($C_1$-$C_6$)alkyl can be reacted with methanesulfonyl chloride to give a compound of Formula I wherein $R^1$ or $R^3$ is {methanesulfonylamino}($C_1$-$C_6$)alkyl.

(7) a compound of Formula I, wherein $R^1$ is ($C_2$-$C_6$)alkenyl is hydroborated to afford a compound of Formula I wherein $R^1$ is hydroxy($C_2$-$C_6$)alkyl, (8) a compound of Formula I, wherein $R^3$ is ($C_2$-$C_6$)alkenyl, is hydroborated to afford a compound of Formula I wherein $R^3$ is hydroxy($C_2$-$C_6$)alkyl.

(9) a compound of Formula I, wherein $R^1$ is ($C_2$-$C_6$)alkenyl, can be reacted with osmium tetroxide and N-methylmorpholine-N-oxide to afford a compound of Formula I wherein $R^1$ is vicinal dihydroxy($C_2$-$C_6$)alkyl,

(10) a compound of Formula I, wherein $R^3$ is ($C_2$-$C_6$) alkenyl, can be reacted with osmium tetroxide and N-methylmorpholine-N-oxide to afford a vicinal diol compound of Formula I wherein $R^3$ is vicinal dihydroxy($C_2$-$C_6$)alkyl,

(11) a compound of Formula I, wherein $R^1$ is ($C_2$-$C_6$) alkenyl, can be reacted with ozone followed by $NaBH_4$ to give a compound of Formula I wherein $R^1$ is ω-hydroxy($C_1$-$C_6$) alkyl.

(12) a compound of Formula I, wherein $R^3$ is ($C_2$-$C_6$) alkenyl, can be reacted with ozone followed by $NaBH_4$ to give a compound of Formula I wherein $R^3$ is ω-hydroxy($C_1$-$C_5$) alkyl.

(13) a compound of Formula I wherein $R^1$ or $R^3$ is amino ($C_1$-$C_6$)alkyl can be reacted with an ($C_1$-$C_6$)alkyl isocyanate to give a compound of Formula I wherein $R^1$ or $R^3$ is ($C_1$-$C_6$) alkylaminocarbonylamino($C_1$-$C_6$)alkyl.

(14) a compound of Formula I wherein $R^1$ or $R^3$ is amino ($C_1$-$C_6$)alkyl can be reacted with an ($C_1$-$C_6$)alkyl chloroformate to give a compound of Formula I wherein $R^1$ or $R^3$ is ($C_1$-$C_6$)alkoxycarbonylamino($C_1$-$C_6$)alkyl.

(15) a compound of Formula I wherein $R^1$ or $R^3$ is amino ($C_1$-$C_6$)alkyl can be reacted with chlorosulfonyl isocyanate or sulfamide to give a compound of Formula I wherein $R^1$ or $R^3$ is aminosulfonylamino($C_1$-$C_6$)alkyl.

(16) a compound of Formula I wherein $R^1$ or $R^3$ is amino ($C_1$-$C_6$)alkyl can be reacted with a ($C_1$-$C_6$)alkylsulfamoyl chloride to give a compound of Formula I wherein $R^1$ or $R^3$ is ($C_1$-$C_6$)alkylaminosulfonylamino($C_1$-$C_6$)alkyl.

(17) a compound of Formula I wherein $R^1$ or $R^3$ is hydroxy ($C_1$-$C_6$)alkyl can be reacted with chlorosulfonyl isocyanate to give a compound of Formula I wherein $R^1$ or $R^3$ is aminosulfonyloxy($C_1$-$C_6$)alkyl.

(18) a compound of Formula I wherein $R^1$ or $R^3$ is hydroxy ($C_1$-$C_6$)alkyl can be reacted with p-nitrophenyl chloroformate, pentafluorophenyl chloroformate or carbonyl diimidazole, followed by ammonia, a ($C_1$-$C_6$)alkylamine or a di($C_1$-$C_6$)alkylamine to give a compound of Formula I wherein $R^1$ or $R^3$ is aminocarboxy($C_1$-$C_6$)alkyl, ($C_1$-$C_6$)alkyl aminocarboxy($C_1$-$C_6$)alkyl or di($C_1$-$C_6$)alkyl aminocarboxy($C_1$-$C_6$) alkyl.

(19) a compound of Formula I wherein $R^1$ or $R^3$ is hydroxy ($C_1$-$C_6$)alkyl can be reacted with $POCl_3$ to give a compound of Formula I wherein $R^1$ or $R^3$ is $(HO)_2P(=O)O(C_1$-$C_6)$ alkyl.

(20) a compound of Formula I wherein $Cy^1$ is substituted with bromine or iodine, $A^2$ is a bond and $Cy^2$ is hydrogen can be reacted with a cyclic amine in the presence of a palladium catalyst to give a compound of Formula I wherein $A^2$ is a bond and $Cy^2$ is a cyclic amino moiety attached through its nitrogen atom.

(21) a compound of Formula I wherein $R^5$ is H can be reacted with an ($C_1$-$C_6$)alkyl halide in the presence of a strong base such as sodium hydride to afford a compound of Formula I wherein $R^5$ is ($C_1$-$C_6$)alkyl.

(22) a compound of Formula I wherein $R^1$ or $R^3$ is ω-$H_2$NCO($C_1$-$C_6$)alkyl can be reacted with TFAA in the presence of pyridine to afford a compound of Formula I wherein $R^1$ or $R^3$ is ω-cyano($C_1$-$C_6$)alkyl.

Purification Methods

Compounds of the invention can be purified by high pressure liquid chromatography (prep HPLC). Unless otherwise specified, prep HPLC refers to preparative reverse phase HPLC on a C-18 column eluted with a water/acetonitrile gradient containing 0.01% TFA run on a Gilson 215 system.

LC-MS Methods

Method 1 (30-90)

| Column | YMC-PACK ODS-AQ, 50 × 2.0 mm 5 μm | | |
|---|---|---|---|
| Mobile Phase | A: water (4 L) + TFA (1.5 mL)) | | |
| | B: acetonitrile (4 L) + TFA (0.75 mL)) | | |
| | TIME (min) | A % | B % |
| | 0 | 70 | 30 |
| | 2.2 | 10 | 90 |
| | 2.5 | 10 | 90 |
| Flow Rate | 1 mL/min | | |
| Wavelength | UV220 | | |
| Oven Temp | 50° C. | | |
| MS ionization | ESI | | |

Example 1

(R)-4-methyl-4-phenyl-1-m-tolyltetrahydropyrimidin-2(1H)-one

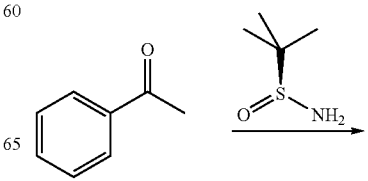

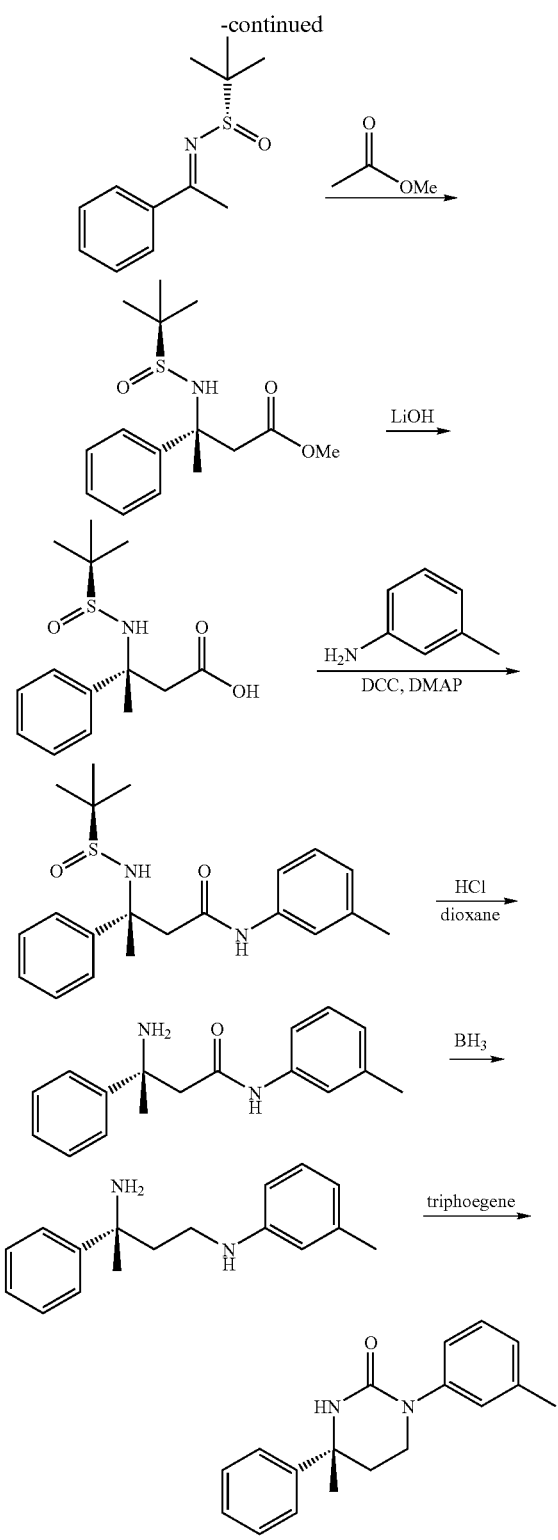

Step 1. (S)-2-methyl-N-(1-phenylethylidene)propane-2-sulfinamide

A solution of Ti(OEt)₄ (8.7 g, 36.4 mmol) and acetophenone (2.2 g, 18.2 mmol) in THF (18 mL) was prepared under a N₂ atmosphere. A solution of 2-methyl-propane-2-sulfinic acid amide (2.0 g, 1.5 mmol) in THF (18 mL) was added and the mixture was heated to 75° C. overnight. The mixture was cooled to rt and poured into an equal volume of brine with rapid stirring. The resulting suspension was filtered and filter cake was washed with ethyl acetate. The filtrate was extracted with ethyl acetate. The combined organic layers were washed with brine, dried over Na₂SO₄, and concentrated. The crude product was purified by silica gel chromatography to (S)-2-methyl-N-(1-phenylethylidene)propane-2-sulfinamide (2.70 g, 73%). ¹H NMR (CDCl₃): 1.25 (s, 9H), 2.7 (s, 3H), 7.32-7.40 (m, 2H), 7.40-7.46 (m, 1H), 7.80-7.82 (m, 2H).

Step 2. (R)-methyl 3-((S)-1,1-dimethylethylsulfinamido)-3-phenylbutanoate

A solution of i-Pr₂NH in THF (25 mL) was cooled to −78° C., n-BuLi (2.5M, 2 mL) was added and the solution was stirred for 1 h. Then methyl acetate (4.48 mmol, 278 mg) was added and the mixture was stirred for 30 min. To this solution Ti(Oi-Pr)₃Cl (1 M, 9.4 mL) was added. After 0.5 h, (S)-2-methyl-N-(1-phenylethylidene)propane-2-sulfinamide (500 mg, 2.24 mmol) dissolved in THF (1 mL) was added. The mixture was stirred at −78° C. for 3 h. The reaction was quenched with NH₄Cl and warmed to rt. The mixture was diluted with water and filtered. The solid was washed with H₂O/EtOAc and filtered. The combined organic layers were washed with brine, dried over Na₂SO₄, and concentrated. The residue was purified by preparative TLC to afford (R)-methyl 3-((S)-1,1-dimethylethylsulfinamido)-3-phenylbutanoate (305 mg, 46%). ¹H NMR (CDCl₃): 1.24 (s, 9H), 1.68 (s, 3H), 3.08 (s, 2H), 3.53 (s, 3H), 5.46 (s, 1H), 7.15-7.18 (m, 1H), 7.23-7.30 (m, 2H), 7.30-7.36 (m, 2H).

Step 3. (R)-3-((S)-1,1-dimethylethylsulfinamido)-3-phenylbutanoic acid

To a solution of (R)-methyl 3-((S)-1,1-dimethylethylsulfinamido)-3-phenylbutanoate (280 mg, 0.94 mmol) in MeOH (2 mL) and H₂O (0.5 mL) was added LiOH (138 mg, 3.29 mmol). The solution was stirred for 4 h and then concentrated to give the residue. The residue was dissolved in 15% MeOH/H₂O and filtered to give (R)-3-((S)-1,1-dimethylethylsulfinamido)-3-phenylbutanoic acid (266 mg, 100%). ¹H NMR (CDCl₃): 1.10 (s, 9H), 1.51 (s, 3H), 2.43-2.52 (d, 1H), 2.73-2.86 (d, 1H), 7.15-7.18 (m, 1H), 7.06-7.12 (m, 3H), 7.30-7.40 (m, 2H).

Step 4. (R)-3-((S)-1,1-dimethylethylsulfinamido)-3-phenyl-N-m-tolylbutanamide

To a solution of (R)-3-((S)-1,1-dimethylethylsulfinamido)-3-phenylbutanoic acid (266 mg, 0.94 mmol) in CH₂Cl₂ (5 mL) was added m-tolylamine (111 mg, 1.03 mmol), DCC (212 mg, 1.03 mmol) and DMAP (11.5 mg, 0.094 mmol) at 0° C. Then the reaction mixture was stirred at room temperature overnight. The residue was purified by preparative TLC to give (R)-3-((S)-1,1-dimethylethylsulfinamido)-3-phenyl-N-m-tolylbutanamide (25 mg, 7%). ¹H NMR (CDCl₃): 1.10-1.20 (m, 12H), 1.51-1.65 (m, 11H), 3.10-3.30 (m, 2H), 4.25 (s, 1H), 6.80-6.90 (m, 1H), 7.06-7.15 (m, 1H), 7.28-7.48 (m, 5H), 7.50-7.60 (m, 2H), 8.95 (s, 1H).

Step 5. (R)-3-amino-3-phenyl-N-m-tolylbutanamide

To a solution of (R)-3-((S)-1,1-dimethylethylsulfinamido)-3-phenyl-N-m-tolylbutanamide (300 mg, 0.81 mmol) in MeOH (5 mL) was added 4M HCl/dioxane (3 mL, 12 mmol). The solution was stirred for 1 h and concentrated to give (R)-3-amino-3-phenyl-N-m-tolylbutanamide (218 mg, 90%) without purification.

Step 6. (R)-3-phenyl-$N^1$-m-tolylbutane-1,3-diamine

A solution of (R)-3-amino-3-phenyl-N-m-tolylbutanamide (218 mg, 0.81 mmol) in THF (5 mL) was cooled to 0° C. under $N_2$ and 2M $BH_3.Me_2S$ (1 mL, 2 mmol) was added. Then the mixture was stirred at 80° C. overnight. The reaction mixture was quenched with MeOH and concentrated. The residue was purified by preparative TLC to afford (R)-3-phenyl-$N^1$-m-tolylbutane-1,3-diamine (50 mg, 24%). $^1$H NMR ($CDCl_3$): 1.59-1.62 (m, 7H), 1.30-1.35 (m, 4H), 2.15-2.20 (m, 3H), 2.40-2.65 (m, 2H), 2.98-3.05 (m, 2H), 3.35-3.45 (m, 1H), 3.60-3.65 (m, 6H), 3.75-3.80 (m, 1H), 6.40-6.60 (m, 2H), 6.90-7.01 (m, 1H), 7.25-7.40 (m, 4H), 7.45-7.52 (m, 2H).

Step 7

To a solution of (R)-3-phenyl-$N^1$-m-tolylbutane-1,3-diamine (50 mg, 0.2 mol) and $Et_3N$ (60 mg, 0.6 mmol) in $CH_2Cl_2$ (3 mL) was added triphosgene (24 mg, 0.08 mmol) at 0° C. The reaction mixture was stirred at 0° C. for 2 h and concentrated. The residue was purified by preparative HPLC to give 4-methyl-4-phenyl-1-m-tolyl-tetrahydro-pyrimidin-2-one (8 mg, 14%). LC-MS Method 1 $t_R$=1.13 min, m/z=281; $^1$H NMR ($CDCl_3$): 1.65 (s, 3H), 2.15-2.23 (m, 1H), 2.25 (s, 3H), 2.27-2.47 (m, 1H), 3.20-3.22 (t, 1H), 3.37-3.40 (d, 1H), 6.89-6.92 (m, 2H), 6.99-7.01 (m, 1H), 7.15-7.17 (m, 1H), 7.25-7.27 (m, 1H), 7.7.31-7.38 (m, 4H), 7.83 (s, 1H).

Example 2

4-allyl-1-((1S)-1-(4-bromophenyl)ethyl)-4-(4-fluorophenyl)tetrahydropyrimidin-2(1H)-one Isomer 1

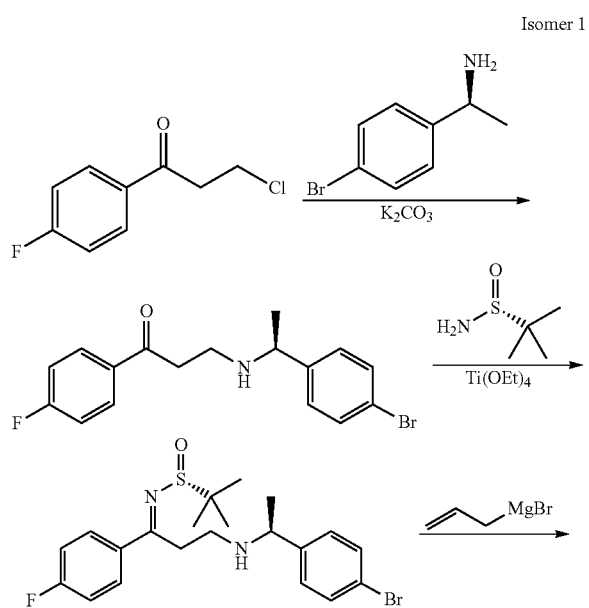

-continued

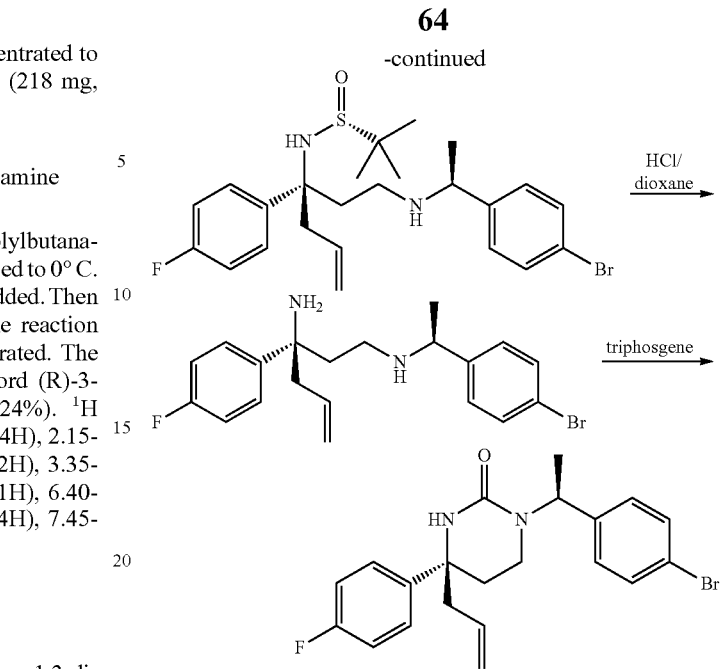

Step 1
To a solution of (S)-1-(4-bromophenyl)ethanamine (20 g, 0.1 mol) and $K_2CO_3$ (28 g, 0.2 mol) in MeCN (200 mL) was added a solution of 3-chloro-1-(4-fluorophenyl)propan-1-one (18.6 g, 0.1 mol) in MeCN (20 mL). The mixture was stirred overnight. The solid was filtered, and the filtrate was concentrated to give (S)-3-(1-(4-bromophenyl)ethylamino)-1-(4-fluorophenyl)propan-1-one (30 g, 86%), which was used for the next step without purification. $^1$H NMR ($CDCl_3$): δ=1.29 (m, 3H), 2.56-2.91 (m, 2H), 3.11 (m, 2H), 3.68 (q, 1H), 7.11 (m, 2H), 7.21 (m, 2H), 7.43 (m, 2H), 7.99 (m, 2H).
Step 2
A mixture of (S)-3-(1-(4-bromophenyl)ethylamino)-1-(4-fluorophenyl)propan-1-one (14.5 g, 0.04 mol), (R)-2-methylpropane-2-sulfinamide (5.5 g, 0.046 mol), and Ti(OEt)$_4$ (18 g, 0.08 mmol) in THF (150 mL) was heated to reflux overnight. The mixture was treated with brine, and the precipitate was filtered. The filtrate was concentrated to give (R)—N-(3-((1S)-1-(4-bromophenyl)ethylamino)-1-(4-fluorophenyl) propylidene)-2-methylpropane-2-sulfinamide (13.3 g, 59%), which was used for the next step without purification.
Step 3
To a solution of (R)—N-(3-((1S)-1-(4-bromophenyl)ethylamino)-1-(4-fluorophenyl) propylidene)-2-methylpropane-2-sulfinamide (13.3 g, 29.3 mmol) in THF (300 mL) was added 1M allylmagnesium bromide (88 mL, 0.088 mol) under nitrogen at −78° C. The mixture was stirred for 2 h. The reaction was quenched with satd aq $NH_4Cl$. The organic phase was separated and concentrated to give crude (R)—N—((R)-1-((S)-1-(4-bromophenyl)ethylamino)-3-(4-fluorophenyl)hex-5-en-3-yl)-2-methylpropane-2-sulfinamide (14 g, 100%), which was used for the next step without further purification.
Step 4
A mixture of (R)—N—((R)-1-((S)-1-(4-bromophenyl)ethylamino)-3-(4-fluorophenyl)hex-5-en-3-yl)-2-methylpropane-2-sulfinamide (16 g, 32.2 mmol) in 4M HCl in dioxane (100 mL, 400 mmol) was stirred for 1 h at 0° C. The mixture was concentrated to give the residue, which was treated with saturated $Na_2CO_3$ solution. The resulting mixture was extracted with EtOAc, and the combined organic layers was concentrated to afford (R)—N¹—((S)-1-(4-bromophenyl)ethyl)-3-(4-fluorophenyl)hex-5-ene-1,3-diamine (12 g, 100%), which was used for the next step without purification.

Step 5

To a solution of (R)—N¹—((S)-1-(4-bromophenyl)ethyl)-3-(4-fluorophenyl)hex-5-ene-1,3-diamine (12 g, 31 mmol) in CH₂Cl₂ (100 mL) and Et₃N (36 g, 0.36 mmol) was added triphosgene (3.50 g, 11.8 mmol) at 0° C. The resulting mixture was stirred for 3 h. The mixture was washed with water. The organic layer was separated, and concentrated to give the crude product, which was purified by column chromatography to afford (R)-4-allyl-1-((S)-1-(4-bromophenyl)ethyl)-4-(4-fluorophenyl)tetrahydropyrimidin-2(1H)-one (1.0 g, 8%). $^1$H NMR (CDCl₃): δ=1.49 (t, 3H), 2.00 (m, 2H), 2.35 (m, 2H), 2.76 (m, 2H), 5.18 (m, 2H), 5.31 (m, 2H), 5.72 (q, 1H), 6.95 (m, 4H), 7.18 (m, 2H), 7.254 (m, 2H).

Isomer 2

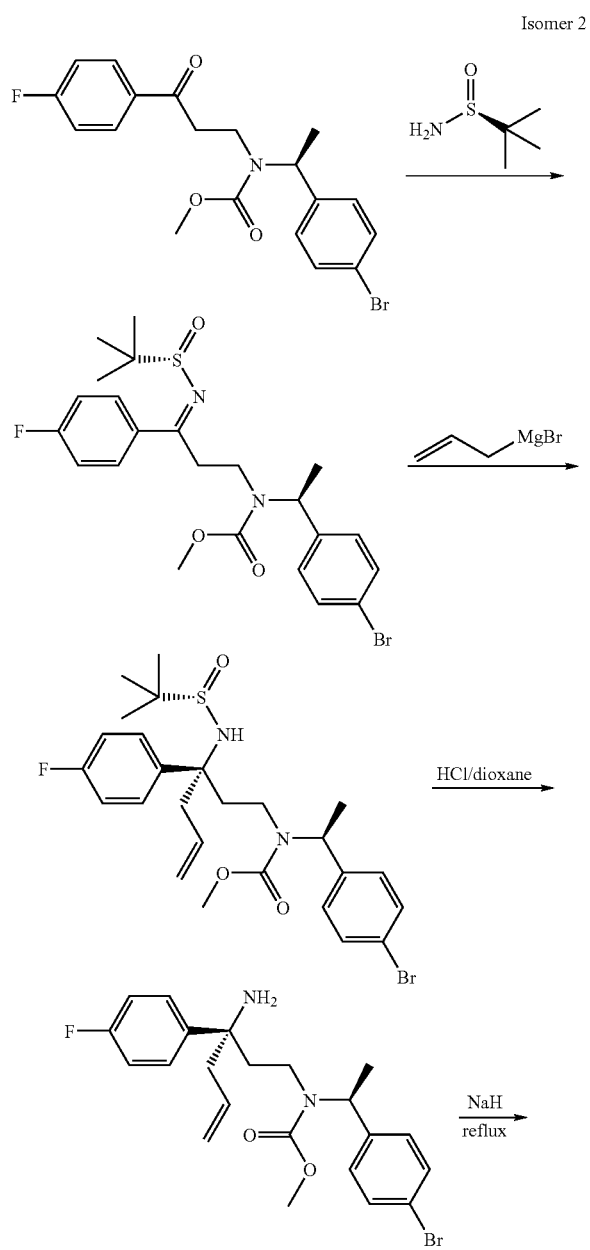

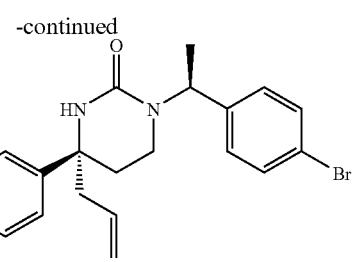

Step 1

To a solution of (S)-methyl 1-(4-bromophenyl)ethyl(3-(4-fluorophenyl)-3-oxopropyl)carbamate (982 mg, 2 mmol) and (S)-2-methylpropane-2-sulfinamide (265 mg, 2 mmol) in anhydrous THF (20 mL) at rt was added Ti(OEt)₄ (1 g, 4 mmol). The reaction mixture was heated at 70° C. for 24 h. After cooling to rt, the reaction mixture was poured into brine with vigorous stirring. The resulting suspension was filtered through a pad of celite and the solid was washed with brine. The combined organic phases were dried, filtered and concentrated to give methyl (1S)-1-(4-bromophenyl)ethyl((Z)-3-((S)-tert-butylsulfinylimino)-3-(4-fluorophenyl)propyl)carbamate (794 mg, 65%). $^1$H NMR (CD₃OD): 1.24 (m, 9H), 1.58 (d, 4H), 1.61 (m, 1H), 2.95 (m, 1H), 3.48 (m, 2H), 3.66 (m, 1H), 3.80 (m, 3H), 4.58 (m, 1H), 3.78 (m, 3H), 5.36 (m, 1H), 7.18 (m, 3H), 7.30 (m, 2H), 7.50 (m, 2H), 7.96 (m, 2H).

Step 2

To a solution of methyl (1S)-1-(4-bromophenyl)ethyl(3-((S)-tert-butylsulfinylimino)-3-(4-fluorophenyl)propyl)carbamate (200 mg, 0.4 mmol) in anhydrous THF (5 mL) was added 1M allylmagnesium bromide (1.2 mL, 1.2 mmol) at −78° C. The reaction mixture was stirred at −78° C. for 4 h and allowed to warm to rt. After stirring for 2 h at rt, the reaction mixture was quenched with satd aq NH₄Cl and extracted with EtOAc (2×). The combined organic phases were dried, filtered and concentrated to give a residue, which was purified by TLC to provide methyl (S)-1-(4-bromophenyl)ethyl((S)-3-((S)-1,1-dimethylethylsulfinamido)-3-(4-fluorophenyl)hex-5-enyl)carbamate (96 mg, 45%). $^1$H NMR (CD₃OD): 1.28 (m, 9H), 1.48 (m, 3H), 2.10 (m, 1H), 2.30 (m, 1H), 2.72 (m, 4H), 3.66 (m, 3H), 5.08 (m, 2H), 5.40 (m, 2H), 7.10 (m, 4H), 7.32 (m, 2H), 7.50 (m, 2H).

Step 3

A 50-mL round-bottomed flask was charged with methyl (S)-1-(4-bromophenyl)ethyl((S)-3-((S)-1,1-dimethylethylsulfinamido)-3-(4-fluorophenyl)hex-5-enyl)carbamate (96 mg, 0.17 mmol) and 4 M HCl in dioxane (10 mL, 40 mmol) while cooling in an ice-water bath. The reaction mixture was concentrated to give crude methyl (S)-3-amino-3-(4-fluorophenyl)hex-5-enyl((S)-1-(4-bromophenyl)ethyl)carbamate, which was used to the next step without purification.

Step 4

To a mixture of NaH (100 mg, 4 mmol) and anhydrous THF (8 mL) was added dropwise a solution of crude methyl (S)-3-amino-3-(4-fluorophenyl)hex-5-enyl((S)-1-(4-bromophenyl)ethyl)carbamate (39 mg, 0.1 mmol) in anhydrous THF (8 mL) at 0° C. The reaction mixture was refluxed overnight. The reaction mixture was quenched with methanol in an ice bath and evaporated to leave a residue, which was dissolved in CH₂Cl₂. The combined organic phase was dried, filtered and concentrated to give the crude product, which was purified by TLC to provide (S)-4-allyl-1-((S)-1-(4-bromophenyl)ethyl)-4-(4-fluorophenyptetrahydropyrimidin-2(1H)-one (1.2 mg, 3%). LC-MS Method 1 $t_R$=1.603 min, m/z=419; $^1$H NMR (CD₃OD) 1.36 (d, 3H), 1.81-1.92 (m, 1H), 2.16-2.22 (m, 1H), 2.46-2.53 (m, 1H), 2.61-2.84 (m, 3H), 5.12-5.19 (m, 1H), 5.56-5.69 (m, 1H), 7.06-7.13 (m, 2H), 7.18-7.24 (m, 2H), 7.22-7.29 (m, 2H), 7.42-7.51 (m, 2H).

Example 3

(R)-4-allyl-1-((S)-1-(4-bromophenyl)ethyl)-4-(4-fluorophenyl)tetrahydropyrimidin-2(1H)-one

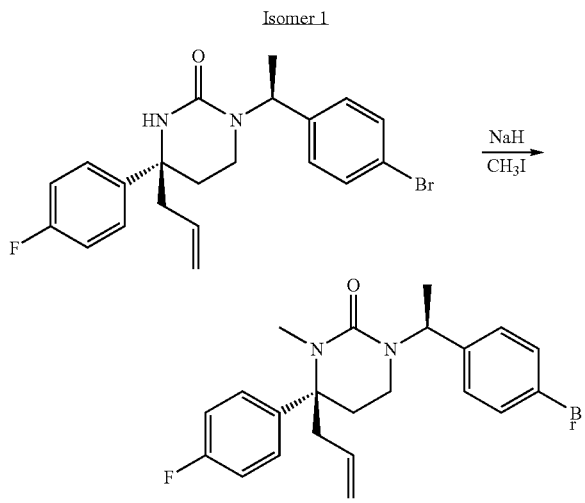

To a suspension of NaH (84 mg, 2.1 mmol) in THF (1 mL) was added a solution of (R)-4-allyl-1-((S)-1-(4-bromophenyl)ethyl)-4-(4-fluorophenyl)tetrahydropyrimidin-2(1H)-one (50 mg, 0.120 mmol) in THF (5 mL) at 0° C. The resulting mixture was stirred for 2 h. Then CH₃I (50 mg, 0.35 mmol) was added. The mixture was stirred for 3 h. The reaction was quenched with satd aq NH₄Cl. The organic phase was separated, and concentrated to give the crude product, which was purified by preparative TLC to afford (R)-4-allyl-1-((S)-1-(4-bromophenyl)ethyl)-4-(4-fluorophenyl)-3-methyltetrahydropyrimidin-2(1H)-one (11.7 mg, 23%). LC-MS Method 1 $t_R$=1.403 min, m/z=431; ¹H NMR (CDCl₃): δ=1.38 (d, 3H), 1.63 (m, 1H), 2.19 (m, 2H), 2.70 (m, 2H), 2.83 (m, 3H), 5.20 (m, 2H), 5.71-5.84 (m, 2H), 6.91 (m, 2H), 7.05 (m, 4H), 7.32 (m, 2H).

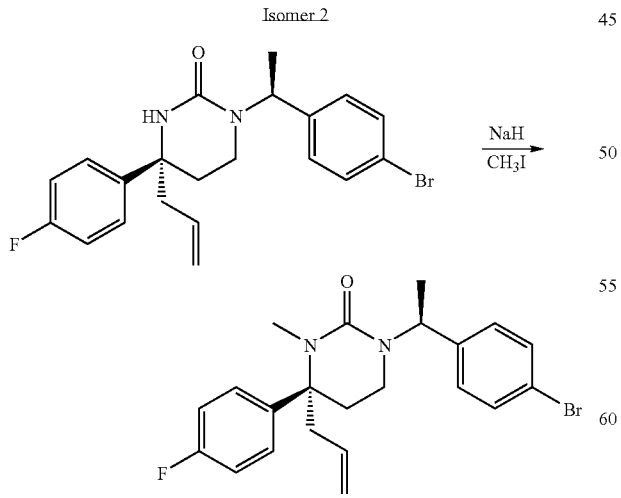

(S)-4-allyl-1-((S)-1-(4-bromophenyl)ethyl)-4-(4-fluorophenyl)-3-methyltetrahydropyrimidin-2(1H)-one was prepared from (S)-4-allyl-1-((S)-1-(4-bromophenyl)ethyl)-4-(4-fluorophenyl)tetrahydropyrimidin-2(1H)-one using a procedure analogous to that described immediately above. LC-MS Method 1 $t_R$=1.755 min, m/z=433.1; ¹H NMR (CDCl₃) 1.42 (d, 3H), 1.61 (m, 1H), 1.64 (m, 1H), 2.12 (m, 1H), 2.53 (m, 1H), 2.68 (m, 1H), 2.77 (m, 2H), 2.93 (s, 3H), 5.27 (m, 2H), 5.81 (m, 1H), 5.88 (m, 1H), 7.04 (m, 2H), 7.18 (m, 4H), 7.44 (m, 2H).

Example 4

4-allyl-1-((1S)-1-(2',4'-difluorobiphenyl-4-yl)ethyl)-4-(4-fluorophenyl)tetrahydropyrimidin-2(1H)-one

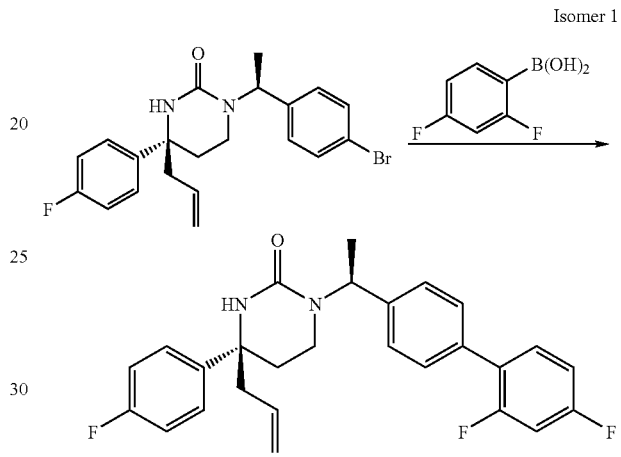

A mixture of (R)-4-allyl-1-((S)-1-(4-bromophenyl)ethyl)-4-(4-fluorophenyl)tetrahydropyrimidin-2(1H)-one (188 mg, 0.452 mmol), 2,4-difluorophenylboronic acid (86 mg, 0.581 mmol), Pd(Ph₃P)₂Cl₂ (20 mg) and aqueous Cs₂CO₃ solution (0.5 mL, 2 M) in 1,4-dioxane (10 mL) was stirred and heated at reflux for 2 h. The organic phase was separated, and concentrated to give the crude product, which was purified by preparative TLC to give (R)-4-allyl-1-((S)-1-(2',4'-difluorobiphenyl-4-yl)ethyl)-4-(4-fluorophenyl)tetrahydropyrimidin-2(1H)-one (120 mg, 59%).

(S)-4-allyl-1-((S)-1-(2',4'-difluorobiphenyl-4-yl)ethyl)-4-(4-fluorophenyl)tetrahydropyrimidin-2(1H)-one was prepared following a procedure analogous to that described immediately above using (S)-4-allyl-H(S)-1-(4-bromophenyl)ethyl)-4-(4-fluorophenyl)tetrahydropyrimidin-2(1H)-one.

Example 5

4-allyl-1-((1S)-1-(4'-fluorobiphenyl-4-yl)ethyl)-4-(4-fluorophenyl)tetrahydropyrimidin-2(1H)-one Isomer 1

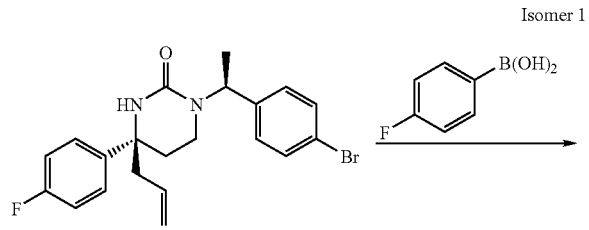

(R)-4-allyl-1-((S)-1-(4'-fluorobiphenyl-4-yl)ethyl)-4-(4-fluorophenyl)tetrahydropyrimidin-2(1H)-one was prepared following a procedure analogous to that described in Example 4 using 4-fluorophenylboronic acid and (R)-4-allyl-1-((3)-1-(4-bromophenyl)ethyl)-4-(4-fluorophenyl)tetrahydropyrimidin-2(1H)-one.

Isomer 2

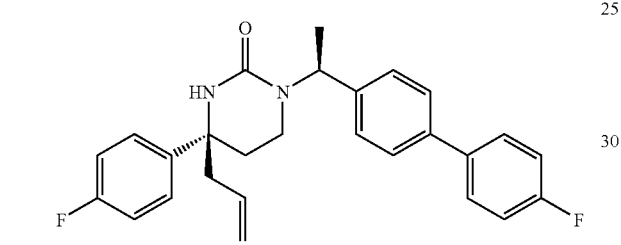

(S)-4-allyl-1-((S)-1-(4'-fluorobiphenyl-4-yl)ethyl)-4-(4-fluorophenyl)tetrahydropyrimidin-2(1H)-one was prepared following a procedure analogous to that described in Example 4 using 4-fluorophenylboronic acid and (S)-4-allyl-1-((S)-1-(4-bromophenyl)ethyl)-4-(4-fluorophenyl)tetrahydropyrimidin-2(1H)-one.

Example 6

1-((1S)-1-(2',4'-difluorobiphenyl-4-yl)ethyl)-4-(4-fluorophenyl)-4-(2-hydroxyethyl)tetrahydropyrimidin-2(1H)-one

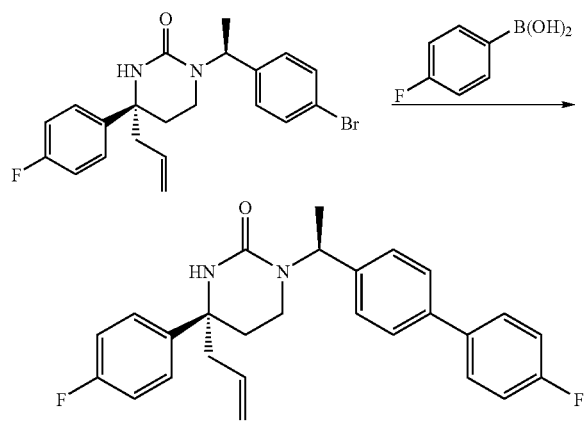

A solution of (R)-4-allyl-1-((S)-1-(2',4'-difluorobiphenyl-4-yl)ethyl)-4-(4-fluorophenyl)tetrahydropyrimidin-2(1H)-one (60 mg, 0.136 mmol) in CH$_2$Cl$_2$ (20 mL) was cooled to −78° C. and ozone was bubbled in until a blue color appeared. NaBH$_4$ (200 mg, 5.26 mmol) was added to the above solution, and the mixture was stirred overnight. The reaction was quenched with water. The organic phase was separated, and concentrated to give the crude product which was purified by prep HPLC to afford (S)-1-((S)-1-(2',4'-difluorobiphenyl-4-yl)ethyl)-4-(4-fluorophenyl)-4-(2-hydroxyethyl)tetrahydropyrimidin-2(1H)-one (16 mg, 27%). LC-MS Method 1 $t_R$=1.422 min, m/z=455.1; $^1$H NMR: (400 MHz, CDCl$_3$): δ=1.50 (d, 3H), 1.91-2.20 (m, 5H), 2.31 (m, 1H), 2.86 (m, 1H), 3.40 (m, 2H), 3.66 (m, 1H), 5.74 (m, 1H), 6.82 (m, 2H), 6.94 (m, 2H), 7.11 (m, 2H), 7.18-7.32 (m, 4H), 7.38 (m, 1H).

Isomer 2

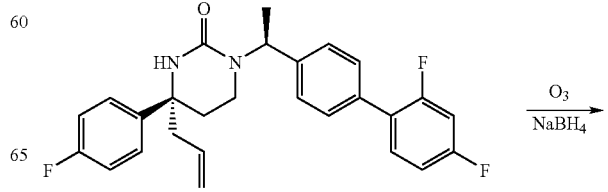

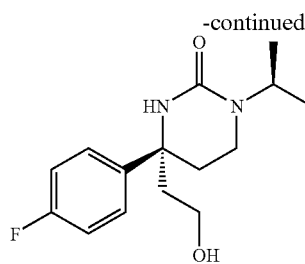

(R)-1-((S)-1-(2',4'-difluorobiphenyl-4-yl)ethyl)-4-(4-fluorophenyl)-4-(2-hydroxyethyl)tetrahydropyrimidin-2(1H)-one was prepared following a procedure analogous to that described immediately above starting with (S)-4-allyl-1-((S)-1-(2',4'-difluorobiphenyl-4-yl)ethyl)-4-(4-fluorophenyl)tetrahydropyrimidin-2(1H)-one. LC-MS Method 1 $t_R$=1.496 min, m/z=455.2; $^1$H NMR (CDCl$_3$) 1.37 (d, 3H), 1.81-1.93 (m, 3H), 1.99 (m, 2H), 2.17 (m, 1H), 2.52 (m, 1H), 2.64 (m, 1H), 3.33 (m, 1H), 3.71 (m, 1H), 5.82 (m, 1H), 6.83 (m, 3H), 7.02 (m, 2H), 7.27 (m, 4H), 7.49 (m, 2H).

Example 7

1-((1S)-1-(2',4'-difluorobiphenyl-4-yl)ethyl)-4-(4-fluorophenyl)-4-(3-hydroxypropyl)tetrahydropyrimidin-2(1H)-one Isomer 1

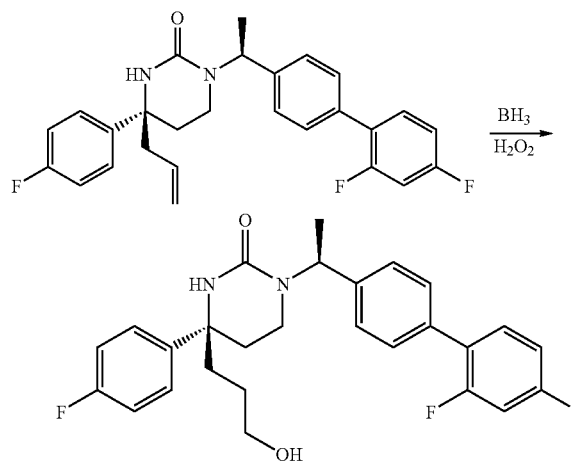

To a solution of (R)-4-allyl-1-((S)-1-(2',4'-difluorobiphenyl-4-yl)ethyl)-4-(4-fluorophenyl)tetrahydropyrimidin-2(1H)-one (42 mg, 0.092 mmol) in THF (10 mL) was added 1M BH$_3$ in THF (1.5 mL, 1.5 mmol) at 0° C. under nitrogen. The mixture was stirred for 2 h. The reaction was quenched by water. 3 M aq NaOH (0.3 mL, 3 mmol) and H$_2$O$_2$ (3 mL) were added. The resulting mixture was stirred for 1.5 h. The mixture was extracted with EtOAc and the combined organic phase was concentrated to give the crude product, which was purified by preparative HPLC to give (R)-1-((S)-1-(2',4'-difluorobiphenyl-4-yl)ethyl)-4-(4-fluorophenyl)-4-(3-hydroxypropyl)tetrahydropyrimidin-2(1H)-one (8 mg, 19%). LC-MS Method 1 $t_R$=1.413 min, m/z=469.2; $^1$H NMR (CDCl$_3$): δ=1.36 (m, 2H), 1.45 (m, 3H), 1.91-2.01 (m, 5H), 2.18 (m, 1H), 2.83 (m, 1H), 3.52 (m, 2H), 5.76 (m, 2H), 6.09 (m, 1H), 6.38-6.98 (m, 4H), 7.16 (m, 2H), 7.22 (m, 1H), 7.25 (m, 1H), 7.28 (m, 3H).

Isomer 2

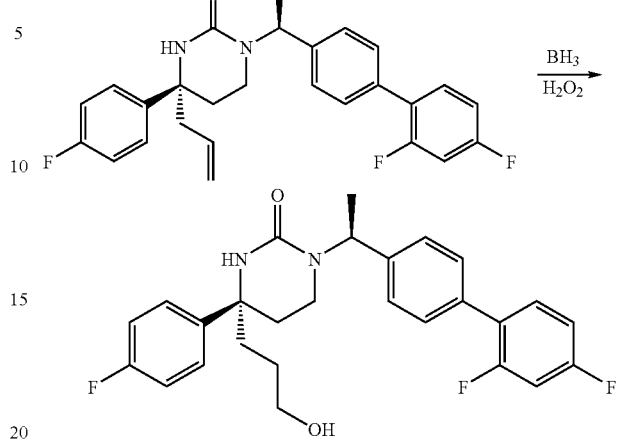

(S)-1-((S)-1-(2',4'-difluorobiphenyl-4-yl)ethyl)-4-(4-fluorophenyl)-4-(3-hydroxypropyl)tetrahydropyrimidin-2(1H)-one was prepared following a procedure analogous to that described immediately above starting with (S)-4-allyl-1-((S)-1-(2',4'-difluorobiphenyl-4-yl)ethyl)-4-(4-fluorophenyl)tetrahydropyrimidin-2(1H)-one. LC-MS Method 1 $t_R$=1.249 min, m/z=469.1; $^1$H NMR (CDCl$_3$) 1.38 (d, 3H), 1.42-1.58 (m, 1H), 1.88-2.09 (m, 4H), 2.53-2.78 (m, 2H), 3.57-3.62 (m, 2H), 5.72-5.97 (m, 1H), 6.88-6.99 (m, 2H), 7.17 (m, 2H), 7.22 (m, 2H), 7.37 (m, 2H), 7.47 (m, 2H).

Example 8

(4S)-1-((S)-1-(2',4'-difluorobiphenyl-4-yl)ethyl)-4-(2,3-dihydroxypropyl)-4-(4-fluorophenyl)tetrahydropyrimidin-2(1H)-one

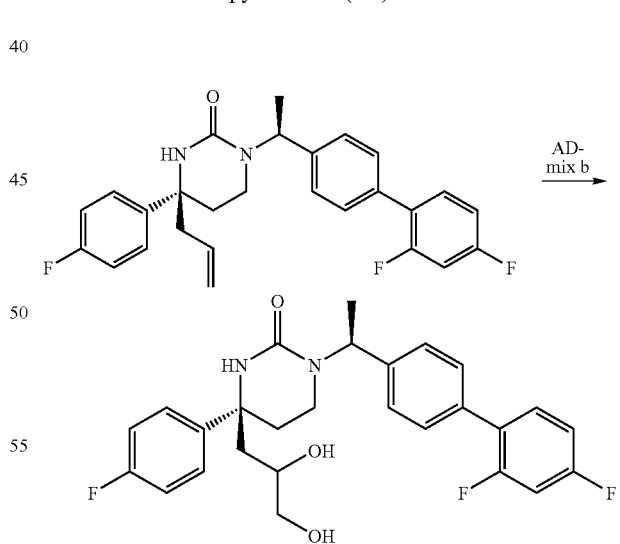

To a solution of (R)-4-allyl-1-((S)-1-(2',4'-difluorobiphenyl-4-yl)ethyl)-4-(4-fluorophenyl)tetrahydropyrimidin-2(1H)-one (74 mg, 0.164 mmol) in 2-methylpropan-2-ol (3 mL) was added a solution of AD-mix-β (300 mg) in water (3 mL). The formed mixture was stirred for 48 h. The mixture was treated with aqueous Na$_2$SO$_3$ solution, and extracted with EtOAc. The organic phase was separated, and concentrated to give the crude product, which was purified by preparative HPLC to give two isomers:

(4S)-1-((S)-1-(2',4'-difluorobiphenyl-4-yl)ethyl)-4-(2,3-dihydroxypropyl)-4-(4-fluorophenyl)tetrahydropyrimidin-2(1H)-one isomer 1 (13.6 mg, 34%). LC-MS Method 1 $t_R$=1.33 min, m/z=485.2; $^1$H NMR (CDCl$_3$) 1.42 (d, 3H), 1.88-2.13 (m, 7H), 2.78 (m, 1H), 3.42 (m, 3H), 5.22 (s, 1H), 5.68 (m, 1H), 6.84 (m, 2H), 6.93 (m, 2H), 7.06 (m, 2H), 7.19 (m, 1H), 7.23 (m, 3H), 7.43 (s, 1H).

(4S)-1-((S)-1-(2',4'-difluorobiphenyl-4-yl)ethyl)-4-(2,3-dihydroxypropyl)-4-(4-fluorophenyl)tetrahydropyrimidin-2(1H)-one isomer 2 (11.9 mg, 30%). LC-MS Method 1 $t_R$=1.297 min, m/z=485.2; $^1$H NMR (CDCl$_3$): δ=1.53 (d, 3H), 2.02-2.11 (m, 4H), 2.22 (m, 3H), 2.90 (m, 1H), 3.49 (m, 2H), 3.95 (m, 1H), 5.78 (m, 1H), 6.82 (m, 1H), 6.96 (m, 4H), 7.16 (m, 2H), 7.28 (m, 1H), 7.30 (m, 2H), 7.32 (m, 1H).

Example 9

4-(2,3-dihydroxypropyl)-1-((1S)-1-(4'-fluorobiphenyl-4-yl)ethyl)-4-(4-fluorophenyl)tetrahydropyrimidin-2(1H)-one

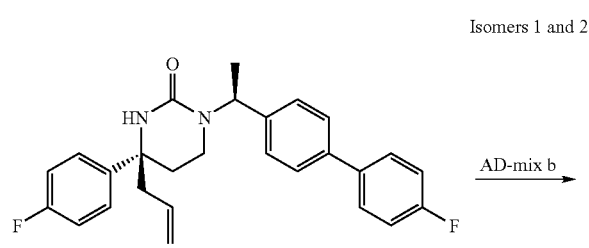

Treatment of (R)-4-allyl-1-((S)-1-(4'-fluorobiphenyl-4-yl)ethyl)-4-(4-fluorophenyl)tetrahydropyrimidin-2(1H)-one with AD-mix β following a procedure analogous to that described in Example 8 afforded (4S)-4-(2,3-dihydroxypropyl)-1-((S)-1-(4'-fluorobiphenyl-4-yl)ethyl)-4-(4-fluorophenyl)tetrahydropyrimidin-2(1H)-one isomers 1 and 2 which were separated by prep HPLC. Isomer 1: LC-MS Method 1 $t_R$=1.286 min, m/z=467.2; $^1$H NMR (CDCl$_3$) 1.45 (d, 3H), 2.02 (m, 3H), 2.18 (m, 3H), 2.83 (m, 1H), 3.31-3.50 (m, 2H), 3.88 (m, 1H), 5.68 (m, 1H), 6.80 (m, 1H), 6.92 (m, 2H), 7.04 (m, 4H), 7.21 (m, 2H), 7.28 (m, 2H), 7.39 (m, 2H). Isomer 2: LC-MS Method 1 $t_R$=1.312 min, m/z=467.2; $^1$H NMR (CDCl$_3$) 1.46 (d, 3H), 1.83 (m, 1H), 1.94-2.16 (m, 5H), 2.78 (m, 1H), 3.46 (m, 3H), 5.68 (m, 1H), 6.93-7.08 (m, 6H), 7.19 (m, 1H), 7.22 (m, 1H), 7.26 (m, 2H), 7.33 (m, 2H), 7.42 (m, 1H).

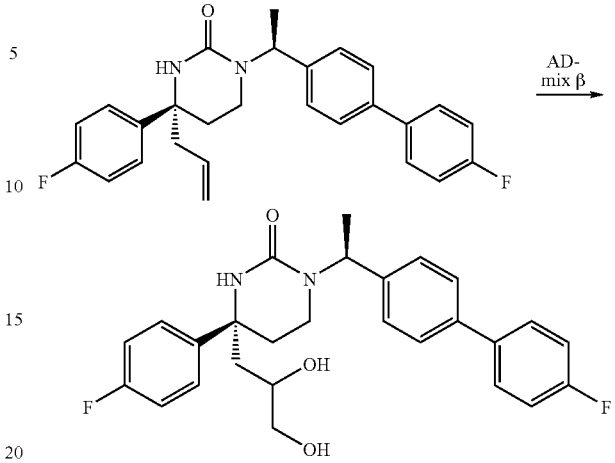

Treatment of (S)-4-allyl-1-((S)-1-(4'-fluorobiphenyl-4-yl)ethyl)-4-(4-fluorophenyl)tetrahydropyrimidin-2(1H)-one with AD-mix β following a procedure analogous to that described in Example 8 afforded (4R)-4-(2,3-dihydroxypropyl)-1-((S)-1-(4'-fluorobiphenyl-4-yl)ethyl)-4-(4-fluorophenyl)tetrahydropyrimidin-2(1H)-one isomers 3 and 4 which were separated by prep HPLC. Isomer 3: LC-MS Method 1 $t_R$=1.337 min, m/z=467.2; $^1$H NMR (CDCl$_3$) 1.31 (d, 3H), 1.84-2.03 (m, 5H), 2.52 (m, 1H), 2.68 (m, 1H), 3.33 (m, 1H), 3.42 (m, 1H), 3.79 (s, 1H), 5.66 (m, 1H), 6.79 (s, 1H), 7.03 (m, 4H), 7.29 (m, 4H), 7.44 (m, 4H). Isomer 4: LC-MS Method 1 $t_R$=1.382 min, m/z=467.2; $^1$H NMR (CDCl$_3$) 1.33 (d, 3H), 1.76-1.88 (m, 2H), 2.04 (m, 2H), 2.57 (m, 1H), 2.71 (m, 1H), 3.52 (m, 3H), 5.76 (m, 1H), 7.12 (m, 4H), 7.33 (m, 4H), 7.52 (m, 4H), 7.61 (s, 1H).

Example 10

1-((1S)-1-(4'-fluorobiphenyl-4-yl)ethyl)-4-(4-fluorophenyl)-4-(3-hydroxypropyl)tetrahydropyrimidin-2(1H)-one

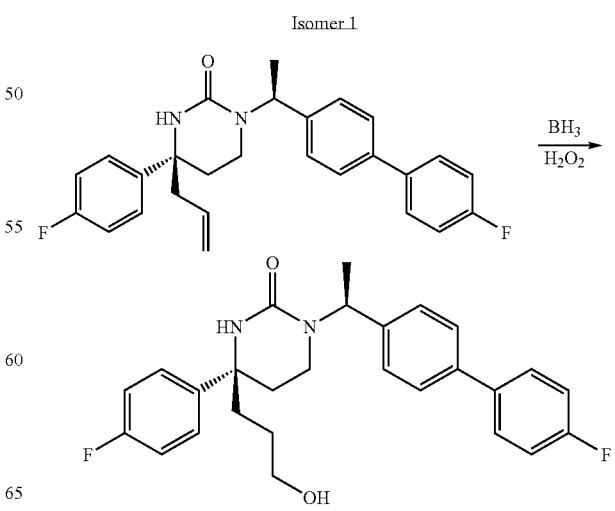

(R)-1-((S)-1-(4'-fluorobiphenyl-4-yl)ethyl)-4-(4-fluorophenyl)-4-(3-hydroxypropyl)tetrahydropyrimidin-2(1H)-one was prepared using a procedure analogous to that described in Example 7 using (R)-4-allyl-1-((S)-1-(4'-fluorobiphenyl-4-yl)ethyl)-4-(4-fluorophenyl)tetrahydropyrimidin-2(1H)-one. LC-MS Method 1 $t_R$=1.416 min, m/z=451.2; $^1$H NMR (CDCl$_3$) 1.31 (m, 2H), 1.48 (d, 3H), 1.96 (m, 4H), 2.12 (m, 1H), 2.47 (s, 1H), 2.82 (m, 1H), 3.51 (m, 2H), 5.75 (m, 1H), 6.10 (s, 1H), 6.92 (m, 2H), 7.03 (m, 2H), 7.11 (m, 2H), 7.18 (m, 2H), 7.27 (m, 2H), 7.41 (m, 2H).

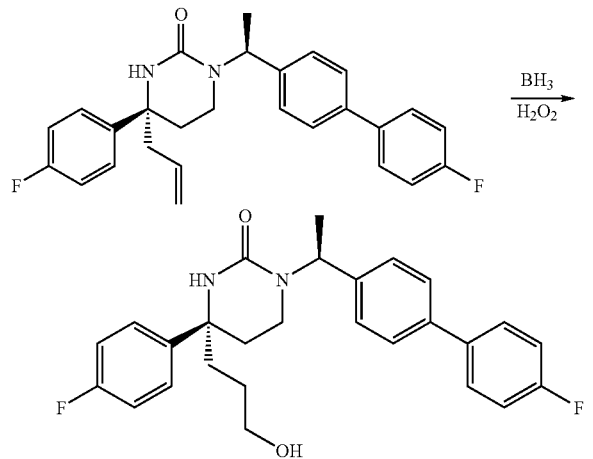

Isomer 2

(S)-1-((S)-1-(4'-fluorobiphenyl-4-yl)ethyl)-4-(4-fluorophenyl)-4-(3-hydroxypropyl)tetrahydropyrimidin-2(1H)-one was prepared using a procedure analogous to that described in Example 7 using (S)-4-allyl-1-((S)-1-(4'-fluorobiphenyl-4-yl)ethyl)-4-(4-fluorophenyl)tetrahydropyrimidin-2(1H)-one. LC-MS Method 1 $t_R$=1.466 min, m/z=451.2; $^1$H NMR (CDCl$_3$) 1.38 (d, 3H), 1.52 (m, 2H), 1.94 (m, 2H), 2.03 (m, 2H), 2.61 (m, 1H), 2.71 (m, 1H), 3.59 (m, 2H), 5.82 (s, 1H), 5.89 (m, 1H), 7.02-7.14 (m, 4H), 7.31 (m, 2H), 7.35 (m, 2H), 7.52 (m, 4H).

Example 11

1-((1S)-1-(4-bromophenyl)ethyl)-4-(4-fluorophenyl)-4-(3-hydroxypropyl)-3-methyltetrahydropyrimidin-2(1H)-one

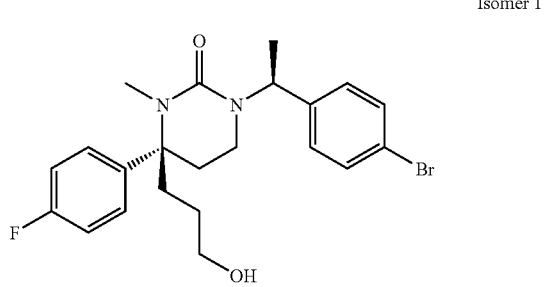

Isomer 1

(R)-1-((S)-1-(4-bromophenyl)ethyl)-4-(4-fluorophenyl)-4-(3-hydroxypropyl)-3-methyltetrahydropyrimidin-2(1H)-one was prepared from (R)-4-allyl-1-((S)-1-(4-bromophenyl)ethyl)-4-(4-fluorophenyl)-3-methyltetrahydropyrimidin-2(1H)-one following a procedure analogous to that described in Example 10. (R)-4-allyl-1-((S)-1-(4-bromophenyl)ethyl)-4-(4-fluorophenyl)-3-methyltetrahydropyrimidin-2(1H)-one was prepared from (R)-4-allyl-1-((S)-1-(4-bromophenyl)ethyl)-4-(4-fluorophenyl)tetrahydropyrimidin-2(1H)-one following a procedure analogous to that described in Example 3. LC-MS Method $t_R$=2.45 min, m/z=471.1; $^1$H NMR (CDCl$_3$) δ=1.28 (m, 2H), 1.49 (m, 3H), 1.72 (m, 2H), 1.90 (m, 1H), 2.18 (m, 3H), 2.70 (m, 1H), 2.80 (m, 3H), 3.69 (m, 2H), 5.82 (m, 1H), 6.91 (m, 2H), 7.06 (m, 4H), 7.32 (m, 2H).

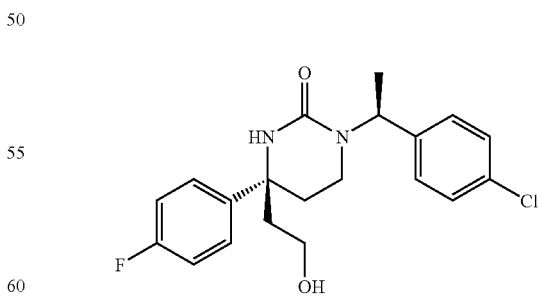

Isomer 2

(S)-1-((S)-1-(4-bromophenyl)ethyl)-4-(4-fluorophenyl)-4-(3-hydroxypropyl)-3-methyltetrahydropyrimidin-2(1H)-one was prepared from (S)-4-allyl-1-((S)-1-(4-bromophenyl)ethyl)-4-(4-fluorophenyl)-3-methyltetrahydropyrimidin-2(1H)-one following a procedure analogous to that described in Example 10. (S)-4-allyl-1-((S)-1-(4-bromophenyl)ethyl)-4-(4-fluorophenyl)-3-methyltetrahydropyrimidin-2(1H)-one was prepared from (S)-4-allyl-1-((S)-1-(4-bromophenyl)ethyl)-4-(4-fluorophenyl)tetrahydropyrimidin-2(1H)-one following a procedure analogous to that described in Example 3. LC-MS Method 1 $t_R$=1.383 min, m/z=449.1; $^1$H NMR (CDCl$_3$) δ=1.20 (m, 1H), 1.35 (m, 3H), 1.60 (m, 2H), 1.71 (m, 1H), 1.98 (m, 2H), 2.12 (m, 1H), 2.49 (m, 1H), 2.64 (m, 1H), 2.83 (m, 3H), 3.70 (m, 2H), 5.85 (m, 1H), 7.01 (m, 2H), 7.13 (m, 4H), 7.39 (m, 2H).

Example 12

(S)-1-((S)-1-(4-chlorophenyl)ethyl)-4-(4-fluorophenyl)-4-(2-hydroxyethyl)tetrahydropyrimidin-2(1H)-one The title compound was prepared from (R)-4-allyl-1-((S)-1-(4-chlorophenyl)ethyl)-4-(4-fluorophenyl)tetrahydropyrimidin-2(1H)-one following a procedure analogous to that described in Example 6. LC-MS Method 2 $t_R$=2.283 min, m/z=399.1; $^1$H NMR (CDCl$_3$) δ=0.71 (s, 1H), 1.46 (m, 3H), 2.03 (m, 4H), 2.1 (m, 1H), 2.77 (m, 1H), 3.40 (m, 1H), 3.75 (m, 1H), 5.78 (m, 1H), 7.00 (m, 1H), 7.13 (m, 4H), 7.15 (m, 2H), 7.26 (m, 2H).

Example 13

1-((1S)-1-(4-chlorophenyl)ethyl)-4-(4-fluorophenyl)-4-(3-hydroxypropyl)tetrahydropyrimidin-2(1H)-one

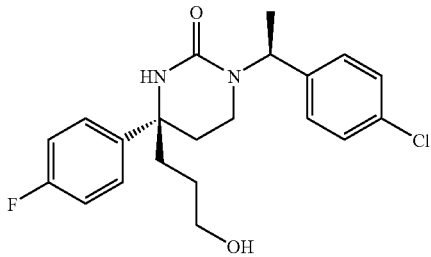 [SMILES: C[C@@H](c1ccc(Cl)cc1)N1CC[C@](CCCO)(c2ccc(F)cc2)NC1=O]

The title compound was prepared from 4-allyl-1-((1S)-1-(4-chlorophenyl)ethyl)-4-(4-fluorophenyl)tetrahydropyrimidin-2(1H)-one following a procedure analogous to that described in Example 10. LC-MS Method 2 $t_R$=2.283 min, m/z=413.1; $^1$H NMR (CDCl$_3$) δ=1.28 (m, 2H), 1.30 (m, 3H), 1.87 (m, 5H), 1.90 (m, 1H), 2.79 (m, 1H), 3.53 (m, 1H), 5.71 (m, 1H), 5.90 (m, 1H), 6.98 (m, 4H), 7.08 (m, 2H), 7.19 (m, 2H).

Example 14

1-((1S)-1-(4'-fluorobiphenyl-4-yl)ethyl)-4-(3-hydroxypropyl)-4-phenyltetrahydropyrimidin-2(1H)-one Isomer 1

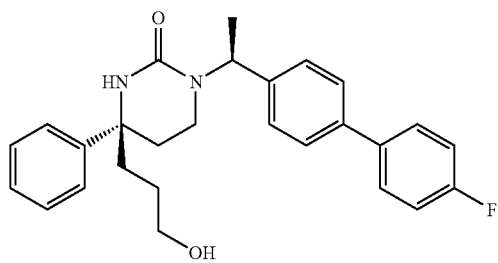

(R)-1-((S)-1-(4'-fluorobiphenyl-4-yl)ethyl)-4-(3-hydroxypropyl)-4-phenyltetrahydropyrimidin-2(1H)-one was prepared from (R)-4-allyl-1-((S)-1-(4'-fluorobiphenyl-4-yl)ethyl)-4-phenyltetrahydropyrimidin-2(1H)-one following a procedure analogous to that described in Example 10. LC-MS Method 1 $t_R$=1.4 min, m/z=433.2; $^1$H NMR (CDCl$_3$) δ=1.10 (m, 1H), 1.47 (m, 3H), 1.98 (m, 1H), 2.0 (m, 3H), 2.11 (m, 1H), 2.75 (m, 1H), 3.52 (m, 2H), 5.60 (m, 1H), 5.75 (m, 1H), 7.02 (m, 2H), 7.19 (m, 4H), 7.27 (m, 5H), 7.29 (m, 2H).

Isomer 2

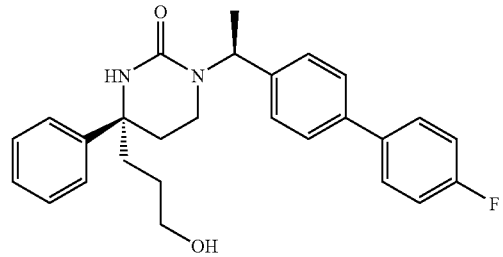

(S)-1-((S)-1-(4'-fluorobiphenyl-4-yl)ethyl)-4-(3-hydroxypropyl)-4-phenyltetrahydropyrimidin-2(1H)-one was prepared from (S)-4-allyl-1-((S)-1-(4'-fluorobiphenyl-4-yl)ethyl)-4-phenyltetrahydropyrimidin-2(1H)-one following a procedure analogous to that described in Example 10. LC-MS Method 1 $t_R$=1.467 min, m/z=433.2; $^1$H NMR (CDCl$_3$) δ=1.44 (m, 3H), 1.45 (m, 1H), 1.52 (m, 2H), 1.62 (m, 3H), 2.60 (m, 2H), 3.52 (m, 2H), 5.64 (m, 1H), 5.80 (m, 1H), 7.07 (m, 1H), 7.19 (m, 2H), 7.25 (m, 2H), 7.31 (m, 5H), 7.42 (m, 3H).

Example 15

(R)-1-((S)-1-cyclohexylethyl)-4-(3-hydroxypropyl)-4-phenyltetrahydropyrimidin-2(1H)-one

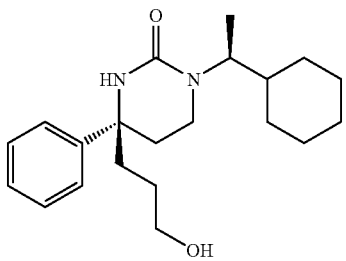 [SMILES: C[C@@H](C1CCCCC1)N1CC[C@](CCCO)(c2ccccc2)NC1=O]

The title compound was prepared from (R)-4-allyl-1-((S)-1-cyclohexylethyl)-4-phenyltetrahydropyrimidin-2(1H)-one following a procedure analogous to that described in Example 10. (R)-4-allyl-1-((S)-1-cyclohexylethyl)-4-phenyltetrahydropyrimidin-2(1H)-one was prepared following a procedure analogous to that described for Example 2 Isomer 1. LC-MS Method 1 $t_R$=1.129 min, m/z=345; $^1$H NMR (CDCl$_3$) δ=0.82 (m, 2H), 1.10 (m, 4H), 1.56 (m, 6H), 1.98 (m, 3H), 2.15 (m, 2H), 2.40 (m, 1H), 2.60 (m, 1H), 2.95 (m, 1H), 3.51 (m, 2H), 3.98 (m, 1H), 7.29 (m, 5H).

Example 16

(R)-4-(4-fluorophenyl)-4-(3-hydroxypropyl)-1-((S)-1-(4-methoxyphenyl)ethyl)tetrahydropyrimidin-2(1H)-one

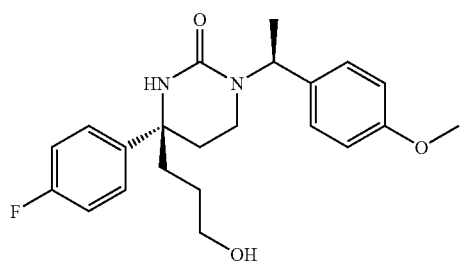 [SMILES: COc1ccc([C@H](C)N2CC[C@](CCCO)(c3ccc(F)cc3)NC2=O)cc1]

The title compound was prepared from (R)-4-allyl-4-(4-fluorophenyl)-1-((S)-1-(4-methoxyphenyl)ethyl)tetrahydropyrimidin-2(1H)-one following a procedure analogous to that described in Example 10. (R)-4-allyl-4-(4-fluorophenyl)-1-((S)-1-(4-methoxyphenyl)ethyl)tetrahydropyrimidin-2(1H)-one was prepared following a procedure analogous to that described for Example 2 Isomer 1. LC-MS Method 2 $t_R$=1.154 min, m/z=384; $^1$H NMR (CDCl$_3$) δ=1.30 (m, 2H), 1.48 (m, 3H), 1.98 (m, 4H), 2.75 (m, 1H), 3.25 (m, 2H), 3.56 (m, 3H), 3.67 (s, 3H), 5.75 (m, 1H), 6.70 (d, 2H), 6.99 (m, 4H), 7.20 (m, 2H).

Example 17

(S)-4-(4-fluorophenyl)-4-(2-hydroxyethyl)-1-((S)-1-(4-methoxyphenyl)ethyl)tetrahydropyrimidin-2(1H)-one

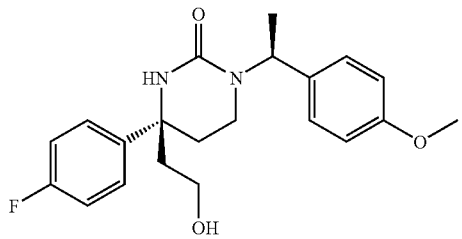 [SMILES: COc1ccc([C@H](C)N2CC[C@](CCO)(c3ccc(F)cc3)NC2=O)cc1]

The title compound was prepared from (R)-4-allyl-4-(4-fluorophenyl)-1-((S)-1-(4-methoxyphenyl)ethyl)tetrahydropyrimidin-2(1H)-one following a procedure analogous to that described in Example 6. (R)-4-allyl-4-(4-fluorophenyl)-1-((S)-1-(4-methoxyphenyl)ethyl)tetrahydropyrimidin-2(1H)-one was prepared following a procedure analogous to that described for Example 2 Isomer 1. LC-MS Method 2 $t_R$=1.242 min, m/z=373; $^1$H NMR (CDCl$_3$) δ=1.38 (d, 3H), 1.94 (m, 4H), 2.13 (m, 1H), 2.70 (m, 1H), 3.34 (m, 1H), 3.69 (m, 3H), 5.70 (m, 1H), 6.57 (s, 1H), 6.95 (m, 2H), 7.00 (m, 4H), 7.19 (m, 2H).

Example 18

(R)-1-((S)-1-(4-bromophenyl)ethyl)-4-(4-fluorophenyl)-4-(3-hydroxypropyl)tetrahydropyrimidin-2(1H)-one

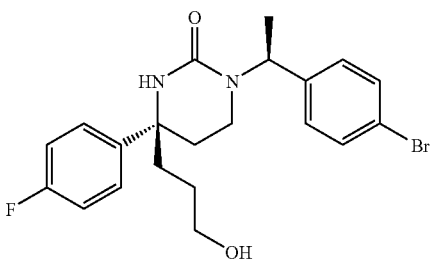 [SMILES: C[C@@H](c1ccc(Br)cc1)N1CC[C@](CCCO)(c2ccc(F)cc2)NC1=O]

The title compound was prepared from (R)-4-allyl-1-((S)-1-(4-bromophenyl)ethyl)-4-(4-fluorophenyl)tetrahydropyrimidin-2(1H)-one following a procedure analogous to that described in Example 7. LC-MS Method 1 $t_R$=1.642 min, m/z=435; $^1$H NMR (CDCl$_3$) δ=1.30 (m, 3H), 1.40 (d, 4H), 1.45 (m, 1H), 1.87 (m, 1H), 1.90 (m, 3H), 2.10 (m, 1H), 2.76 (m, 1H), 3.53 (t, 2H), 5.68 (m, 1H), 5.72 (s, 1H), 6.96 (t, 4H), 7.15 (m, 2H), 7.24 (m, 2H).

Example 19

N-(3-((R)-1-((S)-1-(4-bromophenyl)ethyl)-4-(4-fluorophenyl)-2-oxohexahydropyrimidin-4-yl)propyl)methanesulfonamide

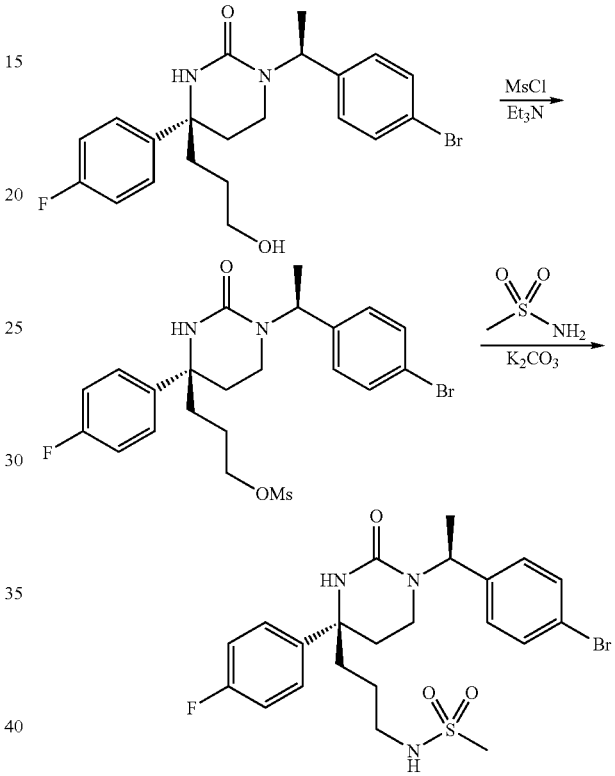

Step 1

To a solution of (R)-1-((S)-1-(4-bromophenyl)ethyl)-4-(4-fluorophenyl)-4-(3-hydroxypropyl)tetrahydropyrimidin-2(1H)-one (50 mg, 0.12 mmol) and triethylamine (161 mg, 1.59 mmol) in CH$_2$Cl$_2$ (5 mL) was added methanesulfonyl chloride (91 mg, 0.8 mmol) at 0° C., and the reaction mixture was stirred at rt till the reaction was over. The reaction was quenched with H$_2$O, and the mixture was extracted with EtOAc. The organic phase was washed with brine, dried over Na$_2$SO$_4$, filtered and concentrated to give crude 3-((R)-1-((S)-1-(4-bromophenyl)ethyl)-4-(4-fluorophenyl)-2-oxohexahydropyrimidin-4-yl)propyl methanesulfonate (58 mg, 95%), which was used for the next step without further purification.

Step 2

To a solution of 3-((R)-1-((S)-1-(4-bromophenyl)ethyl)-4-(4-fluorophenyl)-2-oxohexa hydropyrimidin-4-yl)propyl methanesulfonate (58 mg, 0.11 mmol) and methanesulfonamide (105 mg, 1.10 mmol) in acetone (10 mL) was added K$_2$CO$_3$ (31 mg, 0.22 mmol), and the mixture was refluxed overnight. The reaction was quenched with water, and the mixture was extracted with EtOAc. After removal of the solvent, the mixture was extracted with EtOAc, and the organic solution was washed with brine, dried over Na$_2$SO$_4$, filtered and concentrated to give the crude product, which was purified by preparative TLC and preparative HPLC to give N-(3-((R)-1-((S)-1-(4-bromophenyl)ethyl)-4-(4-fluorophenyl)-2-oxohexahydropyrimidin-4-yl)propyl)methanesulfonamide (8 mg, 14%). ¹H NMR (CDCl₃): 1.18☐m, 1H), 1.45 (d, 3H), 1.50 (m, 1H), 1.88-2.16 (m, 5H), 2.84 (m, 4H), 3.02 (m, 2H), 4.70 (s, 1H), 5.63 (m, 1H), 6.88-6.98 (m, 4H), 7.12 (m, 2H), 7.30 (m, 2H). LC-MS Method 1 $t_R$=1.146 min, m/z=512.

Example 20

(S)-1-((S)-1-(4-bromophenyl)ethyl)-4-(2-hydroxy-2-methylpropyl)-4-phenyltetrahydropyrimidin-2(1H)-one

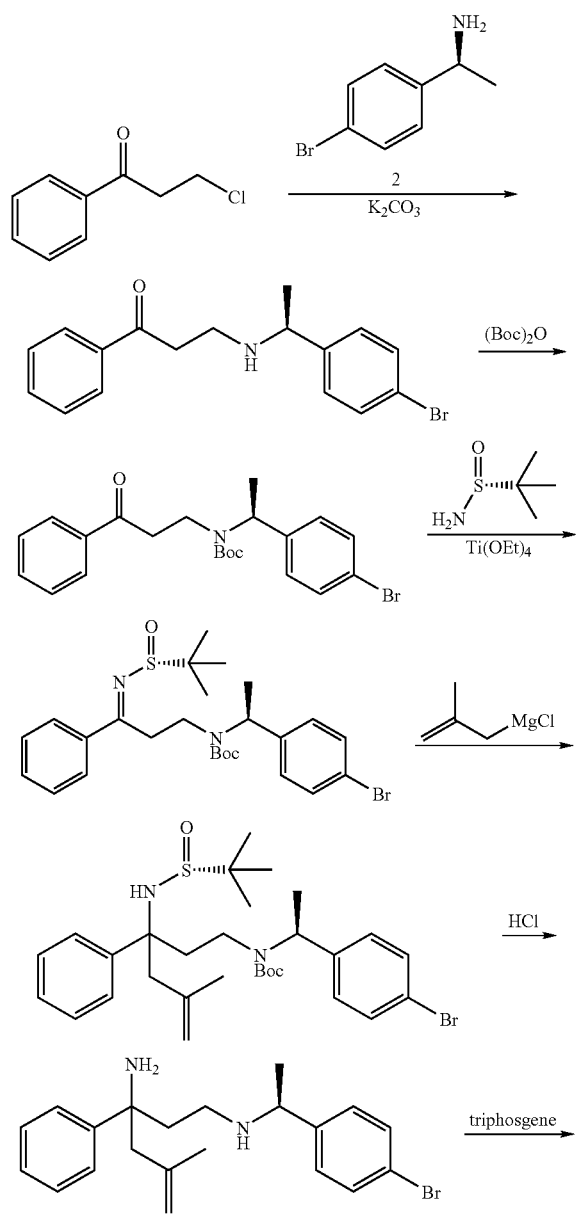

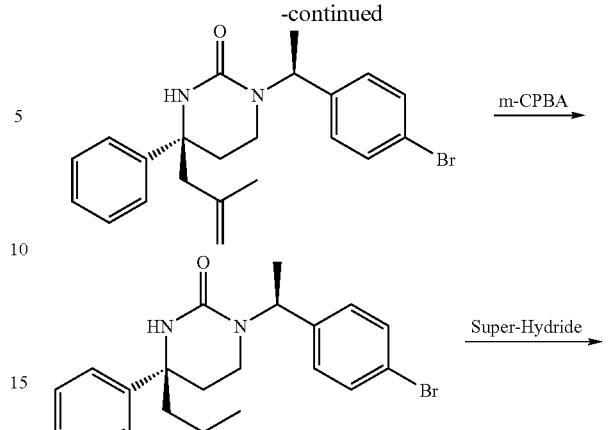

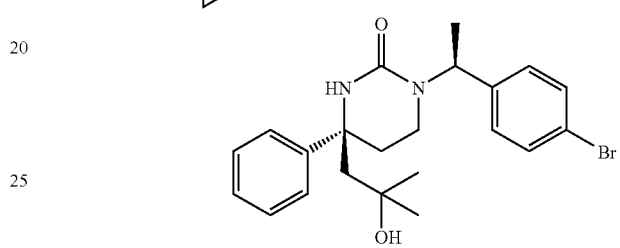

Step 1. (S)-3-(1-(4-bromophenyl)ethylamino)-1-phenylpropan-1-one

To a solution of (S)-1-(4-bromophenyl)ethanamine (100 g, 0.502 mol) and K₂CO₃ (138.8 g, 0.10 mol) in acetonitrile (1000 mL) was added a solution of 3-chloro-1-phenyl-propan-1-one (84.4 g, 0.502 mol) in acetonitrile (100 mL). The reaction mixture was stirred overnight. The solid was filtered, and the filtrate was concentrated to give crude (S)-3-(1-(4-bromo-phenyl)ethylamino)-1-phenylpropan-1-one (110 g, 66.2%), which was used in the next step without further purification.

Step 2. (S)-tert-butyl 1-(4-bromophenyl)ethyl(3-oxo-3-phenylpropyl)carbamate

To a solution of (S)-3-(1-(4-bromophenyl)ethylamino)-1-phenylpropan-1-one (100 g, 0.302 mol) in CH₂Cl₂(1 L) was added Et₃N (92 g, 0.906 mol) and (Boc)₂O(98 g, 0.45 mol). The mixture was stirred overnight, the reaction was washed with water, extracted with CH₂Cl₂, the combined organic phase was washed with brine, dried over Na₂SO₄, and concentrated to give crude (S)-tert-butyl 1-(4-bromophenyl)ethyl (3-oxo-3-phenylpropyl)carbamate (78 g, 60%) which was purified by column chromatography.

Step 3. (S,Z)-tert-butyl 1-(4-bromophenyl)ethyl(3-(tert-butylthioimino)-3-phenylpropyl)carbamate A mixture of (S)-tert-butyl 1-(4-bromophenyl)ethyl(3-oxo-3-phenylpropyl)carbamate (30 g, 0.069 mol), (R)-2-methylpropane-2-sulfinamide (8.42 g, 0.069 mol), and Ti(i-OPr)₄ (31.4 g, 0.138 mol) in THF (300 mL) was heated to reflux overnight. The mixture was treated with brine, and the precipitate was filtered. The filtrate was concentrated to give (S,Z)-tert-butyl 1-(4-bromophenyl)ethyl(3-(tert-butylthioimino)-3-phenylpropyl)carbamate (20 g, 55%) which was used in the next step without further purification. $^1$H NMR (CDCl$_3$): δ=1.23 (s, 9H), 1.32 (s, 9H), 1.46 (d, 3H), 1.70-1.86 (m, 2H), 3.24-3.75 (m, 2H), 4.08 (m, 1H), 7.09-7.91 (m, 9H).

Step 4. tert-butyl(S)-1-(4-bromophenyl)ethyl(3-((R)-1,1-dimethylethylsulfinamido)-5-methyl-3-phenyl-hex-5-enyl)carbamate To a solution of (S,Z)-tert-butyl 1-(4-bromophenyl)ethyl (3-(tert-butylthioimino)-3-phenylpropyl)carbamate (20 g, 0.037 mol) in THF (200 mL) was added (2-methylallyl)magnesium chloride (5.0 g, 0.044 mol) under nitrogen at −78° C. The mixture was stirred for 2 h. The reaction was quenched with satd aq NH$_4$Cl. The organic phase was separated and concentrated to give crude tert-butyl(S)-1-(4-bromophenyl)ethyl(3-((R)-1,1-dimethylethylsulfinamido)-5-methyl-3-phenylhex-5-enyl)carbamate (6.5 g, 30%), which was purified by column chromatography.

Step 5. N$^1$—((S)-1-(4-bromophenyl)ethyl)-5-methyl-3-phenylhex-5-ene-1,3-diamine A mixture of tert-butyl (S)-1-(4-bromophenyl)ethyl(3-((R)-1,1-dimethylethylsulfinamido)-5-methyl-3-phenylhex-5-enyl)carbamate (6.5 g, 0.011 mol) in HCl/dioxane (70 mL) was stirred for 1 hour at 0° C. The mixture was concentrated to give the residue, which was treated with satd aq Na$_2$CO$_3$. The resulting mixture was extracted with EtOAc, and the combined organic layer was concentrated to afford crude N$^1$—((S)-1-(4-bromophenyl)ethyl)-5-methyl-3-phenylhex-5-ene-1,3-diamine (2.97 g, 70%), which was used for the next step without purification.

Step 6. 1-[1-(4-Bromo-phenyl)-ethyl]-4-(2-methyl-allyl)-4-phenyl-tetrahydro-pyrimidin-2-one To a solution of N$^1$-[1-(4-Bromo-phenyl)-ethyl]-5-methyl-3-phenyl-hex-5-ene-1,3-diamine (2.97 g, 0.007 mol) and Et$_3$N (3.53 g, 0.035 mol) was added triphosgene (0.58 g, 0.002 mol) at 0° C. The resulting mixture was stirred for 3 h. The mixture was washed with water, the organic layer was separated, and concentrated to give the crude (R)-1-((S)-1-(4-bromophenyl)ethyl)-4-(2-methylallyl)-4-phenyltetrahydropyrimidin-2(1H)-one (1.1 g, 40%). which was purified by column chromatography. $^1$H NMR (CDCl$_3$): δ=1.24 (s, 3H), 1.38 (m, 1H), 1.43 (d, 3H), 1.56 (m, 1H), 1.88 (m, 1H), 2.09 (m, 1H), 2.12 (m, 1H), 2.44 (m, 1H), 2.64 (m, 2H) 4.72 (s, 1H), 4.83 (s, 1H), 5.21 (s, 1H), 5.74 (m, 1H), 6.90 (m, 2H), 6.92-7.14 (m, 2H), 7.18-7.38 (m, 5H).

Step 7. (4S)-1-((S)-1-(4-bromophenyl)ethyl)-4-((2-methyloxiran-2-yl)methyl)-4-phenyltetrahydropyrimidin-2(1H)-one To a solution of (R)-1-((5)-1-(4-bromophenyl)ethyl)-4-(2-methylallyl)-4-phenyltetrahydropyrimidin-2(1H)-one (0.6 g, 1.45 mmol) in CH$_2$Cl$_2$ (15 mL) was added to m-CPBA (0.59 g, 2.9 mmol). The resulting solution was stirred overnight. The mixture was diluted with methyl tert-butyl ether (100 mL) and washed with 30 wt % aq sodium thiosulfate (3×50 mL) and saturated aqueous sodium bicarbonate (3×50 mL). The organic layer was dried over Na$_2$SO$_4$, filtered and then concentrated to afford (4S)-1-((S)-1-(4-bromophenyl)ethyl)-4-((2-methyloxiran-2-yl)methyl)-4-phenyltetrahydropyrimidin-2(1H)-one (0.61 g, Yield: 98%).

Step 8: (S)-1-((S)-1-(4-bromophenyl)ethyl)-4-(2-hydroxy-2-methylpropyl)-4-phenyltetrahydropyrimidin-2(1H)-one To a solution of (4S)-1-((S)-1-(4-bromophenyl)ethyl)-4-((2-methyloxiran-2-yl)methyl)-4-phenyltetrahydropyrimidin-2(1H)-one (0.61 g, 1.42 mmol) in anhydrous tetrahydrofuran (5 mL) was added to Super Hydride (2.56 mL, 2.56 mmol) at 0-5° C. The addition is exothermic and addition was controlled to maintain T$_{int}$=<8° C. The mixture was stirred for 2 h at 0-5° C. and allowed to warm to 10-15 0° C. over 3 h. A solution of hydrogen peroxide (5 mL of a 30 wt % aqueous solution diluted with 50 mL of water) was added. The temperature was controlled to maintain T$_{int}$=<25° C. The resulting solution was diluted with methyl tert-butyl ether (MTBE) (200 mL) and washed with water (200 mL) followed by 30 wt % aq solution of sodium thiosulfate (300 mL). The organic solution was dried over Na$_2$SO$_4$, filtered and then concentrated to dryness. The residue was purified by column to afford (S)-1-((S)-1-(4-bromophenyl)ethyl)-4-(2-hydroxy-2-methylpropyl)-4-phenyltetrahydropyrimidin-2(1H)-one (0.5 g, Yield: 82%). $^1$H NMR (MeOD): 0.58 (s, 3H), 1.17 (s, 3H), 1.44-1.46 (d, 3H), 1.90-1.94 (m, 2H), 2.05-2.08 (m, 1H), 2.16-2.18 (m, 1H), 2.24-2.27 (m, 1H), 2.83-2.86 (m, 1H), 5.65-5.67 (m, 1H), 7.04-7.06 (m, 2H), 7.22-7.23 (m, 1H), 7.27-7.33 (m, 6H). LC-MS Method 2 t$_R$=1.296 min, m/z=433.

Example 21

(S)-4-(2-hydroxy-2-methylpropyl)-1-((S)-1-(4-(1-methyl-2-oxo-1,2-dihydropyridin-4-yl)phenyl)ethyl)-4-phenyltetrahydropyrimidin-2(1H)-one

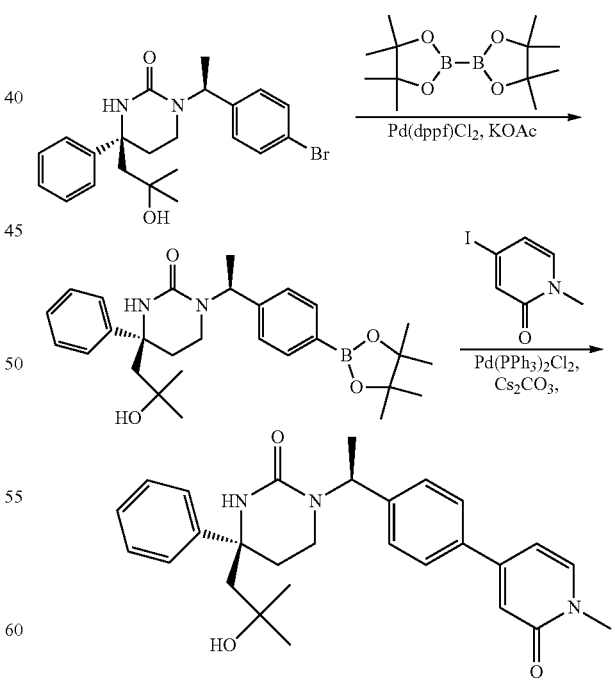

Step 1

To a solution of (S)-1-((S)-1-(4-bromophenyl)ethyl)-4-(2-hydroxy-2-methylpropyl)-4-phenyltetrahydropyrimidin-2(1H)-one (260 mg, 0.6 mmol) and 4,4,4',4',5,5,5',5'-octamethyl-2,2'-bi(1,3,2-dioxaborolane) (244 mg, 0.96 mmol) in dry DMSO (20 mL) was added KOAc (188 mg, 1.92 mmol) and Pd(dppf)Cl₂ (14.7 mg, 0.02 mmol) under N₂ atmosphere. After addition, the mixture was warmed to 90° C. for 2 h. When TLC showed the starting material had disappeared, the solid was filtered off. Water (50 mL) and EtOAc (50 mL) were added, and the mixture was extracted with EtOac (3×50 mL). The combined organic layer was washed with brine (50 mL), dried over Na₂SO₄, filtered, and concentrated. The residue was purified by prep TLC to afford (S)-4-(2-hydroxy-2-methylpropyl)-4-phenyl-1-((S)-1-(4-(4,4,5,5-tetramethyl-1,3,2-dioxaborolan-2-yl)phenyl)ethyl)tetrahydropyrimidin-2(1H)-one (0.2 g, yield: 70%).

Step 2

To a solution of (S)-4-(2-hydroxy-2-methylpropyl)-4-phenyl-1-((S)-1-(4-(4,4,5,5-tetramethyl-1,3,2-dioxaborolan-2-yl)phenyl)ethyl)tetrahydropyrimidin-2(1H)-one (170 mg, 0.36 mmol) and 4-iodo-1-methylpyridin-2(1H)-one (100 mg, 0.43 mmol) in dry 1,4-dioxane (5 mL) was added 2M aq Cs₂CO₃ (1 mL) and Pd(PPh₃)Cl₂ (21.4 mg, 0.03 mmol). After addition, the mixture was heated to reflux for 2 h under N₂ atmosphere. The solid was filtered off and diluted with water (30 mL) and EtOAc (30 mL). The mixture was extracted with EtOAc (3×40 mL), and the combined organic layer was washed with brine (50 mL), dried over Na₂SO₄, filtered, and concentrated to dryness. The residue was purified by prep TLC to afford (S)-4-(2-hydroxy-2-methylpropyl)-1-((S)-1-(4-(1-methyl-2-oxo-1,2-dihydropyridin-4-yl)phenyl)ethyl)-4-phenyltetrahydropyrimidin-2(1H)-one (90 mg, yield: 54.4%). ¹H NMR (CDCl₃): 0.661 (s, 3H), 1.23 (s, 3H), 1.49-1.50 (m, 3H), 1.98-2.02 (m, 2H), 2.05-2.13 (m, 1H), 2.17-2.18 (m, 2H), 2.60-2.63 (m, 1H), 2.74-2.78 (m, 1H), 3.57 (s, 3H), 5.87-5.92 (m, 1H), 6.35-6.37 (m, 1H), 6.71-6.72 (d, 1H), 7.18-7.22 (m, 2H), 7.23-7.25 (m, 1H), 7.30-7.32 (m, 2H), 7.33-7.37 (m, 5H).

Example 22

(R)-1-((S)-1-cyclohexylethyl)-4-(3-hydroxypropyl)-3-methyl-4-phenyltetrahydropyrimidin-2(1H)-one

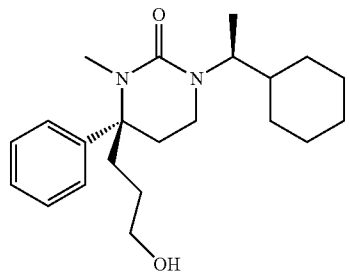 [SMILES: C[C@@H](C1CCCCC1)N1CC[C@](CCCO)(c2ccccc2)N(C)C1=O]

The title compound was prepared from (R)-4-allyl-1-((S)-1-cyclohexylethyl)-3-methyl-4-phenyltetrahydropyrimidin-2(1H)-one following a procedure analogous to that described in Example 7. (R)-4-allyl-1-((S)-1-cyclohexylethyl)-3-methyl-4-phenyltetrahydropyrimidin-2(1H)-one was prepared from (R)-4-allyl-1-((S)-1-cyclohexylethyl)-4-phenyltetrahydropyrimidin-2(1H)-one following a procedure analogous to that described in Example 3. LC-MS Method 2 $t_R$=1.408 min, m/z=359.1; ¹H NMR (CDCl₃) δ=1.06 (m, 3H), 1.10 (m, 3H), 1.23 (m, 3H), 1.52 (m, 7H), 1.75 (m, 2H), 1.98 (m, 1H), 2.15 (m, 2H), 2.60 (m, 1H), 2.87 (m, 3H), 3.70 (m, 2H), 4.22 (m, 11-1), 7.17 (m, 4H), 7.28 (m, 2H).

Example 23

3-((R)-1-((S)-1-(4-bromophenyl)ethyl)-2-oxo-4-phenylhexahydropyrimidin-4-yl)-2,2-dimethylpropanenitrile

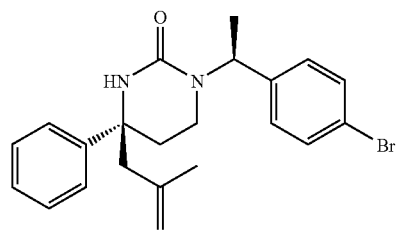

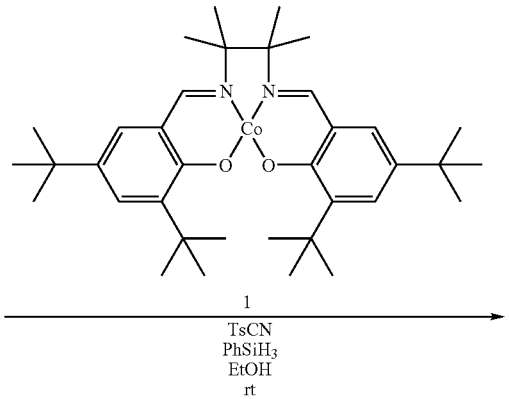

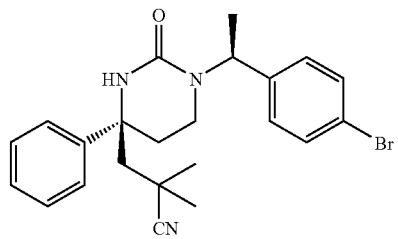

Cobalt catalyst 1 (1.32 mg, 0.002 mmol, 1 mol %) was dissolved in EtOH (8 mL; absolute) at rt under argon, (R)-1-((S)-1-(4-bromophenyl)ethyl)-4-(2-methylallyl)-4-phenyltetrahydropyrimidin-2(1H)-one (82.6 mg, 0.2 mmol), TsCN (54 mg, 0.3 mmol), tBuOOH (6 mg, 0.06 mmol), and PhSiH$_3$ (21.6 mg, 0.2 mmol) were added. The resulting solution was stirred at rt for 3 h. The solvent was removed by evaporation, and the residue was purified by prep HPLC to afford 3-((R)-1-((S)-1-(4-bromophenyl)ethyl)-2-oxo-4-phenylhexahydropyrimidin-4-yl)-2,2-dimethylpropanenitrile (4 mg, 4.5%) as a white solid. $^1$H NMR (CD$_3$OD): δ 1.24 (s, 3H), 1.36 (s, 3H), 1.47-1.48 (m, 3H), 2.04-2.07 (m, 2H), 2.07 (m, 1H), 2.22-2.26 (m, 2H), 2.98-3.02 (m, 1H), 5.65-5.67 (m, 1H), 6.95-6.97 (m, 1H), 7.25-7.30 (m, 3H), 7.33-7.37 (m, 4H).

Cobalt catalyst 1 was prepared as follows: A 50 mL flask was charged with N,N'-bis(3,5-di-tert-butylsalicylidene)-1,1,2,2-tetramethylethenediamine (0.4302 g, 0.78 mmol, 1.0 equiv), EtOH (17 mL), and Co(OAc)$_2$ (0.1385 g, 0.78 mmol, 1.0 equiv). The mixture was degassed and then heated to reflux under nitrogen for 3 h, cooled to room temperature. The precipitate was filtered and the purple solid was washed with EtOH (10 mL) and dried under high vacuum to give 0.3533 g (75%) of the cobalt(II) complex.

LC-MS Method 2 $t_R$=1.921 min, m/z=440.1; $^1$H NMR (CD$_3$OD) δ=1.25 (s, 3H), 1.49 (s, 3H), 2.04 (d, 3H), 2.34 (m, 2H), 2.38 (m, 1H), 2.40 (m, 2H), 3.02 (m, 1H), 5.67 (m, 1H), 6.97 (m, 2H), 7.26 (m, 3H), 7.38 (m, 4H).

Example 24

2,2-dimethyl-3-((R)-1-((S)-1-(4-(1-methyl-2-oxo-1,2-dihydropyridin-4-yl)phenyl)ethyl)-2-oxo-4-phenylhexahydropyrimidin-4-yl)propanenitrile

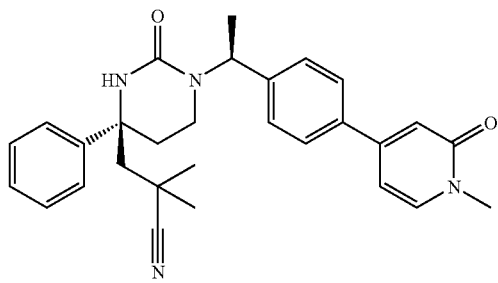 [SMILES: C[C@@H](c1ccc(-c2ccn(C)c(=O)c2)cc1)N1CC[C@](CC(C)(C)C#N)(c2ccccc2)NC1=O]

The title compound was prepared from 3-((R)-1-((S)-1-(4-bromophenyl)ethyl)-2-oxo-4-phenylhexahydropyrimidin-4-yl)-2,2-dimethylpropanenitrile following procedures analogous to those described in Example 21 Steps 1 and 2. LC-MS Method 2 $t_R$=0.848 min, m/z=469.1; $^1$H NMR (CD$_3$OD) δ=0.89 (s, 3H), 1.32 (s, 3H), 1.51 (d, 3H), 1.92 (m, 1H), 2.13 (m, 1H), 2.26 (m, 1H), 2.40 (m, 1H), 2.49 (m, 1H), 3.06 (m, 1H), 3.51 (m, 3H), 5.73 (m, 1H), 6.56 (m, 1H), 6.59 (m, 1H), 7.09 (m, 2H), 7.20 (m, 3H), 7.26 (m, 2H), 7.41 (m, 2H), 7.61 (m, 1H).

Biological Test Example 1

The inhibition of microsomal preparation of 11β-HSD1 by compounds of the invention was measured essentially as previously described (K. Solly, S. S. Mundt, H. J. Zokian, G. J. Ding, A. Hermanowski-Vosatka, B. Strulovici, and W. Zheng, High-Throughput Screening of 11-Beta-Hydroxysteroid Dehydrogenase Type 1 in Scintillation Proximity Assay Format. Assay Drug Dev Technol 3 (2005) 377-384). All reactions were carried out at room temperature in 96 well clear flexible PET Microbeta plates (PerkinElmer). The assay begins by dispensing 49 μl of substrate solution (50 mM HEPES, pH 7.4, 100 mM KCl, 5 mM NaCl, 2 mM MgCl$_2$, 2 mM NADPH and 160 nM [$^3$H]cortisone (1 Ci/mmol)) and mixing in 1 μL of the test compounds in DMSO previously diluted in half-log increments (8 points) starting at 0.1 mM. After a 10 minute pre-incubation, 50 μL of enzyme solution containing microsomes isolated from CHO cells overexpressing human 11β-HSD1 (10-20 μg/ml of total protein) was added, and the plates were incubated for 90 minutes at room temperature. The reaction was stopped by adding 50 μl of the SPA beads suspension containing 10 μM 18β-glycyrrhetinic acid, 5 mg/ml protein A coated YSi SPA beads (GE Healthcare) and 3.3 μg/ml of anti-cortisol antibody (East Coast Biologics) in Superblock buffer (Bio-Rad). The plates were shaken for 120 minutes at room temperature, and the SPA signal corresponding to [$^3$H]cortisol was measured on a Microbeta plate reader.

Biological Test Example 2

The inhibition of 11β-HSD1 by compounds of this invention was measured in whole cells as follows. Cells for the assay were obtained from two sources: fully differentiated human omental adipocytes from Zen-Bio, Inc.; and human omental pre-adipocytes from Lonza Group Ltd. Pre-differentiated omental adipocytes from Zen-Bio Inc. were purchased in 96-well plates and were used in the assay at least two weeks after differentiation from precursor preadipocytes. Zen-Bio induced differentiation of pre-adipocytes by supplementing medium with adipogenic and lipogenic hormones (human insulin, dexamethasone, isobutylmethylxanthine and PPAR-gamma agonist). The cells were maintained in full adipocyte medium (DMEM/Ham's F-12 (1:1, v/v), HEPES pH 7.4, fetal bovine serum, penicillin, streptomycin and Amphotericin B, supplied by Zen-Bio, Inc.) at 37° C., 5% CO$_2$.

Pre-adipocytes were purchased from Lonza Group Ltd. and placed in culture in Preadipocyte Growth Medium-2 supplemented with fetal bovine serum, penicillin, and streptomycin (supplied by Lonza) at 37° C., 5% CO$_2$. Pre-adipocytes were differentiated by the addition of insulin, dexamethasone, indomethacin and isobutyl-methylxanthine (supplied by Lonza) to the Preadipocyte Growth Medium-2. Cells were exposed to the differentiating factors for 7 days, at which point the cells were differentiated and ready for the assay. One day before running the assay, the differentiated omental adipocytes were transferred into serum- and phenol-red-free medium for overnight incubation. The assay was performed in a total volume of 200 μL. The cells were pre-incubated with serum-free, phenol-red-free medium containing 0.1% (v/v) of DMSO and various concentrations of the test compounds at least 1 h before [$^3$H] cortisone in ethanol (50 Ci/mmol, ARC, Inc.) was added to achieve a final concentration of cortisone of 100 nM. The cells were incubated for 3-4 hrs at 37° C., 5% CO$_2$. Negative controls were incubated without radioactive substrate and received the same amount of [$^3$H] cortisone at the end of the incubation. Formation of [$^3$H] cortisol was monitored by analyzing 25 μL of each supernatant in a scintillation proximity assay (SPA). (Solly, K.; Mundt, S. S.; Zokian, H. J.; Ding, G. J.; Hermanowski-Vosatka, A.; Strulovici, B.; Zheng, W. Assay Drug Dev. Technol. 2005, 3, 377-384). Many compounds of the invention showed significant activity in this assay.

TABLE OF BIOLOGICAL ASSAY RESULTS

Biological Test Example 1

| Compound | IC$_{50}$ Range[a] | Average % inhibition at 100 nM | Average % inhibition at 111.1 nM |
|---|---|---|---|
| Example 1 | + | | 49.4 |
| Example 2 Isomer 1 | nt | | |
| Example 2 Isomer 2 | ++ | 69.5 | |
| Example 3 Isomer 1 | ++ | 51.2 | |
| Example 3 Isomer 2 | ++ | 60.5 | |
| Example 4 Isomer 1 | nt | | |
| Example 4 Isomer 2 | nt | | |
| Example 5 Isomer 1 | nt | | |
| Example 5 Isomer 2 | nt | | |
| Example 6 Isomer 1 | ++ | 97.2 | |
| Example 6 Isomer 2 | ++ | 47.7 | |
| Example 7 Isomer 1 | ++ | 94.8 | |
| Example 7 Isomer 2 | ++ | 71.0 | |
| Example 8 Isomer 1 | ++ | 96.3 | |
| Example 8 Isomer 2 | ++ | 94.8 | |
| Example 9 Isomer 1 | ++ | 94.5 | |
| Example 9 Isomer 2 | ++ | 93.5 | |
| Example 9 Isomer 3 | ++ | 38.5 | |
| Example 9 Isomer 4 | # | 16.5 | |
| Example 10 Isomer 1 | ++ | 101.8 | |
| Example 10 Isomer 2 | ++ | 54.2 | |
| Example 11 Isomer 1 | ++ | 64.4 | |
| Example 11 Isomer 2 | # | 26.1 | |
| Example 12 | ++ | 96.9 | |
| Example 13 | ++ | 96.1 | |
| Example 14 Isomer 1 | ++ | 95.5 | |
| Example 14 Isomer 2 | ++ | 58.0 | |
| Example 15 | ++ | 96.1 | |
| Example 16 | ++ | 96.1 | |
| Example 17 | ++ | 94.3 | |
| Example 18 | ++ | 97.5 | |
| Example 19 | ++ | 96.0 | |
| Example 20 | ++ | 94.4 | |
| Example 21 | ++ | 93.9 | |
| Example 22 | # | 30.0 | |
| Example 23 | ++ | 95.8 | |
| Example 24 | | | |

[a] ++ means IC$_{50}$ = <100 nM, + means IC$_{50}$ = 100-1000 nM, # means IC$_{50}$ > 100 nM, nt means not tested.

PROPHETIC COMPOUNDS

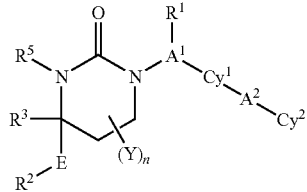

I

| No. | A$^1$ | R$^1$ | Cy$^1$ | A$^2$ | Cy$^2$ | n | E | R$^2$ | R$^3$ | R$^5$ |
|---|---|---|---|---|---|---|---|---|---|---|
| 1 | CH | Me | p-C$_6$H$_4$ | bond | 2,4-diF-Ph | 0 | bond | Ph | NC(CH$_2$)— | H |
| 2 | CH | Me | p-C$_6$H$_4$ | bond | 4-F-Ph | 0 | bond | Ph | MeSO$_2$NH(CH$_2$)$_3$— | H |
| 3 | CH | Me | 4-MeO-Ph | bond | H | 0 | bond | 4-F-Ph | HO(CH$_2$)$_2$— | H |
| 4 | CH | Me | p-C$_6$H$_4$ | bond | 2,4-diMe-5-thiazolyl | 0 | bond | 4-F-Ph | allyl | H |
| 5 | CH | Et | 4-Br-Ph | bond | H | 0 | bond | 4-F-Ph | 2,3-di-HO-propyl | H |
| 6 | CH | Me | p-C$_6$H$_4$ | bond | 4-F-Ph | 0 | bond | 2-F-Ph | HO(CH$_2$)$_3$— | H |
| 7 | CH | Me | p-C$_6$H$_4$ | bond | 4-F-Ph | 0 | bond | 3-F-Ph | HO(CH$_2$)$_3$— | H |
| 8 | CH | Me | p-C$_6$H$_4$ | bond | 4-F-Ph | 0 | bond | Ph | 2-HO-propyl | Me |
| 9 | CH | Me | p-C$_6$H$_4$ | bond | 3-pyridyl | 0 | bond | Ph | HO(CH$_2$)$_2$— | Me |
| 10 | CH | Me | p-C$_6$H$_4$ | bond | 4-F-Ph | 0 | bond | Ph | 2-HO-2-Me-propyl | Me |
| 11 | CH | Me | p-C$_6$H$_4$ | bond | 5-acetyl-2-thienyl | 0 | bond | 3-F-Ph | HO(CH$_2$)$_3$— | H |
| 12 | CH | Me | 4-Cl-Ph | bond | H | 0 | bond | i-Pr | 2,3-di-HO-propyl | H |
| 13 | CH | Et | 4-Br-Ph | bond | H | 0 | bond | 4-F-Ph | H$_2$NCO(CH$_2$)$_2$— | H |
| 14 | CH | Me | p-C$_6$H$_4$ | bond | (5-yl-pyridin-2(1H)-one) | 0 | bond | Ph | HO(CH$_2$)$_3$— | H |
| 15 | CH | Me | p-C$_6$H$_4$ | bond | 4-pyridyl | 0 | bond | Ph | HO(CH$_2$)$_3$— | H |
| 16 | CH | Et | p-C$_6$H$_4$ | bond | 2,4-diF-Ph | 0 | bond | 4-F-Ph | HO(CH$_2$)$_3$— | H |
| 17 | CH | Me | p-C$_6$H$_4$ | bond | 2,4-diF-Ph | 0 | bond | 4-F-Ph | HO(CH$_2$)$_2$O(CH$_2$)$_2$— | H |
| 18 | CH | Me | p-C$_6$H$_4$ | bond | 2,4-diF-Ph | 0 | bond | 2-thienyl | HO(CH$_2$)$_2$— | Me |
| 19 | CH | Me | p-C$_6$H$_4$ | bond | 2,4-diF-Ph | 0 | bond | Ph | MeSO$_2$NH(CH$_2$)$_2$ | H |
| 20 | CH | Me | p-C$_6$H$_4$ | bond | 2,4-diF-Ph | 0 | bond | Ph | H$_2$NCONH(CH$_2$)$_2$ | H |
| 21 | CH | Me | p-C$_6$H$_4$ | bond | 2,4-diF-Ph | 0 | bond | Ph | 2-(1-imidazolyl)ethyl | Me |
| 22 | CH | Me | p-C$_6$H$_4$ | bond | 4-F-Ph | 0 | bond | Ph | H$_2$NCO(CH$_2$)$_2$— | H |
| 23 | CH | Me | p-C$_6$H$_4$ | bond | 2,4-diF-Ph | 0 | bond | 4-F-Ph | H$_2$NCONH(CH$_2$)$_3$ | Me |
| 24 | CH | Me | p-C$_6$H$_4$ | bond | 2,4-diF-Ph | 0 | bond | 4-F-Ph | H$_2$NCOO(CH$_2$)$_2$ | Me |
| 25 | CH | Et | 4-MeO$_2$C-Ph | bond | H | 0 | bond | 4-F-Ph | HO(CH$_2$)$_3$— | H |

-continued

PROPHETIC COMPOUNDS

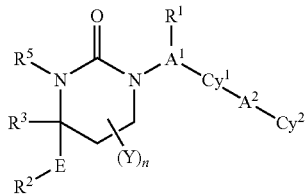

I

| No. | A¹ | R¹ | Cy¹ | A² | Cy² | n | E | R² | R³ | R⁵ |
|---|---|---|---|---|---|---|---|---|---|---|
| 26 | CH | Me | p-C₆H₄ | bond | 2,4-diF-Ph | 0 | bond | 4-F-Ph | MeO(CH₂)₂— | Me |
| 27 | CH | Me | cyclohexyl | bond | H | 0 | bond | 4-F-Ph | HO(CH₂)₃— | H |
| 28 | CH | Me | p-C₆H₄ | bond | 2,4-diF-Ph | 0 | bond | 4-F-Ph | MeCOCH₂— | Me |
| 29 | CH | Me | p-C₆H₄ | bond | cyclopropyl | 0 | bond | 4-F-Ph | allyl | H |
| 30 | bond | | pyridine-2,6-diyl | bond | 2,4-diF-Ph | 0 | bond | 2-F-Ph | HO(CH₂)₂— | H |
| 31 | bond | | Ph | bond | 2,6-diCl-Ph | 0 | bond | Ph | HO(CH₂)₂— | Me |
| 32 | bond | | 4-F-phenylene | bond | 2,4-diF-Ph | 0 | bond | 2-F-Ph | HO(CH₂)₂— | H |
| 33 | CH | Me | p-C₆H₄ | bond | 4-F-Ph | 0 | bond | Ph | H₂NSO₂OCH₂CH₂— | H |
| 34 | CH | Me | p-C₆H₄ | bond | 4-FPh | 0 | bond | 4-F-Ph | H₂NSO₂NHCH₂CH₂— | H |
| 35 | CH | Me | p-C₆H₄ | bond | 2,4-diF-Ph | 0 | bond | Ph | MeC(=O)NHCH₂CH₂— | H |
| 36 | CH | Me | p-C₆H₄ | bond | 4-F-Ph | 0 | bond | Ph | H₂NCOCH₂CH₂ | H |
| 37 | CH | Me | p-C₆H₄ | bond | 4-(aminomethyl)phenyl | 0 | bond | 4-F-Ph | H₂NCOCH₂CH₂ | H |
| 38 | CH | Me | cyclohexyl | bond | H | 0 | bond | 2-F-Ph | H₂NCOCH₂CH₂ | H |
| 39 | CH | Me | p-C₆H₄ | bond | 5-(1-aminoethyl)thiophen-2-yl | 0 | bond | 3-F-Ph | H₂NCOCH₂CH₂ | H |
| 40 | CH | Me | p-C₆H₄ | bond | 5-(1-aminoethyl)thiophen-2-yl | 0 | bond | 4-F-Ph | MeSO₂NH(CH₂)₃ | H |
| 41 | CH | Me | p-C₆H₄ | bond | 4-(aminomethyl)phenyl | 0 | bond | Ph | MeSO₂NH(CH₂)₃ | H |
| 42 | CH | Me | cyclohexyl | bond | H | 0 | bond | 4-F-Ph | MeSO₂NH(CH₂)₃ | H |

PROPHETIC COMPOUNDS

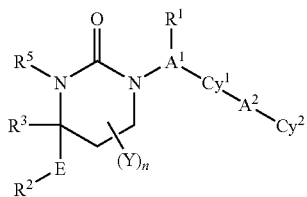

I

| No. | A¹ | R¹ | Cy¹ | A² | Cy² | n | E | R² | R³ | R⁵ |
|---|---|---|---|---|---|---|---|---|---|---|
| 43 | CH | Me | p-$C_6H_4$ | bond | 4-F-Ph | 0 | bond | i-Pr | $MeSO_2NH(CH_2)_3$ | H |
| 44 | CH | Me | p-$C_6H_4$ | bond | 4-F-Ph | 0 | bond | 3-pyridyl | $MeSO_2NH(CH_2)_3$ | H |
| 45 | CH | Me | p-$C_6H_4$ | bond | 4-F-Ph | 0 | bond | Ph | morpholinopropyl | H |
| 46 | CH | Me | p-$C_6H_4$ | bond | 4-F-Ph | 0 | $CH_2$ | i-Pr | morpholinopropyl | H |
| 47 | CH | Me | p-$C_6H_4$ | bond | 2,4-di-F-Ph | 0 | bond | cyclohexyl | morpholinopropyl | H |
| 48 | bond |  | 2,6-pyridyl | bond | 4-F-Ph | 0 | bond | 4-F-Ph | morpholinopropyl | H |
| 49 | CH | Me | p-$C_6H_4$ | bond | 2-(4-aminomethyl)thiazolyl | 0 | bond | Ph | $HO(CH_2)_3$— | H |
| 50 | CH | Me | p-$C_6H_4$ | bond | 2-(5-carbamoyl)thiazolyl | 0 | bond | 4-F-Ph | $H_2NCOCH_2CH_2$ | H |

The compounds of the invention are useful for ameliorating or treating disorders or diseases in which decreasing the level of cortisol is effective in treating a disease state. Thus, the compounds of the invention can be used in the treatment or prevention of diabetes mellitus, obesity, symptoms of metabolic syndrome, glucose intolerance, hyperglycemica, hypertension, hyperlipidemia, insulin resistance, cardiovascular disease, dyslipidemia, atherosclerosis, lipodystrophy, osteoporosis, glaucoma, Cushing's syndrome, Addison's Disease, visceral fat obesity associated with glucocorticoid therapy, depression, anxiety, Alzheimer's disease, dementia, cognitive decline (including age-related cognitive decline), polycystic ovarian syndrome, infertility and hypergonadism. The compounds of the invention can be used as therapeutic agents for pseudo Cushing's Syndrome associated with alcoholic liver disease. In addition, the compounds modulate the function of B and T cells of the immune system and can therefore be used to treat diseases such as tuberculosis, leprosy and psoriasis. They can also be used to promote wound healing, particularly in diabetic patients.

Additional diseases or disorders that are related to 11β-HSD1 activity include those selected from the group consisting of lipid disorders, hypretriglyceridemia, hypercholesterolemia, low HDL levels, high LDL levels, vascular restenosis, pancreatitis, abdominal obesity, neurodegenerative disease, retinopathy, nephropathy, neuropathy, diabetes, coronary heart disease, stroke, peripheral vascular disease, Cushing's syndrome, hyperinsulinemia, viral diseases, and Syndrome X. A further disease related to 11β-HSD1 activity is pseudo Cushing's Syndrome associated with alcoholic liver disease.

A pharmaceutical composition of the invention may, alternatively or in addition to a compound of Formula I, comprise a pharmaceutically acceptable salt of a compound of Formula I or a prodrug or pharmaceutically active metabolite of such a compound or salt and one or more pharmaceutically acceptable carriers therefore. Alternatively, a pharmaceutical composition of the invention may comprise a compound of Formula I, Ia-s$^2$ or a pharmaceutical salt thereof as the only pharmaceutically active agent in the pharmaceutical composition. The disclosed 11β-HSD1 inhibitors can be used alone or in a combination therapy with one or more additional agents for the treatment of diabetes, dyslipidemia, cardiovascular disease, hypertension, obesity, cancer or glaucoma.

The compositions of the invention are 11β-HSD1 inhibitors. Said compositions contain compounds having a mean inhibition constant ($IC_{50}$) against 11β-HSD1 of below about 1,000 nM; preferably below about 100 nM; more preferably below about 50 nM; even more preferably below about 5 nM; and most preferably below about 1 nM.

The invention includes a therapeutic method for treating or ameliorating an 11β-HSD1 mediated disorder in a subject in need thereof comprising administering to a subject in need thereof an effective amount of a compound of Formula I, or an enantiomer, diastereomer, or pharmaceutically acceptable salt thereof of composition thereof. As used herein, "treating" or "treatment" includes both therapeutic and prophylactic treatment. Therapeutic treatment includes reducing the symptoms associated with a disease or condition and/or increasing the longevity of a subject with the disease or condition. Prophylactic treatment includes delaying the onset of a disease or condition in a subject at risk of developing the disease or condition or reducing the likelihood that a subject will then develop the disease or condition in a subject that is at risk for developing the disease or condition.

An embodiment of the invention includes administering an 11β-HSD1 inhibiting compound of Formula I or composition thereof in a combination therapy with one or more additional agents for the treatment of diabetes, dyslipidemia, cardiovascular disease, hypertension, obesity, cancer or glaucoma. Agents for the treatment of diabetes include insulins, such as Humulin® (Eli Lilly), Lantus® (Sanofi Aventis), Novolin (Novo Nordisk), and Exubera® (Pfizer); PPAR gamma agonists, such as Avandia® (rosiglitzone maleate, GSK) and Actos® (pioglitazone hydrochloride, Takeda/Eli Lilly); sulfonylureas, such as Amaryl® (glimepiride, Sanofi Aventis), Diabeta® (glyburide, Sanofi Aventis), Micronase®/Glynase® (glyburide, Pfizer), and Glucotrol®/Glucotrol XL® and (glipizide, Pfizer); meglitinides, such as Prandin®/NovoNorm® (repaglinide, Novo Nordisk), Starlix® (nateglinide, Novartis), and Glufast® (mitiglinide, Takeda); biguanides, such as Glucophase®/Glucophase XR® (metformin HCl, Bristol Myers Squibb) and Glumetza (metformin HCl, Depomed); thiazolidinediones; amylin analogs, GLP-1 analogs; DPP-IV inhibitors; PTB-1B inhibitors; protein kinase inhibitors (including AMP-activated protein kinase inhibitors); glucagon antagonists, glycogen synthase kinase-3 beta inhibitors; glucose-6-phosphatase inhibitors; glycogen phosphorylase inhibitors; sodium glucose co-transporter inhibitors, and alpha-glucosidase inhibitors, such as Precose®/Glucobay®/Prandasee/Glucor® (acarbose, Bayer) and Glyset® (miglitol, Pfizer). Agents for the treatment of dyslipidemia and cardiovascular disease include statins, fibrates, and ezetimbe. Agents for the treatment of hypertension include alpha-blockers, beta-blockers, calcium channel blockers, diuretics, angiotensin converting enzyme (ACE) inhibitors, dual ACE and neutral endopeptidase (NEP) inhibitors, angiotensin-receptor blockers (ARBs), aldosterone synthase inhibitor, aldosterone-receptor antagonists, or endothelin receptor antagonist. Agents for the treatment of obesity include orlistat, phentermine, sibutramine and rimonabant.

An embodiment of the invention includes administering an 11β-HSD1 inhibiting compound of Formula I or composition thereof in a combination therapy with one or more other 11β-HSD1 inhibitors (whether such inhibitors are also compounds of Formula I or are compounds of a different class/genus), or with combination products, such as Avandamet® (metformin HCl and rosiglitazone maleate, GSK); Avandaryl® (glimepiride and rosiglitazone maleate, GSK); Metaglip® (glipizide and metformin HCl, Bristol Myers Squibb); and Glucovance® (glyburide and metformin HCl, Bristol Myers Squibb).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Additionally, the compounds of the present invention can be administered intranasally or transdermally. It will be obvious to those skilled in the art that the following dosage forms may comprise as the active ingredient, either compounds or a corresponding pharmaceutically acceptable salt of a compound of the present invention.

For preparing pharmaceutical compositions from the compounds of the present invention, pharmaceutically acceptable carriers can either be solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium caboxymethylcellulose, a low-melting wax, cocoa butter, and the like. Tablets, powders, cachets, lozenges, fast-melt strips, capsules and pills can be used as solid dosage forms containing the active ingredient suitable for oral administration.

For preparing suppositories, a low-melting wax, such as a mixture of fatty acid glycerides or cocoa butter, is first-melted and the active ingredient is dispersed homogeneously therein, as by stirring. The molten homogeneous mixture is then poured into convenient sized molds, allowed to cool, and thereby to solidify.

Liquid form preparations include solutions, suspensions, retention enemas, and emulsions, for example, water or water propylene glycol solutions. For parenteral injection, liquid preparations can be formulated in solution in aqueous polyethylene glycol solution.

Aqueous solutions suitable for oral administration can be prepared by dissolving the active ingredient in water and adding suitable colorants, flavors, stabilizing, and thickening agents as desired. Aqueous suspensions for oral administration can be prepared by dispersing the finely divided active ingredient in water with viscous material, such as natural or synthetic gums, resins, methylcellulose, sodium carboxymethylcellulose, and other well-known suspending agents.

The pharmaceutical composition is preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules. Also, the unit dosage form can be a tablet, cachet, capsule, or lozenge itself, or it can be the appropriate amount of any of these in packaged form.

The quantity of active ingredient in a unit dose preparation may be varied or adjusted from about 0.1 mg to about 1000.0 mg, preferably from about 0.1 mg to about 100 mg. The dosages, however, may be varied depending upon the requirements of the patient, the severity of the condition being treated, and the compound being employed. Determination of the proper dosage for a particular situation is within the skill in the art. Also, the pharmaceutical composition may contain, if desired, other compatible therapeutic agents.

In therapeutic treatment or as a method-of-use as an inhibitor of 11β-HSD1 or an inhibitor in the production of cortisol in the cell, the active ingredient is preferably administered orally in a solid dosage form as disclosed above in an amount of about 0.1 mg to about 100 mg per daily dose where the dose is administered once or more than once daily.

All publications, patents and patent applications mentioned in this specification are herein incorporated by reference to the same extent as if each individual publication or patent application were specifically and individually designated as having been incorporated by reference. It is understood that the examples and embodiments described herein are for illustrative purposes only, and it will be appreciated that the invention is susceptible to modification, variation and change without departing from the proper scope or fair meaning of the appended claims.

What is claimed is:
1. A compound of Formula (Ia) or (Ik):

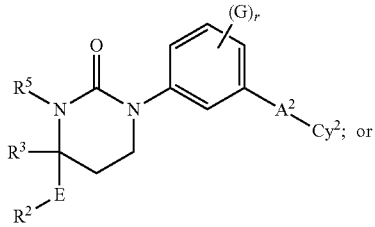

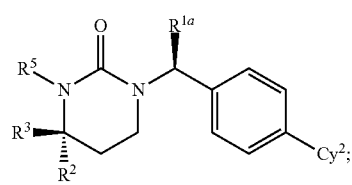

wherein:
$R^{1a}$ is methyl or ethyl;
G is independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylamino-carbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxyl and $(C_1-C_6)$alkylcarbonyl;
r is 0, 1, 2, 3 or 4;
$A^2$ is (a) a bond, O, S or $NR^4$; or (b) $(C_1-C_3)$alkylene or $(C_1-C_2)$alkyleneoxy, each of which is optionally substituted with 1 to 4 groups independently selected from methyl, ethyl, trifluoromethyl and oxo;
$Cy^2$ is (a) hydrogen or (b) aryl, heteroaryl, cycloalkyl or heterocyclyl, each of which is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1$-

$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;

E is (a) a bond or (b) ($C_1$-$C_3$)alkylene or ($C_1$-$C_2$)alkylenyloxy, wherein the O is attached to $R^2$, each of which is optionally substituted with 1 to 4 groups independently selected from methyl, ethyl, trifluoromethyl and oxo;

$R^2$ is ($C_1$-$C_6$)alkyl, aryl, heteroaryl, cycloalkyl or heterocyclyl, each of which is optionally substituted with up to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;

$R^3$ is selected from ($C_1$-$C_6$)alkyl, ($C_2$-$C_6$)alkenyl, ($C_2$-$C_6$)alkynyl, ($C_3$-$C_5$)cycloalkyl($C_1$-$C_4$)alkyl, ($C_1$-$C_3$)alkoxy($C_1$-$C_3$)alkoxy, and ($C_1$-$C_3$)alkoxy($C_1$-$C_3$)alkyl, each of which is optionally substituted with up to four groups independently selected from fluorine, cyano, oxo, $R^4$, $R^4O-$, $(R^4)_2N-$, $R^4O_2C-$, $R^4S$, $R^4S(=O)-$, $R^4S(=O)_2-$, $R^4C(=O)NR^4-$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4-$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4-$, $R^4S(=O)_2NR^4-$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4OS(=O)_2NHC(=O)O-$, $R^4OS(=O)_2NHC(=O)NR^4-$, $(R^4)_2NS(=O)_2NHC(=O)-$, $(R^4)_2NS(=O)_2NHC(=O)O-$, $(R^4)_2NS(=O)_2NHC(=O)NR^4-$, $R^4C(=O)NHS(=O)_2-$, $R^4C(=O)NHS(=O)_2O-$, $R^4C(=O)NHS(=O)_2NR^4-$, $R^4OC(=O)NHS(=O)_2-$, $R^4OC(=O)NHS(=O)_2O-$, $R^4OC(=O)NHS(=O)_2NR^4-$, $(R^4)_2NC(=O)NHS(=O)_2-$, $(R^4)_2NC(=O)NHS(=O)_2O-$, $(R^4)_2NC(=O)NHS(=O)_2NR^4-$, spirocycloalkyl, heterocyclyl (which in turn may be optionally substituted with alkyl, haloalkyl, halogen or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), aryl-amino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido or N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

$R^4$ is independently selected from H, ($C_1$-$C_6$)alkyl, halo($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$)alkyl and ($C_1$-$C_6$)alkoxy($C_1$-$C_6$)alkyl; and $R^5$ is H, ($C_1$-$C_6$)alkyl, halo($C_1$-$C_6$)alkyl, or hydroxy($C_1$-$C_6$)alkyl;

or a pharmaceutically acceptable salt, enantiomer or diastereomer thereof.

2. The compound of claim 1, wherein the compound is selected from the group consisting of:

4-methyl-4-phenyl-1-m-tolyltetrahydropyrimidin-2(1H)-one;

4-allyl-1-(1-(2',4'-difluorobiphenyl-4-yl)ethyl)-4-(4-fluorophenyl)tetrahydropyrimidin-2(1H)-one;

4-allyl-1-(1-(4'-fluorobiphenyl-4-yl)ethyl)-4-(4-fluorophenyl)tetrahydropyrimidin-2(1H)-one;

1-(1-(2',4'-difluorobiphenyl-4-yl)ethyl)-4-(4-fluorophenyl)-4-(2-hydroxyethyl)tetrahydropyrimidin-2(1H)-one;
1-(1-(2',4'-difluorobiphenyl-4-yl)ethyl)-4-(4-fluorophenyl)-4-(3-hydroxypropyl)tetrahydropyrimidin-2(1H)-one;
1-(1-(2',4'-difluorobiphenyl-4-yl)ethyl)-4-(2,3-dihydroxypropyl)-4-(4-fluorophenyl)tetrahydropyrimidin-2(1H)-one;
4-(2,3-dihydroxypropyl)-1-(1-(4'-fluorobiphenyl-4-yl)ethyl)-4-(4-fluorophenyl)tetrahydropyrimidin-2(1H)-one;
1-(1-(4'-fluorobiphenyl-4-yl)ethyl)-4-(4-fluorophenyl)-4-(3-hydroxypropyl)tetrahydropyrimidin-2(1H)-one;
1-(1-(4'-fluorobiphenyl-4-yl)ethyl)-4-(3-hydroxypropyl)-4-phenyltetrahydropyrimidin-2(1H)-one;
2-(1-(1-(2',4'-difluorobiphenyl-4-yl)ethyl)-2-oxo-4-phenylhexahydropyrimidin-4-yl)acetonitrile;
N-(3-(1-(1-(4'-fluorobiphenyl-4-yl)ethyl)-2-oxo-4-phenylhexahydropyrimidin-4-yl)propyl)methanesulfonamide;
4-allyl-1-(1-(4-(2,4-dimethylthiazol-5-yl)phenyl)ethyl)-4-(4-fluorophenyl)tetrahydropyrimidin-2(1H)-one;
1-(4'-fluorobiphenyl-4-yl)ethyl)-4-(2-fluorophenyl)-4-(3-hydroxypropyl)tetrahydropyrimidin-2(1H)-one;
1-(1-(4'-fluorobiphenyl-4-yl)ethyl)-4-(3-fluorophenyl)-4-(3-hydroxypropyl)tetrahydropyrimidin-2(1H)-one;
1-(1-(4'-fluorobiphenyl-4-yl)ethyl)-4-(2-hydroxypropyl)-3-methyl-4-phenyltetrahydropyrimidin-2(1H)-one;
4-(2-hydroxyethyl)-3-methyl-4-phenyl-1-(1-(4-(pyridin-3-yl)phenyl)ethyl)tetrahydropyrimidin-2(1H)-one;
1-(1-(4'-fluorobiphenyl-4-yl)ethyl)-4-(2-hydroxy-2-methylpropyl)-3-methyl-4-phenyltetrahydropyrimidin-2(1H)-one;
1-(1-(4-(5-acetylthiophen-2-yl)phenyl)ethyl)-4-(3-fluorophenyl)-4-(3-hydroxypropyl)tetrahydropyrimidin-2(1H)-one;
4-(3-hydroxypropyl)-1-(1-(4-(6-oxo-1,6-dihydropyridin-3-yl)phenyl)ethyl)-4-phenyltetrahydropyrimidin-2(1H)-one;
4-(3-hydroxypropyl)-4-phenyl-1-(1-(4-(pyridin-4-yl)phenyl)ethyl)tetrahydropyrimidin-2(1H)-one;
1-(1-(2',4'-difluorobiphenyl-4-yl)propyl)-4-(4-fluorophenyl)-4-(3-hydroxypropyl)tetrahydropyrimidin-2(1H)-one;
1-(1-(2',4'-difluorobiphenyl-4-yl)ethyl)-4-(4-fluorophenyl)-4-(2-(2-hydroxyethoxy)ethyl)tetrahydropyrimidin-2(1H)-one;
1-(1-(2',4'-difluorobiphenyl-4-yl)ethyl)-4-(2-hydroxyethyl)-3-methyl-4-(thiophen-2-yl)tetrahydropyrimidin-2(1H)-one;
N-(2-(1-(1-(2',4'-difluorobiphenyl-4-yl)ethyl)-2-oxo-4-phenylhexahydropyrimidin-4-yl)ethyl)methanesulfonamide;
1-(2-(1-(1-(2',4'-difluorobiphenyl-4-yl)ethyl)-2-oxo-4-phenylhexahydropyrimidin-4-yl)ethyl)urea;
4-(2-(1H-imidazol-1-yl)ethyl)-1-(1-(2',4'-difluorobiphenyl-4-yl)ethyl)-3-methyl-4-phenyltetrahydropyrimidin-2(1H)-one;
3-(1-(1-(4'-fluorobiphenyl-4-yl)ethyl)-2-oxo-4-phenylhexahydropyrimidin-4-yl)propanamide;
1-(3-(1-(1-(2',4'-difluorobiphenyl-4-yl)ethyl)-4-(4-fluorophenyl)-3-methyl-2-oxohexahydropyrimidin-4-yl)propyl)urea;
2-(1-(1-(2',4'-difluorobiphenyl-4-yl)ethyl)-4-(4-fluorophenyl)-3-methyl-2-oxohexahydropyrimidin-4-yl)ethyl carbamate;
1-(1-(2',4'-difluorobiphenyl-4-yl)ethyl)-4-(4-fluorophenyl)-4-(2-methoxyethyl)-3-methyltetrahydropyrimidin-2(1H)-one;
1-(1-(2',4'-difluorobiphenyl-4-yl)ethyl)-4-(4-fluorophenyl)-3-methyl-4-(2-oxopropyl)tetrahydropyrimidin-2(1H)-one;
4-allyl-1-(1-(4-cyclopropylphenyl)ethyl)-4-(4-fluorophenyl)tetrahydropyrimidin-2(1H)-one;
1-(2',6'-dichlorobiphenyl-3-yl)-4-(2-hydroxyethyl)-3-methyl-4-phenyltetrahydropyrimidin-2(1H)-one;
4-(2-fluorophenyl)-4-(2-hydroxyethyl)-1-(2',4',6-trifluorobiphenyl-3-yl)tetrahydropyrimidin-2(1H)-one;
2-(1-(1-(4'-fluorobiphenyl-4-yl)ethyl)-2-oxo-4-phenylhexahydropyrimidin-4-yl)ethyl sulfamate;
4-(2-(aminosulfonylamino)ethyl)-1-(1-(4'-fluorobiphenyl-4-yl)ethyl)-4-(4-fluorophenyl)tetrahydropyrimidin-2(1H)-one;
N-(2-(1-(1-(2',4'-difluorobiphenyl-4-yl)ethyl)-2-oxo-4-phenylhexahydropyrimidin-4-yl)ethyl)acetamide;
3-(1-(1-(4'-fluorobiphenyl-4-yl)ethyl)-2-oxo-4-phenylhexahydropyrimidin-4-yl)propanamide;
3-(1-(1-(4'-(aminomethyl)biphenyl-4-yl)ethyl)-4-(4-fluorophenyl)-2-oxohexahydropyrimidin-4-yl)propanamide;
3-(1-(1-(4-(5-(1-aminoethyl)thiophen-2-yl)phenyl)ethyl)-4-(3-fluorophenyl)-2-oxohexahydropyrimidin-4-yl)propanamide;
N-(3-(1-(1-(4-(5-(1-aminoethyl)thiophen-2-yl)phenyl)ethyl)-4-(4-fluorophenyl)-2-oxohexahydropyrimidin-4-yl)propyl)methanesulfonamide;
N-(3-(1-(1-(4'-(aminomethyl)biphenyl-4-yl)ethyl)-2-oxo-4-phenylhexahydropyrimidin-4-yl)propyl)methanesulfonamide;
N-(3-(1-(1-(4'-fluorobiphenyl-4-yl)ethyl)-4-isopropyl-2-oxohexahydropyrimidin-4-yl)propyl)methanesulfonamide;
N-(3-(1-(1-(4'-fluorobiphenyl-4-yl)ethyl)-2-oxo-4-(pyridin-3-yl)hexahydropyrimidin-4-yl)propyl)methanesulfonamide;
1-(1-(4'-fluorobiphenyl-4-yl)ethyl)-4-(2-morpholinoethyl)-4-phenyltetrahydropyrimidin-2(1H)-one;
1-(1-(4'-fluorobiphenyl-4-yl)ethyl)-4-isopropyl-4-(2-morpholinoethyl)tetrahydropyrimidin-2(1H)-one;
4-cyclohexyl-1-(1-(2',4'-difluorobiphenyl-4-yl)ethyl)-4-(2-morpholinoethyl)tetrahydropyrimidin-2(1H)-one;
1-(1-(4-(5-(aminomethyl)thiazol-2-yl)phenyl)ethyl)-4-(3-hydroxypropyl)-4-phenyltetrahydropyrimidin-2(1H)-one;
2-(4-(1-(4-(3-amino-3-oxopropyl)-4-(4-fluorophenyl)-2-oxotetrahydropyrimidin-1(2H)-yl)ethyl)phenyl)thiazole-5-carboxamide; and
4-(2-hydroxy-2-methylpropyl)-1-(1-(4-(1-methyl-2-oxo-1,2-dihydropyridin-4-yl)phenyl)ethyl)-4-phenyltetrahydropyrimidin-2(1H)-one;
or a pharmaceutically acceptable salt, diastereomer or enantiomer of any of the foregoing.

3. A method of treating a subject with a disease or disorder selected from diabetes mellitus, obesity, glucose intolerance, hyperglycemia, hypertension, insulin resistance, dyslipidemia, atherosclerosis, Cushing's syndrome, visceral fat obesity associated with glucocorticoid therapy, Alzheimer's disease, cognitive decline, or metabolic syndrome, comprising the step of administering to the subject an effective amount of a compound of claim 1, or a pharmaceutically acceptable salt, enantiomer or diastereomer thereof.

4. A pharmaceutical composition comprising: i) a pharmaceutically acceptable carrier or diluent; and ii) the compound of claim 1; or a pharmaceutically acceptable salt, enantiomer or diastereomer thereof.

5. (S)-4-(2-hydroxy-2-methylpropyl)-1-((S)-1-(4-(1-methyl-2-oxo-1,2-dihydropyridin-4-yl)phenyl)ethyl)-4-phenyltetrahydropyrimidin-2(1H)-one; or a pharmaceutically acceptable salt thereof.

6. A pharmaceutical composition comprising: i) a pharmaceutically acceptable carrier or diluent; and ii) (S)-4-(2-hydroxy-2-methylpropyl)-1-((S)-1-(4-(1-methyl-2-oxo-1,2-dihydropyridin-4-yl)phenyl)ethyl)-4-phenyltetrahydropyrimidin-2(1H)-one; or a pharmaceutically acceptable salt thereof.

7. A method of treating a subject with a disease or disorder selected from diabetes mellitus, obesity, glucose intolerance, hyperglycemia, hypertension, insulin resistance, dyslipidemia, atherosclerosis, Cushing's syndrome, visceral fat obesity associated with glucocorticoid therapy, Alzheimer's disease, cognitive decline, or metabolic syndrome, comprising the step of administering to the subject an effective amount of (S)-4-(2-hydroxy-2-methylpropyl)-1-((S)-1-(4-(1-methyl-2-oxo-1,2-dihydropyridin-4-yl)phenyl)ethyl)-4-phenyltetrahydropyrimidin-2(1H)-one, or a pharmaceutically acceptable salt, enantiomer or diastereomer thereof.

8. The compound of claim 1, wherein $R^3$ is selected from $(C_1-C_6)$alkyl, $(C_2-C_6)$alkenyl, $(C_2-C_6)$alkynyl, and $(C_1-C_3)$alkoxy$(C_1-C_3)$alkyl, each of which being substituted with one to four groups independently selected from cyano, oxo, $R^4O-$, $(R^4)_2N-$, $R^4O_2C-$, $R^4S$, $R^4S(=O)-$, $R^4S(=O)_2-$, $R^4C(=O)NR^4-$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4-$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4-$, $R^4S(=O)_2NR^4-$, $R^4SO_2NR^4-$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4OS(=O)_2NHC(=O)O-$, $R^4OS(=O)_2NHC(=O)NR^4-$, $(R^4)_2NS(=O)_2NHC(=O)-$, $(R^4)_2NS(=O)_2NHC(=O)O-$, $(R^4)_2NS(=O)_2NHC(=O)NR^4-$, $R^4C(=O)NHS(=O)_2-$, $R^4C(=O)NHS(=O)_2O-$, $R^4C(=O)NHS(=O)_2NR^4-$, $R^4OC(=O)NHS(=O)_2-$, $R^4OC(=O)NHS(=O)_2O-$, $R^4OC(=O)NHS(=O)_2NR^4-$, $(R^4)_2NC(=O)NHS(=O)_2-$, $(R^4)_2NC(=O)NHS(=O)_2O-$ and $(R^4)_2NC(=O)NHS(=O)_2NR^4-$.

9. The compound of claim 1, wherein:
$A^2$ is a bond, O, OCH$_2$CO or C=O;
Cy$^2$ is (a) hydrogen or (b) phenyl, thienyl, pyridyl, N-oxopyridyl, cyclopropyl, piperidinyl, piperazinyl, morpholinyl, thiazolyl, oxadiazolyl, thiadiazolyl, pyrazolyl, S,S-dioxothiazinyl, or 2-oxo-1,2-dihydropyridyl, each of which being optionally substituted by 1 to 4 groups independently selected from halo, hydroxy, methoxy, hydroxymethyl, methoxycarbonyl, amino, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylaminosulfonyl, pyrrolidine-1-sulfonyl, methylsulfonylaminomethyl, tetrazolyl, methyl, trifluoromethyl, acetyl, 2-hydroxyethyl and 1-aminoethyl;
$R^2$ is isopropyl, thienyl, phenyl, or pyridyl, each of which being optionally substituted with halo, methyl, methylthio or (4-morpholino)methyl;
$R^3$ is methyl, ethyl, propyl, butyl, vinyl, allyl or ethoxyethyl, each of which being optionally substituted with up to two groups independently selected from HO—, MeO—, H$_2$N—, MeC(=O)NH—, MeS(=O)$_2$NH—, H$_2$NC(=O)—, MeNHC(=O)—, HO$_2$C—, (HO)$_2$P(=O)O—, H$_2$NS(=O)$_2$O—, H$_2$NS(=O)$_2$NH—, MeNHC(=O)NH—, MeNHC(=O)O—, oxo, cyano, HO$_2$C—, HOCH$_2$CH$_2$NH—, 4-morpholino, HOCH$_2$C(=O)NH—, H$_2$NCH$_2$C(=O)NH—, EtNHC(=O)NH, MeOC(=O)NH—, MeNHC(=NCN)NH—, Me-, MeS—, MeSO$_2$-MeSO$_2$N(Me)-, MeS(=O)$_2$NHC(=O)—, imidazolylamino-, imidazolyl, tetrazolyl, H$_2$NCONH—, H$_2$NCO$_2$—, HOCH$_2$CH$_2$O—, MeNH—, Me$_2$N— and MeCONMe; and
$R^5$ is hydrogen or methyl.

10. The compound of claim 1, wherein the compound is of Formula (Ik):

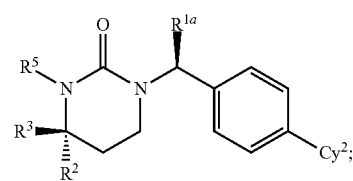

wherein:
$R^2$ is phenyl optionally substituted with up to 2 groups selected from halogen, methyl, trifluoromethyl and cyano;
$R^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl; and
Cy$^2$ is heterocyclyl optionally substituted with up to 3 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, H$_2$NCO, H$_2$NSO$_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, oxo, heteroaryl, amino$(C_1-C_6)$alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxyl and ($C_1$-$C_6$)alkylcarbonyl;

or a pharmaceutically acceptable salt, enantiomer or diastereomer thereof.

11. The compound of claim 1, wherein the compound is of Formula (Ik):

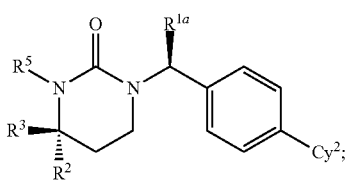

Ik wherein:

$R^{1a}$ is methyl or ethyl;

$R^2$ is phenyl optionally substituted with up to 2 groups selected from halogen, methyl, trifluoromethyl and cyano;

$R^3$ is 2-hydroxy-2-methylpropyl or 2-cyano-2-methylpropyl; and $Cy^2$ is heteroaryl optionally substituted with up 2 groups selected from ($C_1$-$C_4$)alkyl, halo($C_1$-$C_4$)alkyl, halogen, cyano, $CONH_2$, ($C_1$-$C_4$)alkylaminocarbonyl, di($C_1$-$C_4$)alkylaminocarbonyl and ($C_3$-$C_5$)cycloalkylaminocarbonyl;

or a pharmaceutically acceptable salt, enantiomer or diastereomer thereof.

12. A compound of Formulae ($Io^1$) or ($Io^2$):

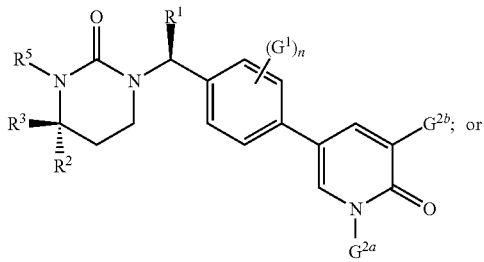

$Io^1$

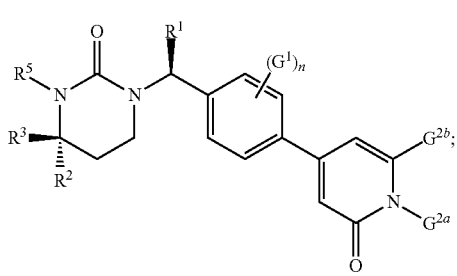

$Io^2$ wherein:

$R^1$ is methyl or ethyl;

$R^2$ is ($C_1$-$C_6$)alkyl, aryl, heteroaryl, cycloalkyl or heterocyclyl, each of which is optionally substituted with up to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_1$-$C_6$)cycloalkyl, ($C_4$-$C_7$)cycloalkylalkyl, ($C_7$-$C_6$)alkenyl, halo($C_7$-$C_6$)alkenyl, hydroxy($C_7$-$C_6$)alkenyl, ($C_7$-$C_6$)alkynyl, ($C_3$-$C_6$)cycloalkyl($C_2$-$C_4$)alkynyl, halo($C_1$-$C_6$)alkyl, halo($C_1$-$C_6$)cycloalkyl, halo($C_4$-$C_7$)cycloalkylalkyl, ($C_1$-$C_6$)alkoxy, ($C_1$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_1$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, $T_1$-$C_6$)alkanesulfinyl, ($C_1$-$C_6$)cycloalkanesulfinyl, ($C_4$-$C_7$)cycloalkylalkanesulfinyl, halo($C_1$-$C_6$)alkanesulfinyl, halo($C_1$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_1$-$C_6$)alkoxy, ($C_1$-$C_6$)alkylamino($C_1$-$C_6$)alkoxy, di($C_1$-$C_6$)alkylamino($C_1$-$C_6$)alkoxy, ($C_1$-$C_6$)alkylcarbonyl, ($C_1$-$C_6$)cycloalkylcarbonyl, ($C_3$-$C_6$)cycloalkylaminocarbonyl, {($C_1$-$C_6$)cycloalkyl}{($C_1$-$C_6$)alkyl}aminocarbonyl, di($C_1$-$C_6$)cycloalkylaminocarbonyl, ($C_1$-$C_6$)cycloalkylaminosulfonyl, {($C_1$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_1$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;

$R^3$ is selected from ($C_1$-$C_6$)alkyl, ($C_2$-$C_6$)alkenyl, ($C_2$-$C_6$)alkynyl, ($C_3$-$C_5$)cycloalkyl($C_1$-$C_4$)alkyl, ($C_1$-$C_3$)alkoxy($C_1$-$C_3$)alkoxy, and ($C_1$-$C_3$)alkoxy($C_1$-$C_3$)alkyl, each of which is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, spirocycloalkyl, heterocyclyl (which in turn may be optionally substituted with alkyl, haloalkyl, halogen or oxo), heteroaryl (which in turn may be optionally substituted with alkyl, haloalkyl, alkoxy, alkylthio, alkylsulfonyl, halogen, trifluoromethyl, dialkylamino, nitro, cyano, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido or N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

$R^4$ is independently selected from H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl;

$R^5$ is H, $(C_1-C_6)$alkyl, halo$(C_1-C_6)$alkyl, or hydroxy$(C_1-C_6)$alkyl;

$G^1$ is $(C_1-C_4)$alkyl, $(C_1-C_4)$alkoxy, $(C_1-C_4)$haloalkyl, $(C_1-C_4)$haloalkoxy, halogen, cyano or nitro;

n is 0, 1 or 2;

$G^2$ is $(C_1-C_4)$alkyl, $(C_3-C_4)$cycloalkyl or $(C_1-C_4)$haloalkyl; and

G is hydrogen, fluorine, chlorine, cyano, hydroxy, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl or $(C_1-C_4)$alkylcarbonylamino; or a pharmaceutically acceptable salt, enantiomer or diastereomer thereof.

13. The compound of claim 12, wherein:

$R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $H_2NC(=O)CMe_2CH_2$, 3-hydroxy-3-methylbutyl, 2-hydroxy-2-methylpropyl or 2-cyano-2-methylpropyl;

or a pharmaceutically acceptable salt, enantiomer or diastereomer thereof.

14. The compound of claim 13, wherein:

$R^2$ is phenyl or fluorophenyl;

$R^3$ is 2-hydroxy-2-methylpropyl or 2-cyano-2-methylpropyl;

the substituent $G^2$ is selected from $(C_1-C_4)$alkyl, $(C_3-C_4)$cycloalkyl, $(C_3-C_4)$cycloalkyl$(C_1-C_2)$alkyl, and $(C_1-C_2)$haloalkyl; and $G^{2b}$ is selected from hydrogen, methyl and ethyl;

or a pharmaceutically acceptable salt, enantiomer or diastereomer thereof.

15. A pharmaceutical composition comprising: i) a pharmaceutically acceptable carrier or diluent; and ii) the compound of claim 12; or a pharmaceutically acceptable salt, enantiomer or diastereomer thereof.

16. A method of treating a subject with a disease or disorder selected from diabetes mellitus, obesity, glucose intolerance, hyperglycemia, hypertension, insulin resistance, dyslipidemia, atherosclerosis, Cushing's syndrome, visceral fat obesity associated with glucocorticoid therapy, Alzheimer's disease, cognitive decline, or metabolic syndrome, comprising the step of administering to the subject an effective amount of the compound of claim 12, or a pharmaceutically acceptable salt, enantiomer or diastereomer thereof.

* * * * *